(12) United States Patent
Bonistalli

(10) Patent No.: US 12,186,050 B2
(45) Date of Patent: Jan. 7, 2025

(54) BIOMETRIC MONITORING SYSTEMS AND METHODS

(71) Applicant: AnneAlise Bonistalli, Chestnut Hill, MA (US)

(72) Inventor: AnneAlise Bonistalli, Chestnut Hill, MA (US)

( * ) Notice: Subject to any disclaimer, the term of this patent is extended or adjusted under 35 U.S.C. 154(b) by 348 days.

(21) Appl. No.: 17/812,970

(22) Filed: Jul. 15, 2022

(65) Prior Publication Data

US 2023/0040102 A1    Feb. 9, 2023

Related U.S. Application Data

(60) Provisional application No. 63/222,861, filed on Jul. 16, 2021.

(51) Int. Cl.
*A61B 5/00*    (2006.01)
*G06F 9/455*   (2018.01)
*G16H 50/30*   (2018.01)

(52) U.S. Cl.
CPC ............ *A61B 5/0022* (2013.01); *G06F 9/455* (2013.01); *G16H 50/30* (2018.01)

(58) Field of Classification Search
CPC ... A61B 5/0022; A61B 5/021; A61B 5/02405; A61B 5/02416; A61B 5/14532;
(Continued)

(56) References Cited

U.S. PATENT DOCUMENTS 10,885,530 B2 * 1/2021 Mercury ................. H04W 4/38
2021/0176066 A1 * 6/2021 Keith, Jr. ................ G06F 21/43

FOREIGN PATENT DOCUMENTS

CA       3 130 205      * 8/2020
WO   WO 2018/218286    * 12/2018

OTHER PUBLICATIONS

Fortino et al., "BodyCloud: A SaaS approach for community Body Sensor Networks", Future Generation Computer Systems 35 ( 2014) 62-79 (Year: 2014).*

(Continued)

*Primary Examiner* — Qian Yang
(74) *Attorney, Agent, or Firm* — Hamilton, Brook, Smith & Reynolds, P.C.

(57) ABSTRACT

Computer implemented biometric methods and systems incorporate sensing biophysical phenomena, translating the phenomena into digital data and transmitting the data to a series of servers operating in an open feedback loop to generate a module. A biometric networking system can include a biometric monitoring cloud computing platform with AI/machine learning augmented models are generated to make user assessments, programs and confidence scores to the healthcare provider systems. The AI/machine learning models can be used by the biometric monitoring network to generate health-related AI processes that analyze relationships treatment techniques and outcomes. AI techniques can be used to calculate movement modeling and confidence scoring including support vector machines, neural networks, and decision trees. The biophysical phenomena may include biometric parameters based on data, such as medical history, exertion, sleep, temperature, cardiovascular events, respiratory events, and muscle and blood pH.

18 Claims, 67 Drawing Sheets

(58) Field of Classification Search
CPC . A61B 5/14542; A61B 5/4815; A61B 5/4872; A61B 5/0205; A61B 5/1118; A61B 5/7267; A61B 5/7282; G06F 9/455; G16H 50/30; G16H 20/30; G16H 20/60; G16H 30/40; G16H 40/67; G16H 50/20; G16H 50/50; G16H 40/63; H04L 63/0442; H04L 63/0861; H04L 67/10
See application file for complete search history.

(56) References Cited

OTHER PUBLICATIONS

Hamidi, "An approach to develop the smart health using Internet of Things and authentication based on biometric technology", Future Generation Computer Systems 91 (2019) 434-449 (Year: 2019).*

Khan et al., "Biometric Systems Utilising Health Data from Wearable Devices: Applications and Future Challenges in Computer Security", ACM Computing Surveys, vol. 53, No. 4, Article 85. Publication date: Jul. 2020. (Year: 2020).*

Xie, K., et al., "Physics-based Human Motion Estimation and Synthesis from Videos," Retrieved on Jul. 14, 2022. https://developer.nvidia.com/blog/nvidia-ai-generating-motion-capture-animation-without-hardware-or-motion-data/.

Jiang, F., et al., "Artificial intelligence in healthcare: past, present and future," Retrieved on Jul. 14, 2022. https://www.ncbi.nlm.nih.gov/pmc/articles/PMC5829945/.

* cited by examiner

BIOMETRIC MONITORING SYSTEMS AND METHODS

RELATED APPLICATION(S)

This application claims the benefit of U.S. Provisional Application No. 63/222,861, filed on Jul. 16, 2021, which includes Appendices A-J. The entire teachings of the above application and Appendices A-J are incorporated herein by reference.

BACKGROUND

There are physiologic monitoring wearables, for example, for gauging biofeedback, health, sleep, fitness, metabolism, and vital status. These devices can process physiological signals that may be obtained from one or more sensors, and may be configured to extract one or more physiological metrics from physiological waveforms.

SUMMARY

Wearables typically operate individually and are implemented as separate systems that lack compatibility with each other due to differences in methods, functionality, and/or data format. In some circumstances, it can be difficult to aggregate data from these tools and wearable devices in a scalable manner. There are potential issues with privacy and security of the data collected by such devices. Additionally, with greater access to such personal information, privacy and security concerning user data is an issue. Users may have several accounts for different devices. For example, users may have an account linked to a heart rate monitoring application, an account linked to a sleep monitoring system, an account linked to an exercise monitoring system, an account linked to a healthcare provider tracking system, and yet another account to a physical training tracking system. The lack of interoperability, security/privacy and accuracy can compromise system performance, as well as impede health and fitness providers ability to provide comprehensive biometric assessments. Further, the monitoring/tracking systems may provide inaccurate assumptions taken out of context based on the extracted physiological metric data, which can reduce the accuracy and efficacy of such systems.

It is desirable to implement a system that increases the efficacy of biometric data computational analysis using secure scalable computer architecture, that also protects sensitive data. The disclosed embodiments herein can implement such a system. In some embodiments, a biometric monitoring network may be provided for continuous biometric, health and fitness monitoring and planning. In some embodiments, the biometric data collected by the biometric monitoring network is processed dynamically based on biomarkers collected from wearable computing devices. The biomarkers collected are encapsulated with data defining a physiological context in which the biomarkers were captured. The biomarkers may be captured using physiological signal processing including exertion data, sleep data, temperature data, cardiovascular data, respiratory data, and muscle pH data, nutrition related metrics, mindset metrics, and wellness metrics to create movement patterns and models. The biometric data computational analysis may be provided by a biometrics monitoring system and then relayed in a secure manner to healthcare provider systems. The biometric data computational analysis may be useful to enable a client to reach physical performance goals, completing health and fitness sessions by computationally assessing, scoring, and making recommendations regarding client performance and progress relative to goals set by the system, provider, client, and analyzing session statistics and changes in body data.

The biometric network system may be used by healthcare providers to assess, monitor, manage, and provide computationally based biometric and wellness recommendations to their clients. The biometric monitoring network can help the provider manage the client's schedule, track their progress, monitor their body data including their physical performance within sessions, as well as heart rate, HRV, blood oxygen levels, sleep, and develop a customized program and plan for the client. In an embodiment, the program/plan encompasses many facets of health, including diet, fitness, physical therapy and sleep requirements, as a function of continuously updated real-time biophysical data. In some embodiments, the system can calculate a score based on a variety of physiological data (or parameters) and other body data associated with the client. In some embodiments, the biometric monitoring network provides a dynamic library that can be used by healthcare providers to manage/monitor/score their client's level, ability, habits, and biometrics to create a customized client plan and program. The system includes a communication interface to enable the provider to communicate with the client throughout their health and fitness program.

In an embodiment, a biometric network system may monitor physiological signals and data from wearable devices. An example wearable device may include a sensor, an input node, an output node, and a computing unit, and interface with a front-end server, and a back-end server. The wearable device may be configured to detect, analyze, and transmit biophysical phenomena from a host, the sensor being coupled to a component configured to translate the biophysical phenomena into digital information. The input node is configured to translate the digital information to an input signal. The input signal is then transmitted through an input channel. The input channel is configured to communicate with the sensor, on a proximal end of the input channel with respect to the sensor, and a processor, on a distal end of the input channel with respect to the sensor, whereby the input signal is transmitted from the sensor to the processor. The output node is configured to transmit an output signal through an output channel. The output channel is configured to communicate with the processor, on a proximal end of the output channel, and a receiver, on a distal end of the output channel with respect to the processor, whereby the output signal is transmitted from the processor to the receiver. The computing unit is configured to receive, store, and compute the output signal communicated to the computing unit from the receiver. The front-end server is configured to execute a first algorithm. The front-end server produces parameters using the digital information computed by the computing unit. The back-end server is configured to execute a second algorithm. The back-end server produces parameters using the digital information received by and stored in the memory unit, generating the physiological signal processing system.

In an embodiment, a method for generating a biometric network system comprises detecting biophysical phenomena via a plurality of wearable devices, each having one or more sensors, translating the biophysical phenomena into digital information, transmitting the digital information to a processor, processing the digital information, storing the digital information, and producing a parameter, thereby generating a physiological signal processing system. The wearable device may be coupled to a host. The processor may be in communication with a front-end server and a back-end server. The digital information is processed via the front-end server executing a first algorithm stored in the processor. The digital information is stored in a memory component. Producing a parameter occurs through the back-end server executing a second algorithm. The digital information is stored in the memory component. The memory component is in communication with the wearable sensor and a secure server. The second algorithm is stored in the secure server.

In an embodiment, a server component executes physiological signal processing system for generating a physiological signal processing system operating in an open feedback loop. The server comprises a useable digital medium having a code embodied therein configured to cause a computing device to provide secure access to an application, communicate to a wearable device, translate biophysical information into digital information, and produce a parameter. The wearable device is coupled to a host. The wearable device has an input node and an output node. The digital information is transmitted to the computing device from the wearable device. The digital information is transmitted from the computing device to a processor configured to analyze the digital information. The parameter produced from the digital information received by the processor is stored in a secure database.

In an embodiment, a biometric network system includes a biometric monitoring processing system. The biometric monitoring system may include an embedded movement and recovery programming smart library that enables dynamic reprograming of the library's components customized for a particular user and healthcare provider. A packetizer can be used to dynamically create modeled movement patterns in the library based on biomarkers received from the biomarkers extracted from the physiological signal processing, which may receive input data from a plurality of input sources including motion detectors, wearables, EEGs. New movement patterns may be dynamically modeled by the biometric monitoring system in response to the biomarkers detected. The biometric monitoring system compiles the dynamically created modeled movement patterns to enable assessments of the user. The biometric monitoring system can implement the dynamic movement and recovery library to enable custom computational metrics to be created including customized assessments, custom queries, and notes to be associated with each of the dynamically created modeled movement patterns.

The biometric monitoring system enables tracking of the modeled movement patterns for multiple sectors. A mindset score may be factored in to create the movement patterns. The mindset score may be determined based on a multitude of factors including input from heart rate enabled wearable devices measuring respiratory rate, breaths per minute. The mindset score may be used to create a confidence score for each of the tracked metrics. Further metrics are tracked by the system to create the modeled movement patterns including tracked strength metrics, and subjective and objective scoring metrics, which are applied to the users programming platform.

A biometric computer network system may be implemented with a biometric monitoring cloud computing platform that includes a plurality of biometric monitoring network nodes. The nodes may be configured to process biomarkers from a plurality of biometric devices associated with a user. Each of the plurality of biometric devices may be configured with one or more sensors, one or more processors, and a memory. The one or more processors of the biometric devices may be operatively connected with the memory, and the one or more sensors, where the memory stores computer-executable instructions for causing the one or more processors to transmit the biomarkers to the biometric monitoring cloud computing platform.

At least one of the plurality of biometric monitoring nodes may execute an instance of a virtual machine at a healthcare provider computing system to deploy an encapsulated quantified assessment derived from quantifying the biomarkers from the plurality of biometric devices. The biometric monitoring cloud computing platform may compute the encapsulated quantified assessment based on movement models associated with the user.

The biometric monitoring cloud computing platform may use the movement models to create a software movement library dynamically adapted to a movement profile generated for the user. The biometric computer network system may include an artificial intelligence based video processing system component that computationally processes a video signal having a plurality of frames depicting the user performing movements.

The biometric monitoring cloud computing platform may process the plurality of video frames from the video signal to create a movement profile and movement models, where the movement models are an encoded form of video signal data from a plurality of video frames.

The artificial intelligence based video processing system component of the biometric monitoring cloud computing platform may be configured to model such correspondences to generate the movement models.

The artificial intelligence based video processing system component may trigger a resampling request to dynamically update the software movement library. The artificial intelligence based video processing system may respond by requesting another transmission of video signal having video framings depict the user performing further movements in response to a triggered reassessment. The artificial intelligence based video processing system component of the biometric monitoring cloud computing platform may be configured to model such correspondences to generate updated movement models.

The biometric monitoring system may trigger a reassessment and request biomarkers and related input from the biometric devices based on progress over time. The biometric monitoring system can be configured to implement automatic reassessments at intervals. In some embodiments, the reassessments may trigger push or pull notifications based on the volume of progress and frequency of data collection. Automatic push and pull nonfictions to secure new biomarkers from biometric devices may be triggered in response the system requesting reassessments.

Such automatic reassessments may be triggered based on a variety of computational findings. For example, an automatic reassessment may be triggered based on a detected injury. Checkpoints of movement pattern progression can trigger an automatic reassessment of biomarkers. Automatic reassessments may be trigger based on a recovery score being consistently low. Automatic reassessments may be triggered based on metrics gathered from biomarkers of a period of time, including consistently low sleep scores, variations or irregular respiration rate readings, repeated heart-rate recovery (HRV) readings, variations or irregular resting heartrate readings, body temperature readings consistently 2 degrees above normal rate. Automatic reassessment may be triggered in response to recovery scores dropping 10% or more on certain metrics (e.g. readiness score, sleep score, respiration) detected which could be an indication of stress or illness. In the event of a reassessment/ reevaluation, input readings from wearable devices would automatically resampled to secure new data sets of biomarkers for the dynamic computation of dynamic movement patterns for the system library.

It should be noted that the above Summary is for illustrative purposes only, and intended to introduce a selection of some of the concepts from the disclosure, which are further described below. The above Summary is not intended to limit scope of the invention.

BRIEF DESCRIPTION OF THE DRAWINGS

The foregoing may be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Appendices

The following appendices are being filed concurrently with the present application and are incorporated herein by reference in their entirety:

Appendix A—Documents Table of Contents
Appendix B—ALL SECTORS (Global) Description
Appendix C—Metrics & Tracking Description
Appendix D—Mindset Sector Outline v4
Appendix E—Mindset Workflow
Appendix F—Movement-Recovery Workflow
Appendix G—Movement Sector Outline
Appendix H—Recovery Sector Outline
Appendix I—7-2021 v.2 Nutrition—MEAL PLAN CALCULATOR
Appendix J—Nutrition Library Description
Appendix K—Nutrition Sector Outline
Appendix L—Nutrition
Appendix M—Movement & Recovery Programming, Library and Naming Description v4
Appendix N—OS ADMIN Library, Assessments and Tests
Appendix O—OS Provider Library, Assessments and Tests
Appendix P—Movement Library
Appendix Q—Recovery Library
Appendix R—Nutrition Library
Appendix S—Metrics & Tracking
Appendix T—OS Features and Functionality
Appendix U—OS Page Detail
Appendix V—Client Components Description and Breakdown
Appendix W—Mindset Library v4 Description
Appendix X—Super Admin White Label Module Components Description
Appendix Y—Super Super AdminSuper AdminAdmin App Diagram
Appendix Z—Client App Diagram
Appendix AA—White Label Module Flow The above referenced appendices are for illustrative purposes only and to be non-limiting. The above referenced appendices are not intended to limit scope of the claims of the present application.

Example Biometric Network System Architecture and Features

The present disclosure provides example implementations of a biometric network system that computationally monitors biomarkers (biometric data) detected from computing devices capturing physiological signals including health and fitness data. An example biometric network system can be provided that increases the efficacy of computational analysis of the biomarkers using secure scalable computer architecture with enhanced security. In some embodiments, the biometric network system uses biometric monitoring and dynamically creates motion patterns and adds them to the movement library for the individual. Such motion patterns can be used for continuous biometric, health and fitness monitoring and planning, as well as for detecting and monitoring potential symptoms for serious conditions and ailments that may pertain to the individual. An illustrative example of motion patterns that are shown in Appendix P—Movement Library.

Figure 1A:
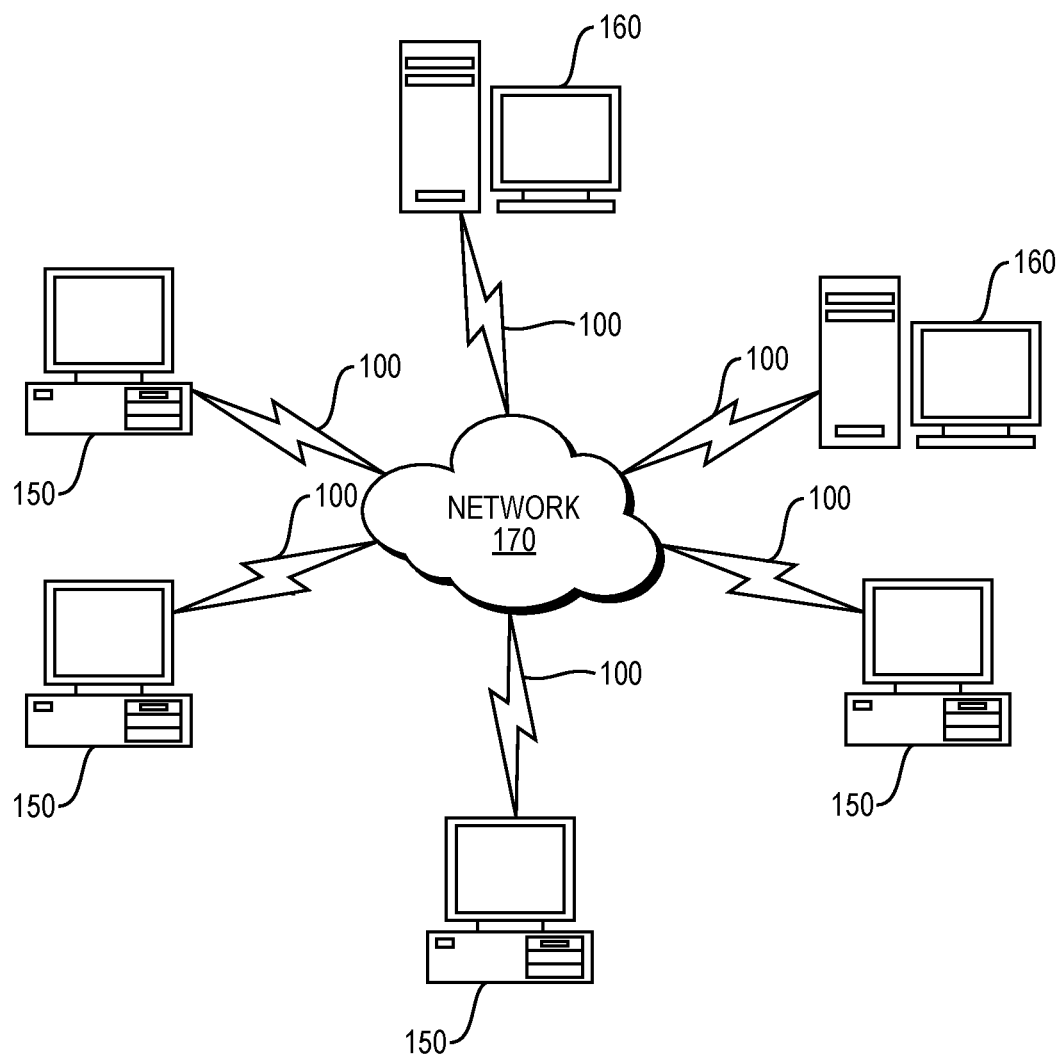
FIG. 1A is a non-limiting schematic view of a computer network or similar digital processing environment in which embodiments may be implemented.
Figure 1B:
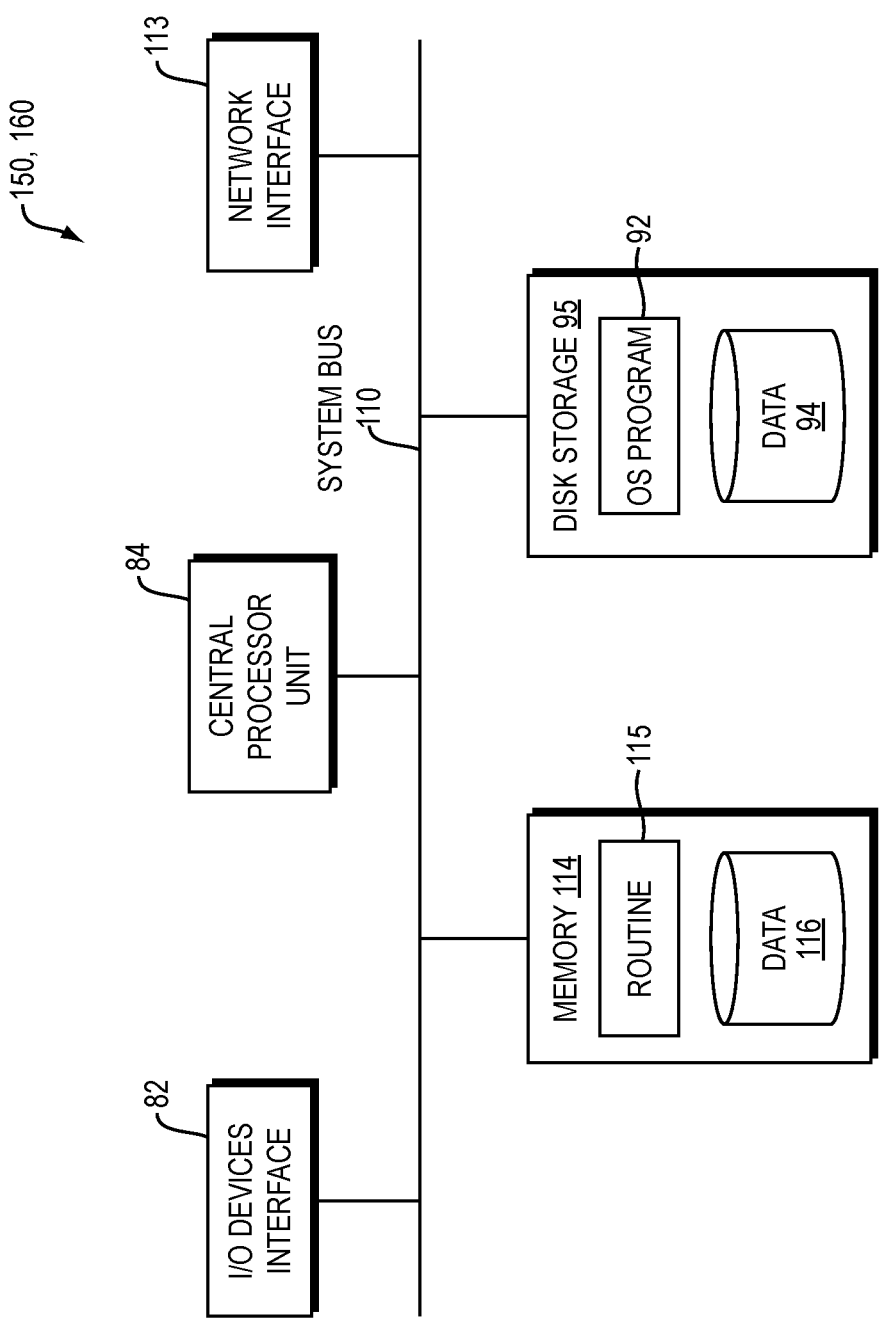
FIG. 1B is a non-limiting block diagram of the internal structure of a computer (e.g., client processor/device or server computers) in the computer network of FIG. 1A.

An example implementation of a biometric network system for generating physiological signal processing system according to an embodiment of the invention may be implemented in a software, firmware, or hardware environment. FIG. 1A illustrates one such example system in which embodiments of the present invention may be implemented. Client computers/devices 150 (including wearables 205 FIG. 2A) and server computers/devices 160 provide processing, storage, and input/output devices executing application programs and the like.

Biometric monitoring devices 150/205 may be linked directly or through communications network 170 to other computing devices, including other client computers/devices 150 and server computer/devices 160. In one embodiment, the communication network 170 can be part of a wireless or wired network, remote access network, a global network (i.e. Internet), a worldwide collection of computers, local area or wide area networks, and gateways, routers, and switches that currently use a variety of protocols (e.g. TCP/IP, Bluetooth®, RTM, etc.) to communicate with one another. The communication network 170 may also be a virtual private network (VPN) or an out-of-band network or both. The communication network 170 may take a variety of forms, including, but not limited to, a data network, voice network (e.g. land-line, mobile, etc.), audio network, video network, satellite network, radio network, and pager network. Other electronic device/computer networks architectures are also suitable.

In some embodiments, the communication network 170 may be implemented as using scalable architecture that can scale up to meet increased workloads and analysis of biomarkers. The biometric network system may be configured to enable sensitive personal identifying information about a user/patient's/client's biomarkers and related metrics, which may be subject to privacy regulations, to be stored on a healthcare service providers intranet. The biomarkers and related metrics may be anonymized and processed by a biometric monitoring system.

Biometric Monitoring Cloud Computing Platform

Referring to FIGS. 1A, 1B, 2A, 2B, 2C, the communication network 170 may enable communication in the biometric network system among computing components 150, 160. For example, computing components 150, 160 may include biometric monitoring cloud computing platform 204b and a healthcare service provider system 204, 204a, both of which may be communicating with user devices including biometric devices 150, 205 via the biometric API 208. The biometric monitoring cloud computing platform 204b may be scalable, configured as a cloud computing system, such as a Platform as a service (PaaS) or application platform as a service (aPaaS) that enables the healthcare provider system 204, 204a to provision, instantiate, run, and manage a modular locally processing instances of the biometric monitoring computing platform 204b, such as super admin components. See, e.g. Appendix X—Super Admin White Label Module Components Description and Appendix Y—Super Super AdminSuper AdminAdmin App Diagram.

In some embodiments, scalability is a feature of the biometric monitoring cloud computing platform 204b as it is configured to increase the capacities of allocated virtual resources at the healthcare provider system 204, 204a, as well as the healthcare provider system's databases and infrastructure on demand.

In some example preferable embodiments, the biometric monitoring cloud computing platform 204b vertically scales by increasing the capacity of its individual computing nodes through hardware improvements, e.g., change to other nodes with higher memory, or increase the number of CPU cores. The biometric monitoring cloud computing platform's 204b scalable architecture is further configured to protect sensitive medical data from the healthcare provider 204, 204a, and it accomplishes this by encapsulating all of the sensitive medical data locally on the healthcare provider 204, 204a system through multiple instances of virtual machines that are dynamically and temporarily operating at the healthcare provider system 204, 204a. biometric monitoring cloud computing platform 204b rearchitects configurations of server-side session state management, providing a mechanism for multiple servers to process requests for the same session without losing the session state data, implementing loose coupling between state and application services without transmitting the healthcare data to the service provider biometric cloud computing platform 204b.

The biometric monitoring system may computationally process the biomarkers to detect data points. The data points can be a set of markers that are tracked at said intervals most often associated with metrics and items. Data points can be processed by the biometric monitoring system to detect patterns and trends over time that can be tracked in order to responsively respond and adapt. The biometric monitoring system computes metrics based on the biomarkers. The computed metrics are a type of measurement, albeit a more useful measure that carries more information. Through the analysis of metrics and patterns of data, these metrics can be utilized by the biometric monitoring system to gain an understanding of past and present performance to forecast future performance. See Appendix S—Metrics & Tracking FIG. 1B diagram of the internal structure of a computer (e.g., client processor/device 150 or server computers 160) in the computer system of FIG. 1A. Each computer 150, 160 contains system bus 179, where a bus is a set of hardware lines used for data transfer among the components of a computer or processing system. The system bus 179 is essentially a shared conduit that connects different elements of a computer system (e.g., processor, disk storage, memory, input/output ports, network ports, etc.) that enables the transfer of information between the elements. Attached to system bus 179 is I/O device interface 182 for connecting various input and output devices (e.g., keyboard, mouse, displays, printers, speakers, etc.) to the computer 150, 160. Network interface 186 allows the computer 150, 160 to connect to various other devices attached to a network (e.g., network 170 of FIG. 1A). Memory 114 provides volatile storage for computer software instructions 115 and data 116 used to implement example embodiments of the biometric network system including the biometric monitoring system 200, such as the biometric API 208 of FIG. 2A, the encoder 210, software components of FIGS. 2A-2D, and its various software libraries including metrics and tracking software libraries (e.g. Appendix S—Metrics & Tracking, Appendix J Nutrition Library Description, Appendix M Nutrition Library, Appendix M—Movement & Recovery Programming, Library and Naming, Appendix N—OS Admin Library, Assessments and Tests, Appendix P—Movement Library, Appendix Q—Recovery Library, Appendix S—Metrics & Tracking, Appendix W—Mindset Library, and Appendix O—BOOM OS Provider Library, Assessments and Tests).

Disk storage 95 provides non-volatile storage for computer software instructions 92 and data 94 used to implement embodiments of the present invention. Central processor unit 84 is also attached to system bus 110 and provides for the execution of computer instructions. In one embodiment, the processor routines 92 and data 94 are a computer program product (generally referenced 92), including a computer readable medium (e.g., a removable storage medium such as one or more DVD-ROM's, CD-ROM's, diskettes, tapes, cloud storage, SD cards, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

Software implementations 92 of the biometric network system including the biometric monitoring system and related components may be implemented as a computer readable medium capable of being stored on a storage device, which provides at least a portion of the software instructions for the biometric network system. Executing instances of respective software components of the biometric network system, such as software components that process biomarkers from sensor readings and body data. Software implementations 92 may include to implement example embodiments of the biometric network system including the biometric monitoring system 200, such as the biometric API 208 of FIG. 2A, the encoder 210, software components of FIGS. 2A-2D, and its various software libraries including metrics and tracking software libraries as discussed here.

Biometric monitoring devices 150, 205 include sensors that may measure a user's heart rate, body temperature, movement and physiology. The sensors can be embedded in smartphones, wearable technologies (e.g., wrist bands, skin patches), or everyday objects (e.g., smart cap bottles) that offer the opportunity to collect biological, physiological, or behavioral patient data, continuously, remotely, and unobtrusively. The biomarkers from the devices 150, 205 may be pulled or pushed to the cloud platform 204b or the healthcare provider system 204a, 204 (depending on the privacy restrictions) for assessment processing.

In one example preferred embodiment, a biometric monitoring device is configured as a physiological signal processing system that includes multiple sensors, including a photoplethysmograph (PPG) sensor that is configured to generate a physiological waveform, and an inertial sensor that is configured to generate a motion signal. A physiological metric sampler is configured to extract and encode a physiological metric from the physiological waveform that is generated by the photoplethysmograph sensor. The physiological metric sampler includes a resampler that resamples subsequent instances the motion signal and normalizes the resampled signal to create a motion model of the motion signal. To reduce computational processing latency, the biometric monitoring device may be configured to create a predicted motion model based on a redundancy detected in prior instances of the motion signal.

The biometric monitoring devices can be configured to provide minute-by-minute, second by second, measurements enabling the measurement of health, disease progression, and treatment. In some embodiments, the biometric monitoring device sensors integrate seamlessly into any wearable device and use active signal characterization technology that can enable highly accurate biometrics during various movements including vigorous exercise.

In some embodiments, the biometric monitoring device sensors can measure even weak blood flow signals during physical activity. In one preferred embodiment, the biometric sensor which is made possible by an ultra-miniaturized optomechanical sensor module that includes an optical detector, an optical emitter, an accelerometer and specialized sensors that enable continuous heart rate monitoring technology.

The system 200 may process a client's health data including body (head, neck, arms, hands, torso, and legs), human (blood glucose, blood oxygen, blood pressure, body fat, body mass index, and genetic information. Those readings may be processed by the system to provide readiness, sleep, and activity scores of the client.

The software components may be implemented as computer program products, and can be installed by any suitable software installation procedure, as is well known in the art. In some embodiments, the software components may interface with other wearable application programming interfaces (APIs), including the following APIs: Oura Cloud, Movesense, ZivaCare, Garmin Health, Suunot Authorisation, Suuunto Workout, Polar TeamPro, Polar TeamPro, Fitbit, Google Fit, Google Health, Samsung Simband, Whoop, Apple.

In an embodiment, at least a portion of the system software instructions may be downloaded over a cable, communication and/or wireless connection via, for example, a browser SSL session or through an app (whether executed from a mobile or other computing device). In other embodiments, the system software components, may be implemented as a computer program propagated signal product embodied on a propagated signal on a propagation medium (e.g. a radio wave, an infrared wave, a laser wave, a sound wave, or an electrical wave) propagated over a global network such as the Internet, or other networks. Such carrier medium or signal provides at least a portion of the software instructions for the methods and systems disclosed herein.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 150, 160 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like. In other embodiments, the computer program product 92 may be implemented as a biometric monitoring cloud computing platform 204, or other installation or communication supporting end-user, including the biometric API 208.

Example embodiments of the invention are based on the premise that online services may be significantly enhanced when a device can be trusted to its said health and integrity and to execute instructions exactly as requested. A service provider generally has confidence in its servers because they are under administrative control and usually protected physically. However, nearly all of the service provider's services are delivered to users through devices the service provider knows very little about and over which it rarely exerts any control.

Example embodiments of the invention can include a frontend web application used by health and fitness clients to manage their training schedule and track their progress. Users can receive customized health and fitness plans and schedules from their team of providers, as well as be able to input and track their own progress. Example embodiments of the invention also include a backend platform for the Super admin/admin/provider portal. The backend platform provides a super administrator, an administrator, a provider and a concierge role, and the ability to coordinate and manage content and users. The backend platform can include user permissions, scheduling, reporting and time management, task management, team management, location management, client management, library and content management, program building, and messaging. Client management can include the creation and customization of client plans. Library and content management can include movement, mindset, recovery, and nutrition. Library and content management can also include creating and utilizing workout and plan templates. Metrics management can also include creating and utilizing custom metrics.

In example embodiments, generating a physiological signal processing system can include exposing an anatomical region to a sensor provided by a wearable device 150, 205. The wearable device can be coupled to the backend platform and to the frontend platform, both of which are in communication with the wearable device. The sensor on the wearable device provides data to the processor for calculating data that is used to generate a physiological signal processing system for use in analyzing and assessing movement, mindset, recovery and nutrition.

In an example embodiment, a physiological signal processing system is used by a provider to develop client-specific programs, including a collection of sessions over a period of time that can be saved as a template and applied to a client's plan. The programs last for a period of time called a phase, which can be any number of days. A session is one unit of time that a client performs an activity. Scheduled sessions, in person or virtual, has a calendar event associated with it with two or more guests. Unscheduled sessions/individual sessions do not have a calendar event associated with it. Unscheduled sessions/individual sessions can also be designated to a certain time, but does not appear as a calendar event if no calendar event was created for it.

In an embodiment, a system for generating a physiological signal processing system comprises a wearable device having a sensor, an input node, an output node, a computing unit, a front-end server, and a back-end server. The wearable device is configured to detect, analyze, and transmit biophysical phenomena from a host, the sensor being coupled to a component configured to translate the biophysical phenomena into digital information. The input node is configured to translate the digital information to an input signal. The input signal is then transmitted through an input channel. The input channel is configured to communicate with the sensor, on a proximal end of the input channel with respect to the sensor, and a processor, on a distal end of the input channel with respect to the sensor, whereby the input signal is transmitted from the sensor to the processor. The output node is configured to transmit an output signal through an output channel. The output channel is configured to communicate with the processor, on a proximal end of the output channel, and a receiver, on a distal end of the output channel with respect to the processor, whereby the output signal is transmitted from the processor to the receiver. The computing unit is configured to receive, store, and compute the output signal communicated to the computing unit from the receiver. The front-end server is configured to execute a first algorithm. The front-end server produces parameters using the digital information computed by the computing unit. The back-end server is configured to execute a second algorithm. The back-end server produces parameters using the digital information received by and stored in the memory unit, generating the physiological signal processing system.

In some embodiments, the back-end server is further configured to translate the digital information into user-readable data. In some embodiments, the back-end server is further configured to automate the system. In some embodiments, the back-end server is further configured to prevent third-party users from accessing the system and the information stored and communicated therein. In some embodiments, the input signal is generated by the sensor. In some embodiments, the component is further configured to detect a change in the biophysical phenomena. In some embodiments, the wearable is configured to communicate with a navigation device. In some embodiments, the wearable device and the computing unit are configured to communicate with each other.

In an embodiment, a method for generating a physiological signal processing system comprises detecting biophysical phenomena via a wearable device having a sensor, translating the biophysical phenomena into digital information, transmitting the digital information to a processor, processing the digital information, storing the digital information, and producing a parameter, thereby generating a physiological signal processing system. The wearable device having the sensor is coupled to a host. The processor is in communication with a front-end server and a back-end server. The digital information is processed via the front-end server executing a first algorithm stored in the processor. The digital information is stored in a memory component. Producing a parameter occurs through the back-end server executing a second algorithm. The digital information is stored in the memory component. The memory component is in communication with the wearable sensor and a secure server. The second algorithm is stored in the secure server.

In some embodiments, the biomarkers further comprise exertion data, sleep data, temperature data, cardiovascular data, respiratory data, and muscle pH data. In some embodiments, generating the physiological signal processing system occurs in an open feedback loop. See Appendix S—Metrics and Tracking.

Dynamic Movement Library

The biometric monitoring system may include a hierarchically structured movement and recovery programming smart library. The library may be configured to enable dynamic reprograming of the library's components customized for a particular user and by a healthcare provider. A network packetizer can be used to dynamically create network packets transmitting a dynamically updated modeled movement and recovery library 116 for use locally for assessments to enable an offline solution.

New movement patterns may be dynamically modeled by the biometric monitoring system in response to the updated metrics and detected movement patterns. The biometric monitoring system compiles the dynamically created modeled movement patterns to enable accurate assessments of user's motion mobility in real-time. The biometric monitoring system can implement the dynamic movement library to enable custom computational metrics to be created including customized assessments, custom queries, and notes to be associated with each of the dynamically created modeled movement patterns. See Appendix M, P and Q.

The biometric monitoring system 200 can include API components 208 that enable real-time capture of a user's motion during exercise and create movement patterns based on the physical strengths and limitations detected. Artificial intelligence components can be used to capture the user's movement using motion capture to create a model of the individual into, and provide a physics simulation to accurately imitate the real-life movement during exercise. These motion models would be used as a basis to create customized motion metrics for the individual.

The biometric monitoring system may include an embedded movement and recovery programming smart library that enables dynamic reprograming of the library's components customized for a particular user and healthcare provider.

The biometric API 208 of the system 204b can interface with an adaptive movement library that adapts in real-time based on the user's physical ability level. The system uses the movement quantifications from the AI components to apply a movement library to a user. The definition of a term dynamically changes based on the movement categories associated with the user. Based on knowing the user's ability, the system 204b allocates a category of movement patterns associated with the user. It ranges from a user that may be immobile and perhaps learning to walk, to a user that is a high-level athlete. The system 204b quantifies the user's ability in an assessment, reassesses and dynamically creates unique movement libraries that are tailored to the specific user's ability.

Quality of movements to progress to next body position and pattern progression to adaptively learn and progress movement patterns. Responsively regress patterns based on AI predicted movement patterns which leads to injury prevention, avoidance of injury and proactive treatment prevention. Learned system technology adapt health plan and progress and regress movement patterns.

As an example, artificial intelligence components can be used to customize a motion for the user, such as a deadlift through AI system verification of if the user does not meet standards of movement pattern i.e. there is a curvature in the user's spine and based on the subjective and objective score of metrics in cumulation with the poor movement pattern the system automates by moving the pattern back to a lower level body position. For example, the system then creates a customized movement model for the user in which the body position to a half kneeling variation deadlift pattern as is automated based on the movement sub category association of patterns. SEE Appendix M—BOOM Movement & Recovery Programming, Library and Naming Description v4 and Appendix P BOOM Movement Library v4—The system automates this and learns patterns adaptively to recommend movement patterns leading to the ability to improve movement patterns.

In one example, training motion synthesis models can be created from the motion capture input secured via a computing device 150, 205 and estimations can be computed by enforcing physics constraints through contact invariant optimization, including computation of contact forces. The biometric monitoring system use an artificial intelligence based video processing system to create motion models based on a time-series motion models on the refined poses, synthesizing both future motion and contact forces. In this way, a movement model library including modeled movements for each individual can be created using pose estimation using physics-based refinement, and motion synthesis results from video capture. Examples of this technique are disclosed in Physics-based Human Motion Estimation and Synthesis from Videos, by Kevin Xie, Tingwu Wang, Umar Iqbal, Yunrong Guo, Sanja Fidler, and Florian Shkurti, the entire teachings of which are incorporated herein by reference.

The biometric monitoring system 200 can enable tracking of the modeled movement patterns for multiple sectors. A mindset score may be factored in to refine the movement patterns. The mindset score may be determined based on a multitude of factors including input from heart rate enabled wearable devices measuring HRV or biofeedback data. The mindset score may be used to create a confidence score for each of the tracked metrics. Further metrics are tracked by the system to create the modeled movement patterns including tracked strength metrics, and subjective and objective scoring metrics, which are applied to the users programming platform.

The movement and recovery library for an individual is initialized by a global movement library that is populated by verified industry standard tags, as well as various other movements nomenclature in the industry to have variability. The movement library is reconfigured and customized based on the individual. Each movement in the movement library associated with the individual may be reconfigured with smart tags and movement definitions may be dynamically reconfigured based on a movement or recovery assessment of the individual. Insert AA paragraph here. In this way, the biometric monitoring system can create automatically create a movement program that is based on limitations of an individual (chart based on a body position, corelating body position to movement program). See, e.g. Appendix P—Movement Library, Appendix Q—Recovery Library, Appendix S—Metrics & Tracking. The biometric monitoring system creates a custom plan for an individual by searching and parsing its movement library based on key areas, such as body position, pull, push (subcategory chest or back, linear or lateral). It enables searching using a name system based on each individual pattern, movement, smart way to easily select, also based on the fitness equipment. See Appendix F—Movement-Recovery Workflow and Appendix M—Movement & Recovery Programming, Library and Naming Description v4.

The biometric monitoring system may trigger a reassessment for the movement and recovery program. The reassessment will automatically pull biomarkers and related input from the biometric devices based on progress over time. The biometric monitoring system can be configured to implement automatic reassessments at intervals. In some embodiments, the reassessments may trigger push or pull notifications based on the volume of progress and frequency of data collection. Automatic push and pull nonfictions to secure new biomarkers from biometric devices may be triggered in response the system requesting reassessments.

Such automatic reassessments may be triggered based on a variety of computational findings. For example, an automatic reassessment may be triggered based on a detected injury. Checkpoints of movement pattern progression can trigger an automatic reassessment of biomarkers. Automatic reassessments may be trigger based on a recovery score being consistently low. Automatic reassessments may be triggered based on metrics gathered from biomarkers over a period of time, including consistently low sleep scores, variations or irregular respiration rate readings, variations or irregular resting heartrate readings, body temperature 2 degrees or more above norm. Automatic reassessment may be triggered in response to recovery scores dropping 10% or more on certain metrics (e.g., sleep score, respiration rate) detected which could be an indication of stress or illness. In the event of a reassessment/reevaluation, input readings from wearable devices would be automatically resampled to secure new data sets of biomarkers for the dynamic computation of dynamic movement patterns for the system library.

As shown in Appendix J of U.S. Provisional Application No. 63/222,861, filed on Jul. 16, 2021, which is incorporated herein by reference, all metrics are tracked and progress is tracked over time and the program is reconfiguring itself over time.

Each movement from the dynamic movement and recovery library item has a movement pattern is associated with them. The smart library item is associated and attached to the movement and recovery library associated with the individual. Once updated, the movement and recovery library is recompiled and accessible for use by the biometric network system to enable assessments of user. The dynamic movement and recovery library and programming capability enables custom tracking and assessments, and enables questions and notes to be associated with each movement being tracked by the biometric monitoring system.

Tracking strength numbers, and subjective scoring, all assortments are applied to the individual's programming. Over time, the system reassess data points based on progress over time. Checkpoints of movement pattern progression triggers a reassessment of data points.

Automatic reassessments every 3-6 months but many adjust based on the volume of progress and frequency of data collection. Automatic reassessment may be triggered based on an injury. Automatic reassessment may be triggered by recovery score being consistently low. Changes in a recovery score would warrant a reassessment, and wearable data would be pulled to assess sleep score for period, respiration rate change, increased resting Heartrate, increased body temperature. 10% below normal rate for recover score may trigger reevaluation.

Admin Functions

The biometric network system architecture is configured with a hierarchy of modules within the system including security features of the system 200. Users of the system 200 are only shown a matrix that is customized based on its permissions.

In one embodiment, a global "super admin" master admin matrix is encapsulated via a virtual machine at the healthcare provider 204 system. The healthcare provider system may be implemented as a secure private intranet to enable HIPPA compliance at a healthcare provider system 204. The functionality with the global super admin is not accessible by some portions of the biometric monitoring system, such as the biometric monitoring cloud computing platform 204b, including certain computational components of the AWS/SaaS system hosting the biometric monitoring system 200.

In this way, the healthcare provider does not have to share any patient data, but can utilize the biometric monitoring system to provide a health and fitness system for its patients. Further solutions including encapsulating patient date in an offline solution to ensure HIPPA compliance.

Example System Security

Certain example embodiments may be based on the premise that online services may be significantly enhanced when a device can be trusted to be what it says it is and to execute instructions exactly as asked. A service provider generally has confidence in its servers because they are under administrative control and usually protected physically. However, nearly all of the service provider's services are delivered to users through devices the service provider knows very little about and over which it rarely exerts any control.

Through the use of trusted execution technology, certain inventive embodiments, such as the virtual machines at the healthcare provider site 204, 204a, are able to provide a service provider with an oasis of trust in the unknown world of consumer devices. Basic capabilities such as "sign this", or "decrypt this" are executed outside the murky world of the main OS. Keys can be generated and applied without ever being exposed in memory and can be attested to through a chain of endorsements traced back to the device manufacturer.

Certain aspects of the invention enable trust in devices. Some embodiments operate on the fundamental premise that a reliable relationship with a device can make for a much safer, easier and stronger relationship with an end user. Achieving this requires knowing with confidence that a device involved in a current transaction is the same device it was in previous transactions. It also requires assurance that a device may not leak protected information if it is requested to perform sensitive operations such as decryption or signing.

One example preferred embodiment includes device code executed in the Trusted Execution Environment (TEE). The TEE preferably is a hardware environment that runs small applets outside the main OS of the device 150, 205. This protects sensitive code and data from malware or snooping with purpose-built hardware governed by an ecosystem of endorsements, beginning with the device manufacturer. This ensures the integrity of the user's sensitive data including analytics, recommendations, and modeling of the user's diagnostics, including mindset, recovery, nutrition, and movement assessments is protected and untampered with. Not only does this protect the user's privacy, but it attests to the integrity of the data to the healthcare service provider 204.

Device Integrity Attestation/Authentication—Some Example Embodiments

Figure 2A:
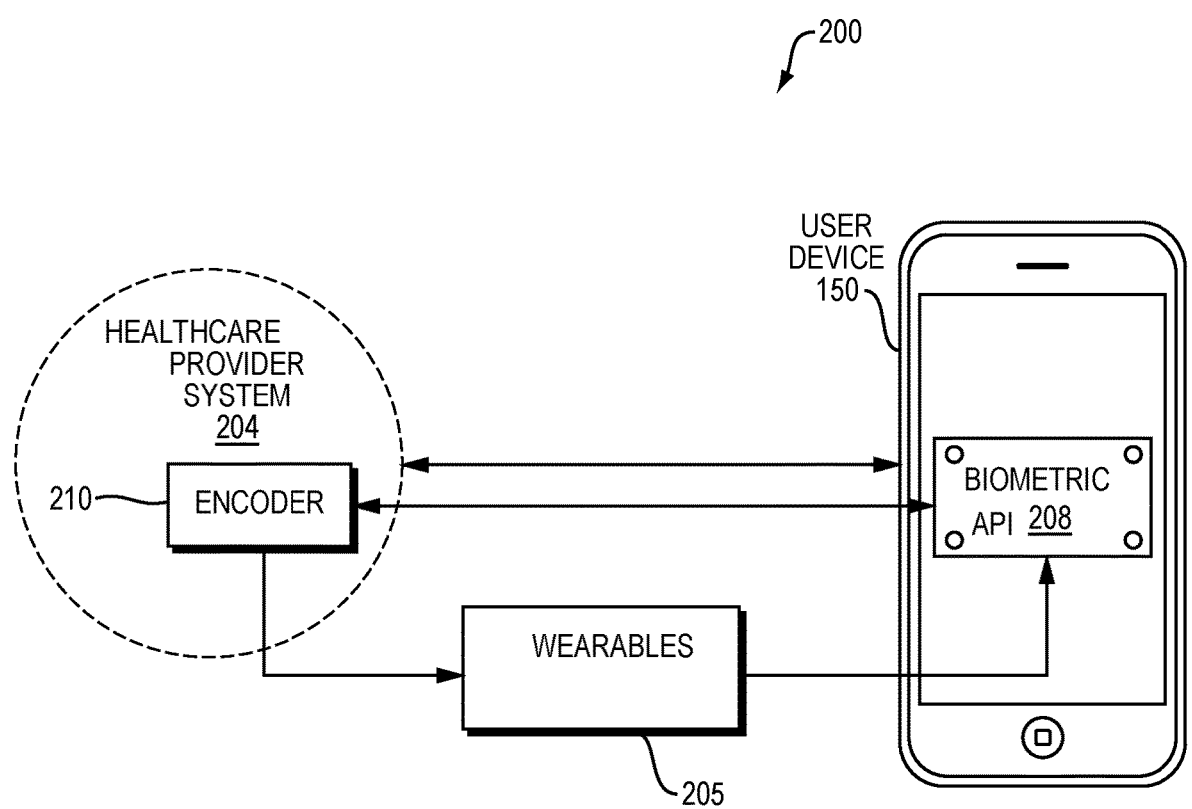
FIG. 2A is a non-limiting block diagram showing an example biometric monitoring system according to an embodiment.

FIG. 2A is a block diagram showing an example device authentication system according to the invention, with biometric and biofeedback components 200. With these system components 200, web developers and app developers can make use of hardened encryption and identity keys in the wearable user devices 150, 205 through an application program interface (API). In addition, further services may be provided built on these system components 200 for device management, backup, attestation to biomarkers captured, etc. To support this system, the registration of identity keys and a set of device management services for attestation of accuracy of biomarkers, backup and wearable device grouping, are managed.

In a preferred example embodiment, it would be the intent of the system 200 not to maintain mission critical data as in conventional approaches, but rather to provide a biometric monitoring cloud computing platform 204b for seamless yet very secure connections between healthcare service provider system 204 and user wearable devices 150, 205 to enable analytics, recommendations, and modeling of the user's diagnostics, biomarkers, including mindset, recovery, nutrition, and movement assessments. On one end of the system is the Encoder 210 which prepares an instruction for a User Device 205 and at the other is the biometric components including biofeedback APIs and codec 208 that can act on that instruction. A Protocol according to an embodiment of the system 200 defines how these instructions and replies are constructed.

Biometric components including biofeedback APIs, codec, and applet 208 preferably embodies the innovative binding between the physical and digital works. The Biometric components including biofeedback APIs, codec, and applet 208 locks features of the user's identity, wearable 205 readings, transaction and attestation to biomarker readings from the hardware of the Devices 150, 205.

Figure 2B:
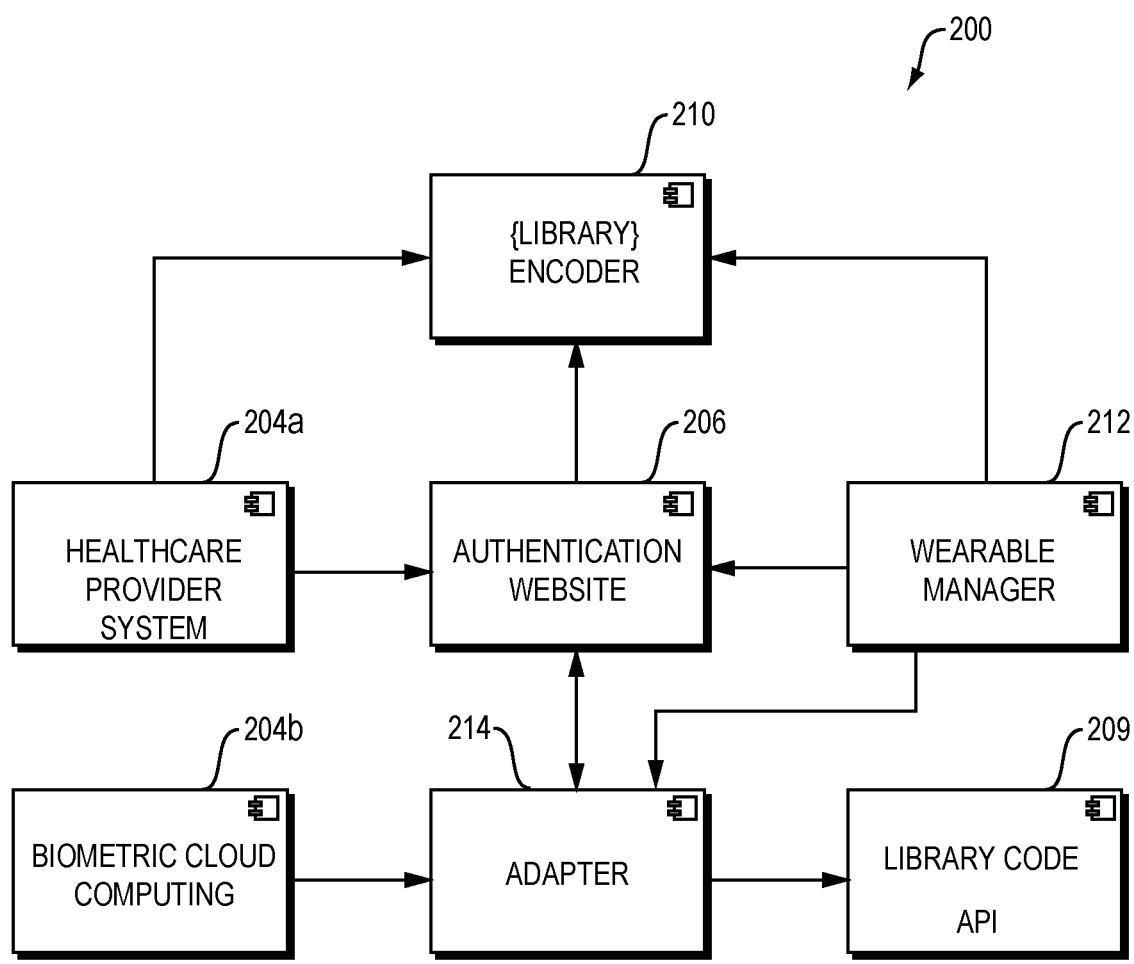
FIG. 2B is a non-limiting diagram showing an example biometric monitoring system according to an embodiment.

The system 200, according to an embodiment of the invention shown in FIG. 2B, may use a secure socket to maintain a persistent connection with all biometric wearable devices. This channel is used for pairing and other administrative functions. Library code 209 including the motion library may be provided to biometric monitoring cloud computing platform 204b for simplifying the construction and interpretation of the biomarker. This library 209, for example, could be implemented in a programming language, such as an object-oriented, high-level programming language with dynamic semantics like Python.

In one example preferred embodiment, the biometric components including biofeedback APIs, codec, and applet 208 may be implemented in a mobile phone hardware security chip separate execution environment that runs alongside the Rich Operating System and provides security services to that rich environment. The biometric components including biofeedback APIs, codec, and applet 208 may offer an execution space that provides a higher level of security than a Rich OS. In another example embodiment, the biometric components including biofeedback APIs, codec, and applet 208 may be implemented as a virtual machine.

The Wearable Manager 212 can be implemented as a service provided to end-users for managing biodata collections of wearables 205 interfacing with User Devices 150, 205 to generate analytics, recommendations, and modeling of the user's diagnostics, including mindset, recovery, nutrition, and movement assessments. Devices 150, 205 may be grouped into a single identity and used to backup and endorse each other. Wearables may be associated with each other to create a network of wearable devices. In some embodiments, the wearables may provide a collection of individual device public keys (as opposed to a new key). If there are not many shared devices in the environment, preferably the list of devices preferably may short because of the potential for increased computational and bandwidth resources may expended and introduce a time cost in order to encrypt a message with all of the public keys on a wearables list.

In one example embodiment, a wearable may be accessed using as a shared private key on top of the unique private key of the Device 150, 205. It should be noted however, it is not typical to share a "private key", nor would it be desirable to have a long-lived shared symmetric key.

One aspect of the biometric monitoring network 200 according to an embodiment of the invention enrolls a user device 150, 205 and equips it with a healthcare service provider's 204 keys. Inventive API's enable secure execution of a number of sensitive device-side transactions, including: getting a reliable and anonymous device id—on request, an embodiment of the invention may generate a signing key for a device. The public key is hashed into a string that can be used to identify and communicate with a device. The private key remains locked in the hardware and can only be applied on behalf of the service that requested the ID; getting a device to sign something—the private key of the device identity can be used to sign things proving that this particular device was involved. The signing ceremony is executed in secure hardware such that the key is never exposed to normal processing environment of the device; getting a device to encrypt something—an encryption key can be generated on request and applied to any blob of data. Encryption and decryption is triggered locally and takes place within the secure execution environment on the User Device 150, wearables 205 so as to protect the key; creating a biometrics account—the device can be asked to generate a new biometrics account using the random number generator (RNG) built into the User Device 150. Certain embodiments of the invention enable multiple wearable devices 205 to be bound into a ring so they can interchangeably present themselves to the healthcare service provider 210 on behalf of the user to generate analytics, recommendations, and modeling of the user's diagnostics, including mindset, recovery, nutrition, and movement assessments and programs.

A Healthcare Service Provider 204 (e.g. Healthcare Provider Website 204a) calls a Third-Party Agent/Process to create hardware keys in a user device 150, wearable 205. Different types of keys are available depending on the purpose, such as for crypto-coins or data encryption. Hardware keys are governed by simple usage rules established during creation. For example, a key may require that usage requests are signed by the Service Provider that created the key, or that the user confirms access through the device API 209 interfacing with its software library.

In one embodiment, the wearable 205 can be configured to only respond to an instruction from a Healthcare Service Provider 204a that has been "paired" with the Device 150. The Authentication Web Site 206 conducts the pairing ceremony as it is able to confirm the integrity and identity of both device and the service provider. When a device 150 is paired it acquires the public key of the Healthcare Service Provider 204a, while the Healthcare Service Provider 204 gets a uniquely generated identity and public key for the Device 150.

In this embodiment, while the Third-Party Agent/Process supports local calls, ideally all instructions are signed by the Healthcare Service Provider 204. This protects a device key from being applied by a rogue application. An Encoder 210 is provided to help prepare and sign device instructions on the application server so that analytics, recommendations, and modeling of the user's diagnostics, including mindset, recovery, nutrition, and movement assessments, can be made in a way that ensures the user's privacy and data protection.

In one embodiment, the wearable biometric components including biofeedback APIs, codec, and applet 208 are deployed into a TEE, which implements the applet 208 as dedicated hardware device, and preserves the integrity of the user's biometric data. Execution and data collection are cryptographically isolated from any other function of the host. In an embodiment, a native API is provided that translates calls 209 into a secure environment to present a uniform interface to biometric software components 208.

Biometric Privacy Attestation

Embodiments of the invention provide biometric data collection integrity attestation by automating the assurance of the user's privacy integrity against a known state as a signatory on a block chain transaction. The system implemented by an embodiment of the invention is comprised of the several components shown in FIG. 2C. A Device Adapter 220 is a software service running on an endpoint device that provides an interface to the Healthcare Service Provider 204 application and integrates with the wearables 205. Another component, the Device Registrar 221 is a service that registers a user device 150 into the block chain 222. A block chain 222 is used both to store device registration and attributes and to execute mindset assessment, recovery, nutrition, and movement assessments. There may be different block chains. Another supporting component is a Healthcare Service Provider 204 which is the application seeking to conduct assessments by collecting biometric data from the wearables 205 with the device 150.

Figure 2C:
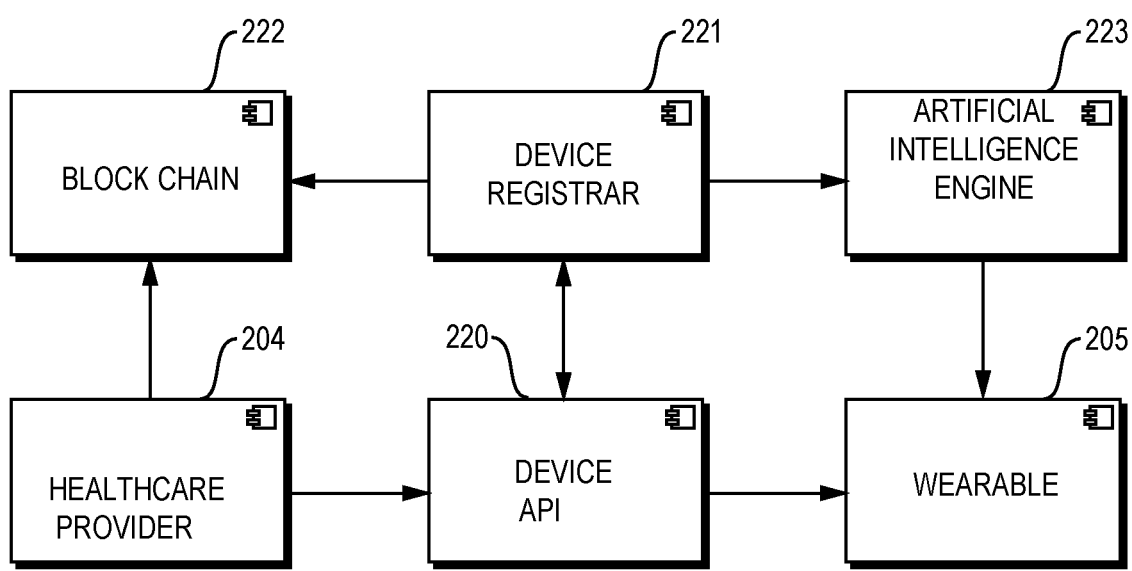
FIG. 2C is a non-limiting diagram of the components of an embodiment.

According to an embodiment of the invention, when the Device Registrar 221 shown in FIG. 2C software runs for the first time it may ask the wearables 205 or the device 150 to generate a public/private key pair. The public key is signed by an endorsement key established during device manufacturing. This signed public key is sent to the Device Registrar 221 and validated. Registration may involve confirmation from the device operator. Registration may involve endorsement at the point of sale in the presence of a clerk. The Registrar may ask the device for a biometric data collected from the wearables 205 so the mindset assessment, recovery assessment, nutrition assessment, and movement assessment can be generated. It is further signed by the Registrar. The resulting data set becomes the gold reference or Reference Value for future integrity checks. Confirmation from the device operator may be required in collecting the gold reference or Reference Value. This data set is posted into a public cryptographic ledger. The public record established cryptographic proof of the time of registration along with the endorsement of the registrar. The registration may further include attribute data, such as location or company name or device make/model. The registration may reference a signed document that sets out the policy terms of the registrar at the time of registration. The Device Registrar 221, or another trusted integrity server, creates a block chain account key (a public/private key pair) that can be referenced as a signatory in a multi-signature transaction on the block chain. A signatory the value represented in the block chain transaction cannot be spent or transferred unless co-signed by the Registrar.

To sign a transaction the integrity server expects at least one recent measurement from one or more the wearables 205. This measurement may be requested directly of the Device Adaptor or fetched by the server through a persistent sockets connection with the device. The current measurement is compared against the gold measurement or Reference Value in the block chain. If the measurements match the transaction is signed. If the measurements match but the recent measurement is older than a specified time window, the request is rejected. If the measurements do not match, the request is rejected. If there is a rejection, the transaction may have been prepared with another manual signatory that can be asked to override the rejection. If the measurements do not match, the wearable may be put through a registration renewal where a new measurement is gathered because it is possible that a different user is using the wearable and therefore the readings/measurements may not be accurate. Every time a measurement matches, the device registration record can be updated with a success count. The integrity server may be given policy rules that may accept a reading/measurement which doesn't match the predicted range of measurements/readings from the wearables in light of other matching measurements or attributes or previous readings. The system 200 may generate an alert if the readings/wearables are predicted to be matching but suggestive of a health issue of the user.

A system, according to an embodiment of the invention, may be implemented with a collection of trusted wearables 205 rather than an integrity server to do the work of matching measurements and signing the transaction. The system may compare and try to match biometric measurements directly with a plurality of biofeedback from a multitude of wearables 205 associated with the user to determine if the biometric measurements during assessment processing using features built into a smart block chain contracts such as that of Ethereum.

Attestation Authentication Web Site

In an example embodiment, Authentication Web Site 206 may be a JSON API written in Python, which uses the Service Provider 204 private key to enroll the identity keys of User Devices 150 and Wearables 205. During enrollment, the public key of the User Device 150 or Service Provider 204 is recorded or processed through one or more of Biometric components including biofeedback APIs, codec, and applet 208. Enrollment enables the Biometric components including biofeedback APIs, codec, and applet 208 to pair a wearable device 205 with a Service Provider 204. The result of pairing is that a User Device 205 has a service public key, endorsed by a Third-Party Agent/Process and can therefore respond to Service Provider 204 instructions.

The Protocol according to an embodiment of the invention specifies the structure of an instruction and the signing/encryption that is applied for the wearable 205 or the user device 150 to accept the instruction. The instruction itself may, for instance, be prepared as a C structure that contains the instruction code, version data and payload. The entire structure preferably is signed by the service provider key and delivered to the device biometric/biofeedback components/apps/APIs 208 by calling a device local command.

Preferably, every User Device 150 and wearable 205 should present unique identity credentials. Devices may join a ring so as to act as a singular entity. In one embodiment, a User Device 150 and wearable 205 can support group ID's that are locally stored as a list, but publicly translate into cross-platform authentication. The wearable Adapter 214 may be configured as the interface between the Biometric components including biofeedback APIs, codec, and applet 208 bolted into the Device 150 and wearable 205 and the outside world of partner apps and online services. In implementation, it can manifest in one or more diverse forms, which would be at least partially dictated by the basic capabilities across devices, hardware support and OS architecture.

Authentication System Adaptor

Figure 2D:
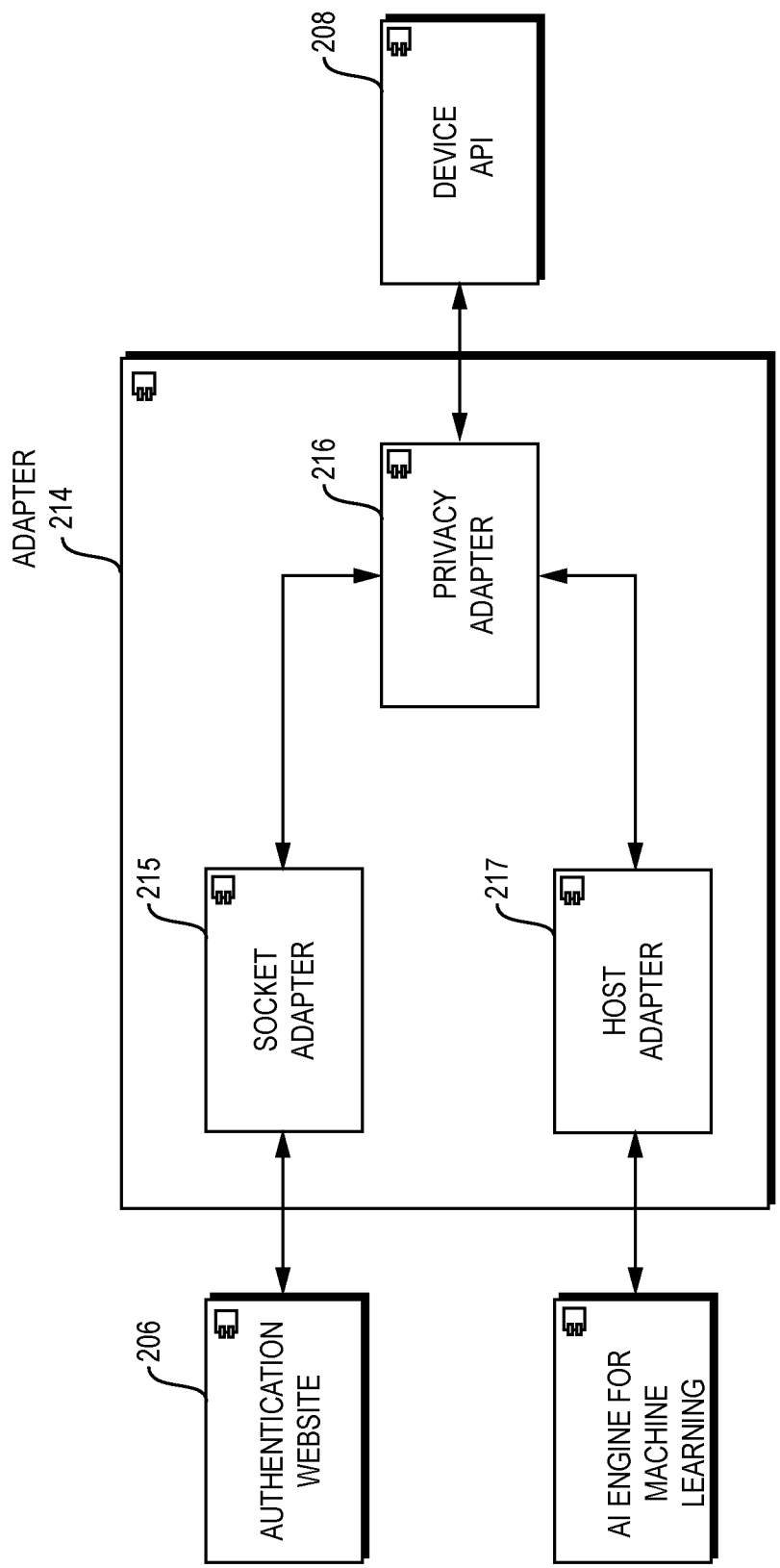
FIG. 2D is a non-limiting diagram of the biometric adaptor and its outward and inward-looking interfaces.

The Authentication System Biometric Adaptor 214 is composed of outward and inward-looking interfaces as shown in FIG. 2D. The inward-looking interface, the Privacy Adapter 216, handles proprietary communications with the Device 150 and wearable 205. The Host Adaptor 217 is provided to expose services to healthcare provider system 204. The Host Adaptor 217 presents the interface of the Authentication System Authentication System Biometric 214 through different local contexts, such as browsers or system services. Multiple realizations for diverse contexts are anticipated though initially this may be an Android service and a windows com process. The Socket Adaptor 215 connects the client environment Authentication Web Site 206. The Privacy Adaptor 216 component is the proprietary glue that pipes commands into the Device 150 and wearable 205. In an Android implementation the Authentication System Biometric Adaptor 214 may manifest as an Android NDK service app and may be configured to launch at boot. The Authentication System Biometric Adaptor 214 prepares message buffers that are piped to the Device 150 and wearable 205 and then synchronously awaits notification of a response event. The Host Adaptor 217 is primarily there to isolate the Privacy Adapter 216 from the host environment. In some cases, there may be limited assurance that the client has not been compromised. The Host Adaptor's role is therefore primarily to facilitate easy access to the Device 150 and wearable 205. The host adaptor can interface with AI Engine to execute the artificial intelligence based video processing system to process video from the user device to create movement models.

Instructions from the Healthcare Service Provider System 204 intended for the Biometric components including biofeedback APIs, codec, and applet 208 may be signed by the Healthcare Service Provider System 204 and then passed through to the Privacy Adapter 216 and Device 150 and wearable 205.

Healthcare Service Provider System Registered to a User Device

According to an example embodiment, the Authentication Web Site 206 is the first service provider registered to a Device 205. The Authentication Web Site 206 has the special capability of being able to pair additional service providers with that Device 150. Communications with the Authentication Web Site 206 may be handled through the web API and should be authenticated. In one example, this is implemented with an API key. In a preferred example embodiment, this is implemented using an SSL key swap. In some embodiments, all requests may be signed.

The relationship with devices may be dependent on being able to sign instructions with the private key. Such a private key is highly sensitive and is protected. Preferably, the private key is encased in an HSM.

In some embodiments, multiple keys are used, such that if one is compromised the whole system is not lost. This should, for example, should make it more difficult for an attacker to know which devices are connected with a compromised key. Furthermore, the system 200 is preferably in near constant contact with all Devices 205 through the Socket Adapter 215 shown in FIG. 2C, which can facilitate frequent rotation of the keys.

The Authentication Web Site 206 may comprise several sub-components. A Device ID is the unique identifier, in a UUID, assigned to a device by the Authentication Web Site 206 or other Registration Agent. An ephemeral pointer, Device Pointer, may be provided to a device 150 that can be requested by any local application. The Device Pointer can identify a current socket session to the Authentication Web Site 206 and therefore can be used to establish a device communication channel and to look up the permanent identifier, the Device ID. The root of a device registration includes a unique, anonymous identifier, a registration date, a public key paired to a private key held in the device hardware and an endorsement signature from the Registration Agent. This information is recorded in the Device Registration Record. The privacy adaptor 221 embodies the binding between the physical and digital works.

Protocol for Processing Instructions

The counterpart to the Device 150 and wearable 205 is the Encoder 210. The Encoder 210 prepares a command to be executed by a specific device which is signed and/or encrypted by the Service Provider 204. The Healthcare Service Provider 204 public keys are preloaded into the device during a pairing process conducted by Authentication Web Site 206. This allows the Device 150 and wearable 205 to validate the origin of the request, and if needed decrypt the contents of the instruction.

Figure 3A:
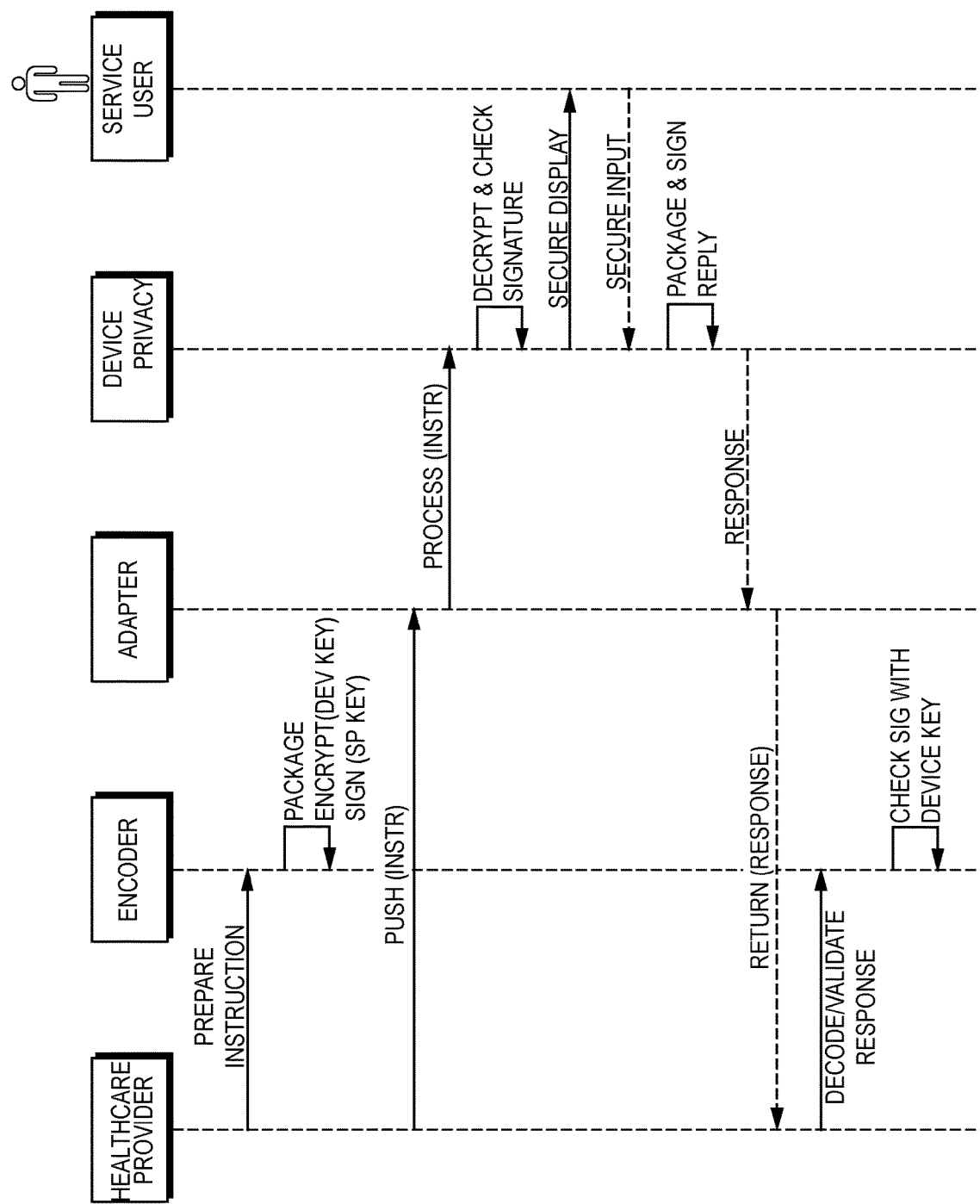
FIG. 3A is a non-limiting diagram of the sequence of packaging and delivering an instruction by the encoder.

The sequence of packaging and delivering an instruction is shown in FIG. 3A. The Healthcare Service Provider 204 generates an Instruction Record with the help of the Encoder 210 libraries. The instruction includes the type, the target device and payload. The instruction may be encoded with the device key and must be signed by the service provider key. The device key is fetched from the Authentication Web Site 206, or directly from the block chain, by looking up the Device Registration Record.

Protocol for Enrolling the User Device

Figure 3B:
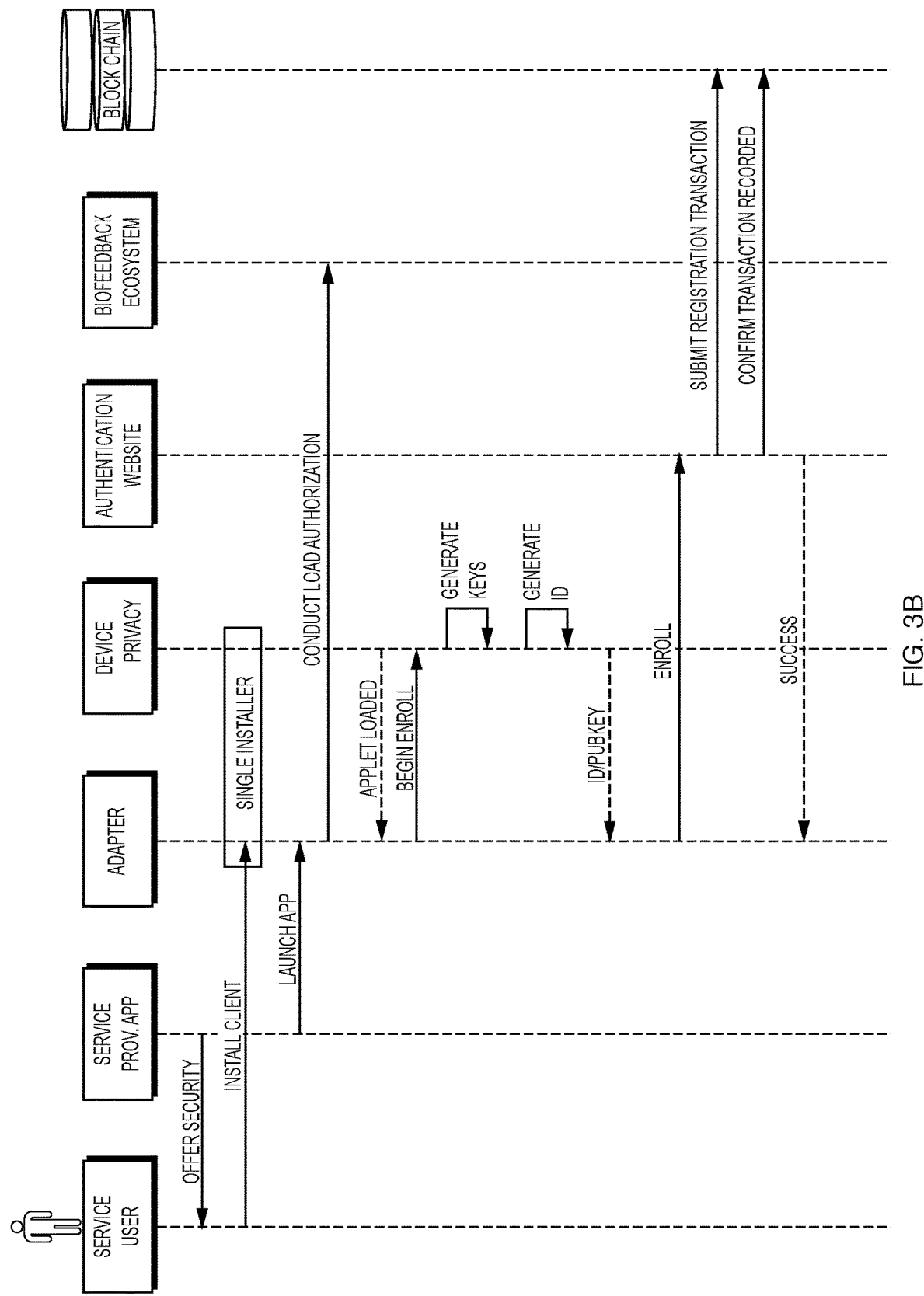
FIG. 3B is a non-limiting diagram of the biometric enrollment process according to an embodiment of the invention.

In one embodiment, device enrollment for a Device 150 and wearable 205 is on the block chain is essential to example embodiments of the invention. The enrollment process, shown in FIG. 3B, must be hassle free or even transparent to the user. Ideally, a fully reputable Device ID would include personalization of the relationship between a device and a user with a PIN or other memory test; as well as legal binding between the user and the device, for example, by registering the device in presence of a sales clerk. It would look up the endorsement keys of the OEM that manufactured the device to ensure provenance. It also might include training on the purpose, power and anonymity of device registration. It can be created with just creating the ID transparently. Because of this variability in the context of the registration, the Registration Agent should record the context of enrollment to ensure that trust is being extended where it's due. For example, testing an OEM endorsement key makes it vastly more certain that the Device Rivet is operating in a trusted environment.

Example Biometric Monitoring Network Components

Figure 4:
FIGS. 4 (4A-4V), 5 (5A-5J), 6 (6A-6E), 7 (7A-7R) are diagrams showing example components of the biometric monitoring network 200.
Figure 4A:
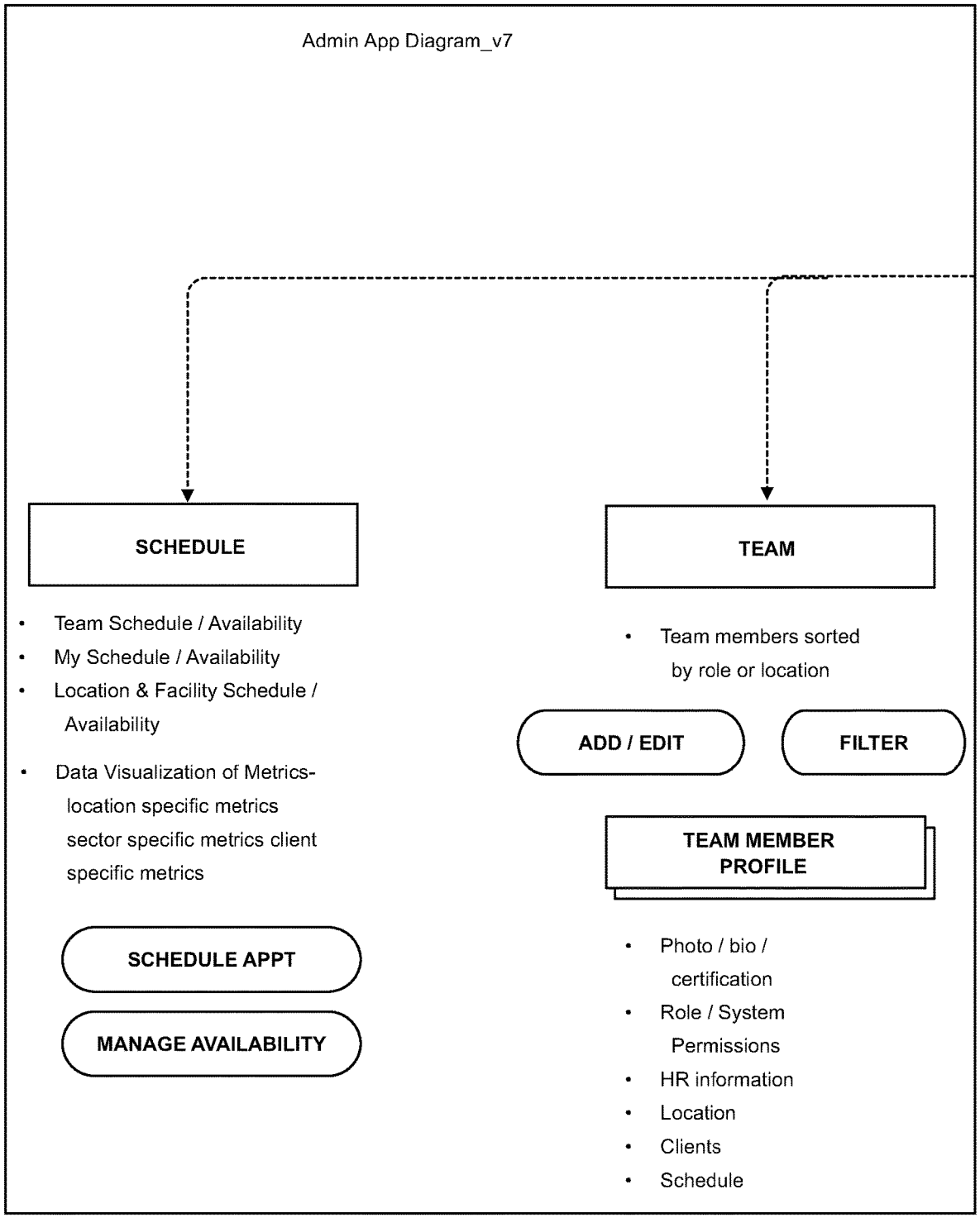
Figure 4B:
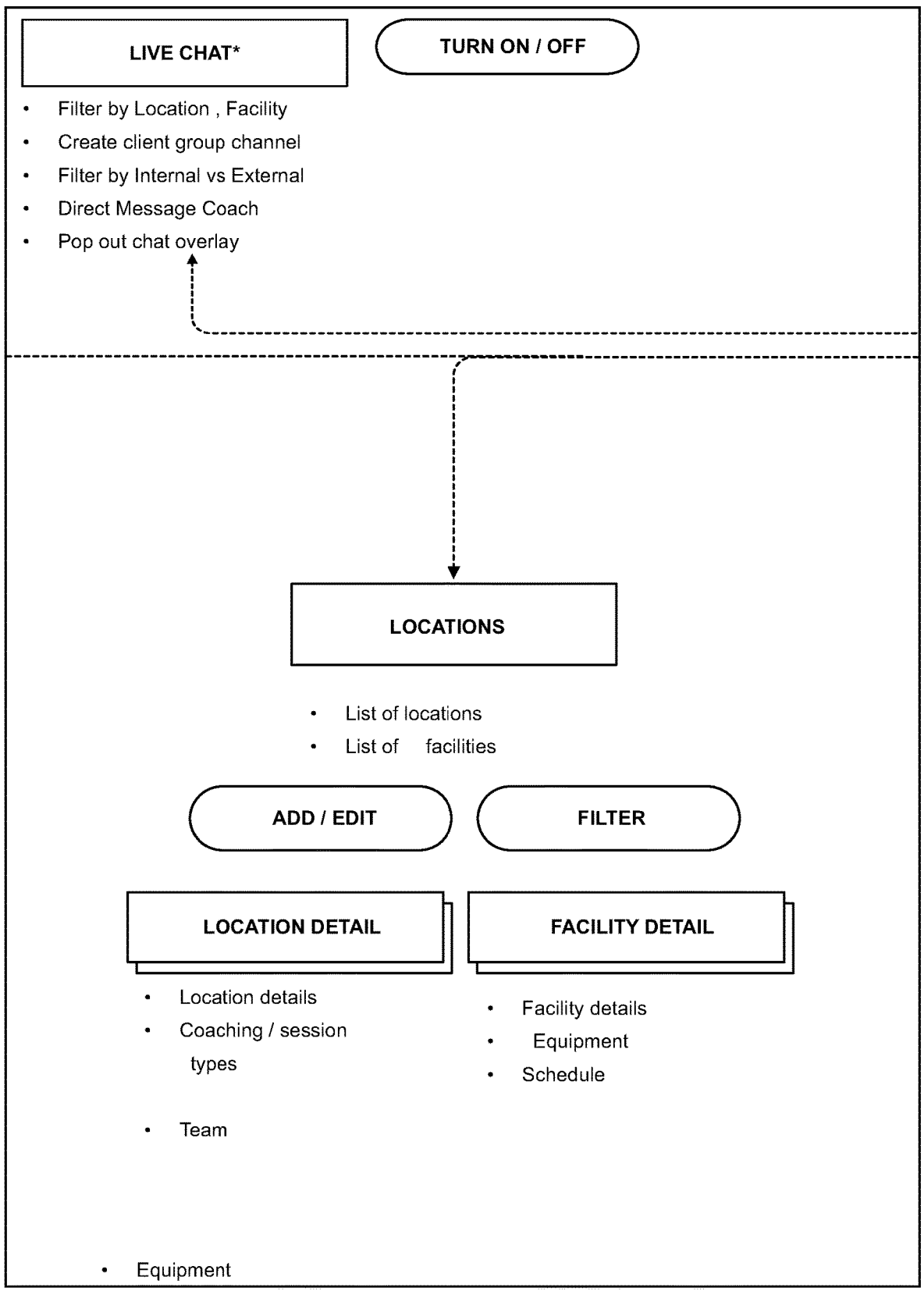
Figure 4C:
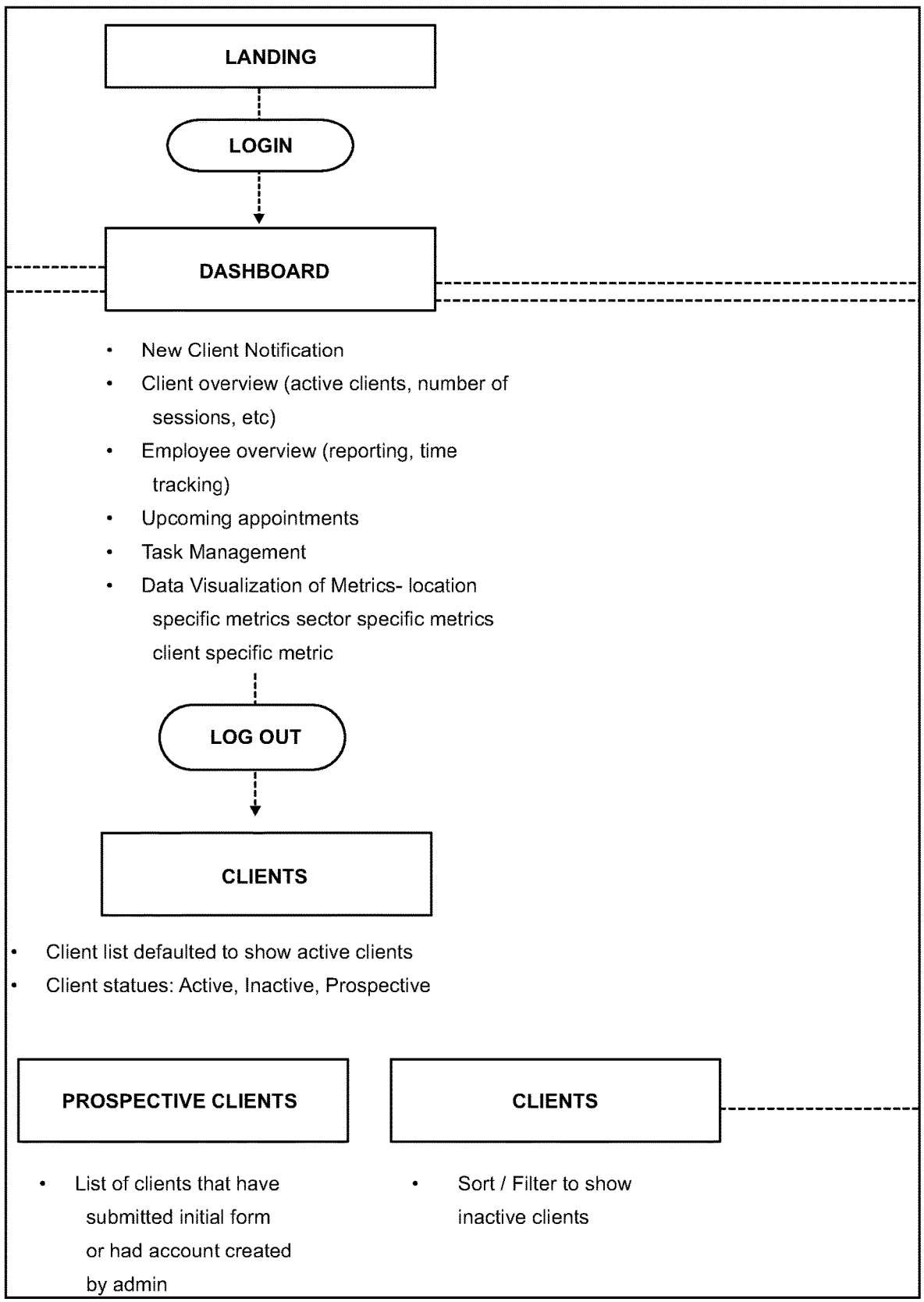
Figure 4D:
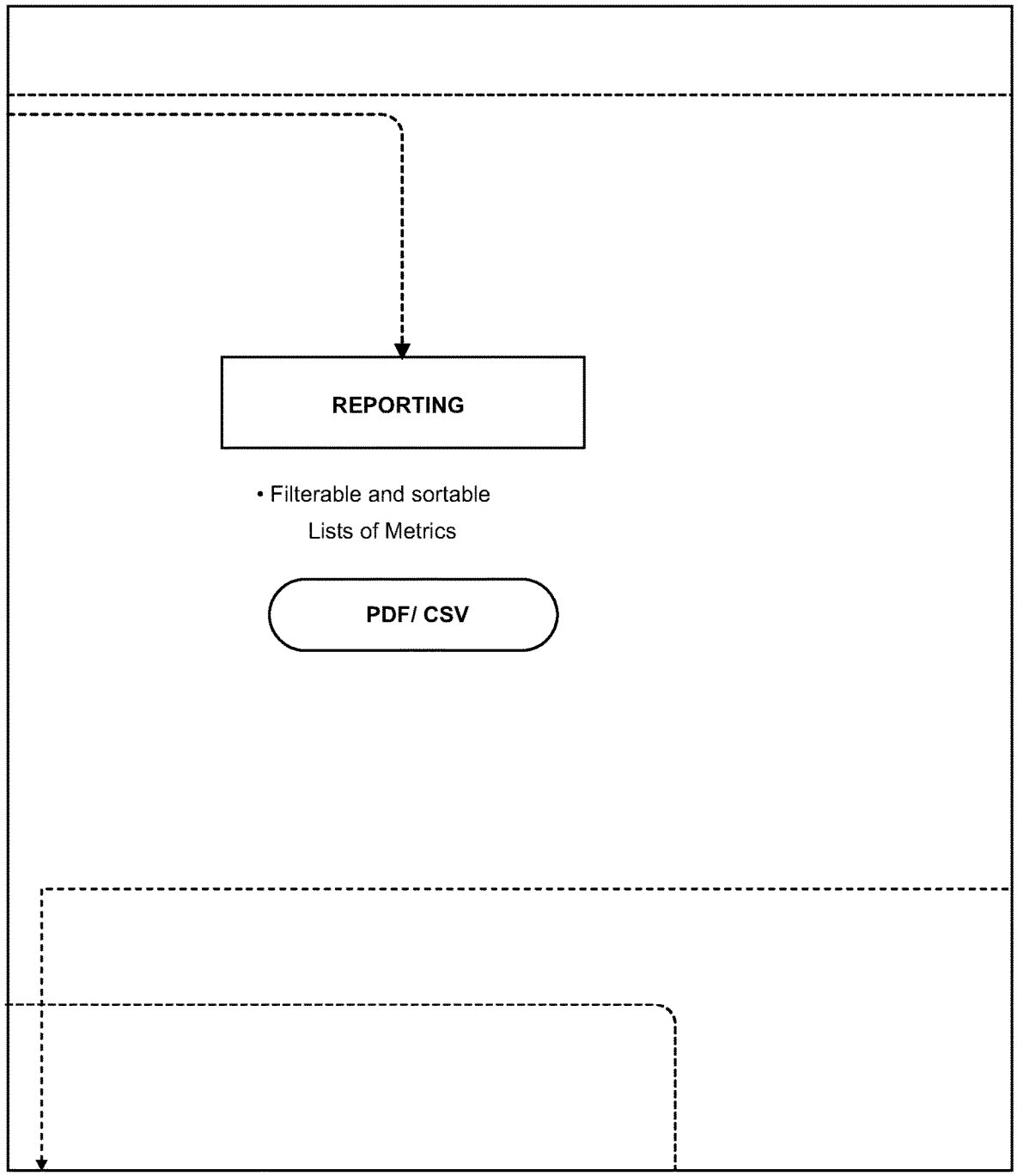
Figure 4E:
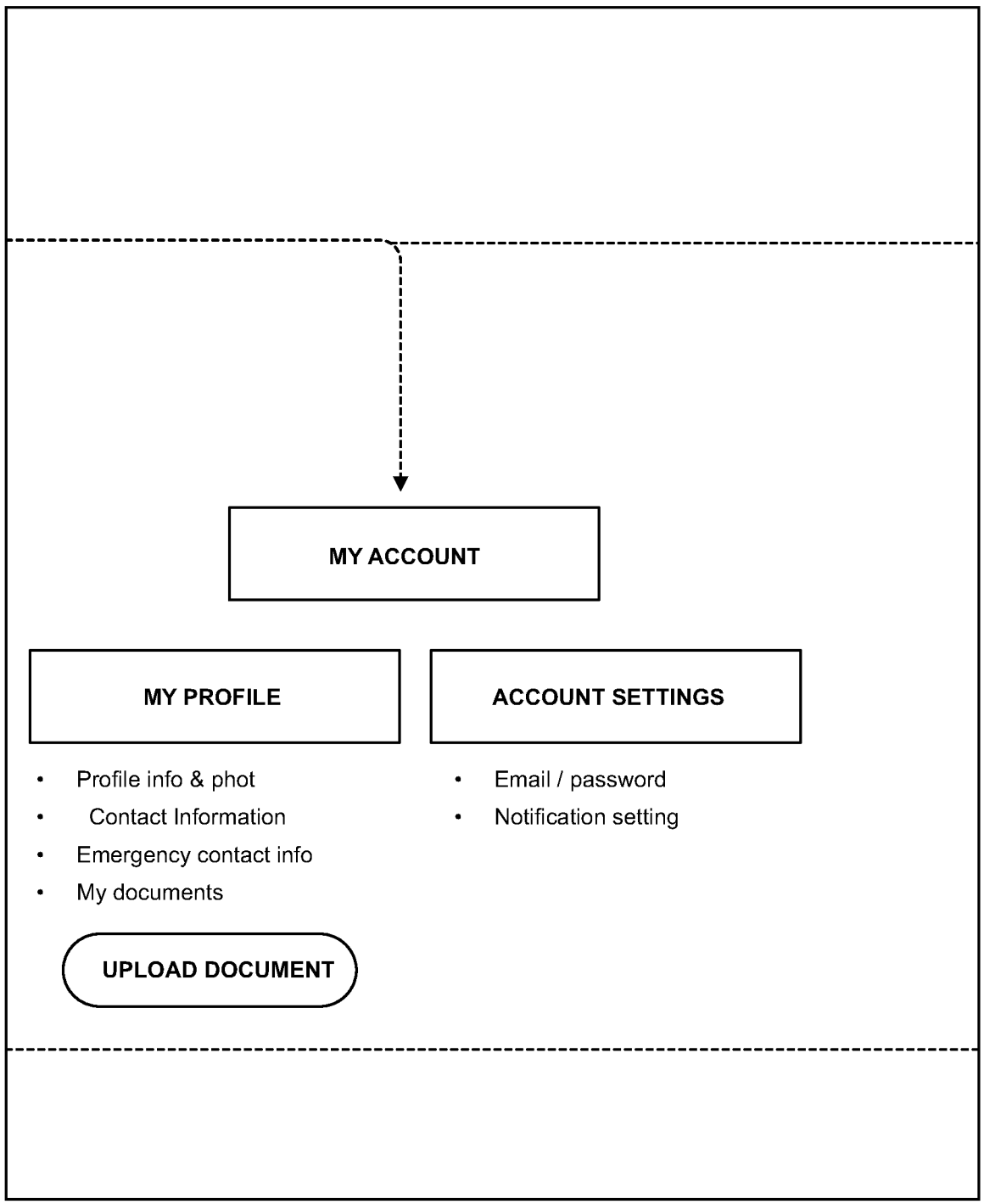
Figure 4F:
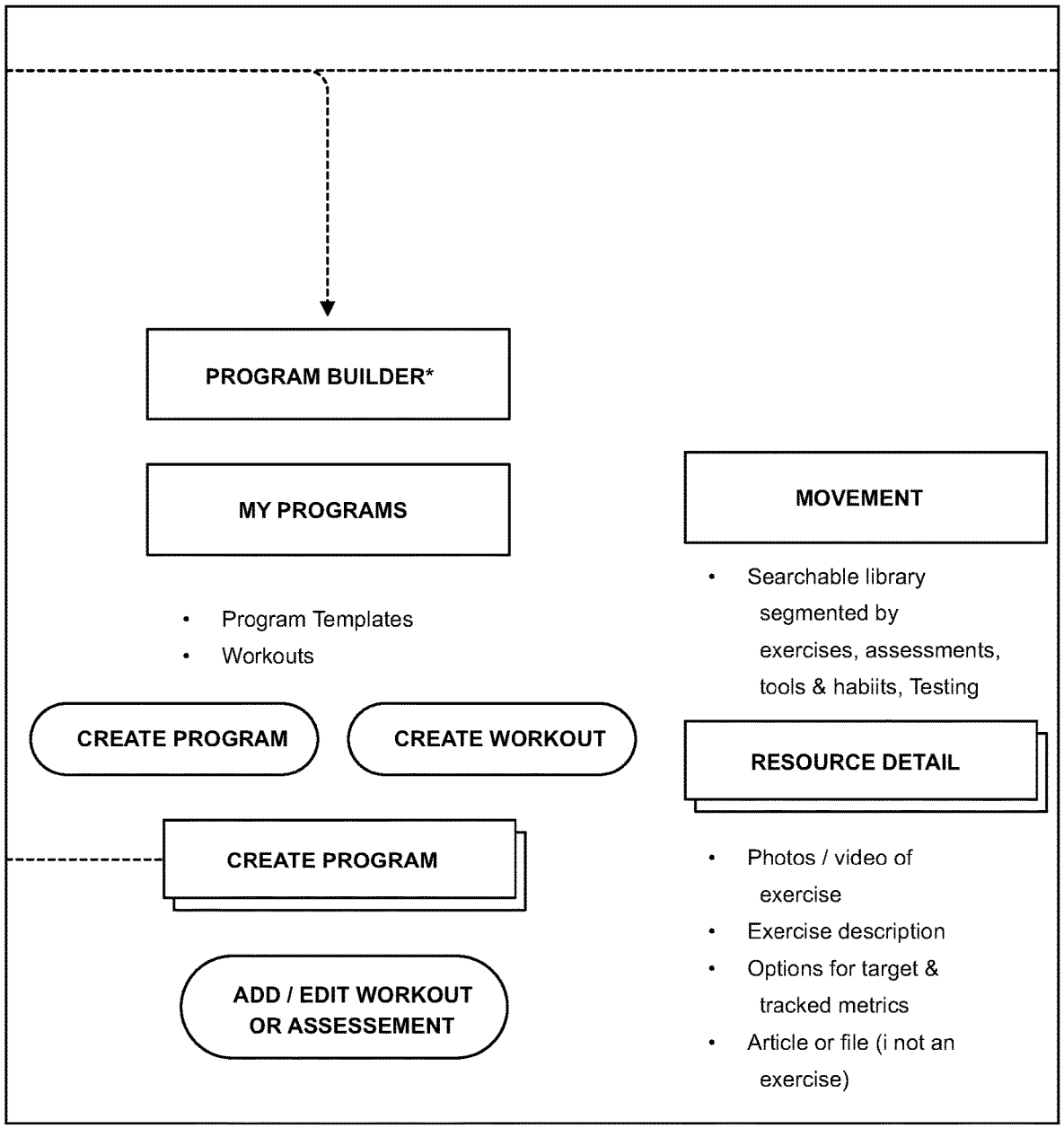
Figure 4G:
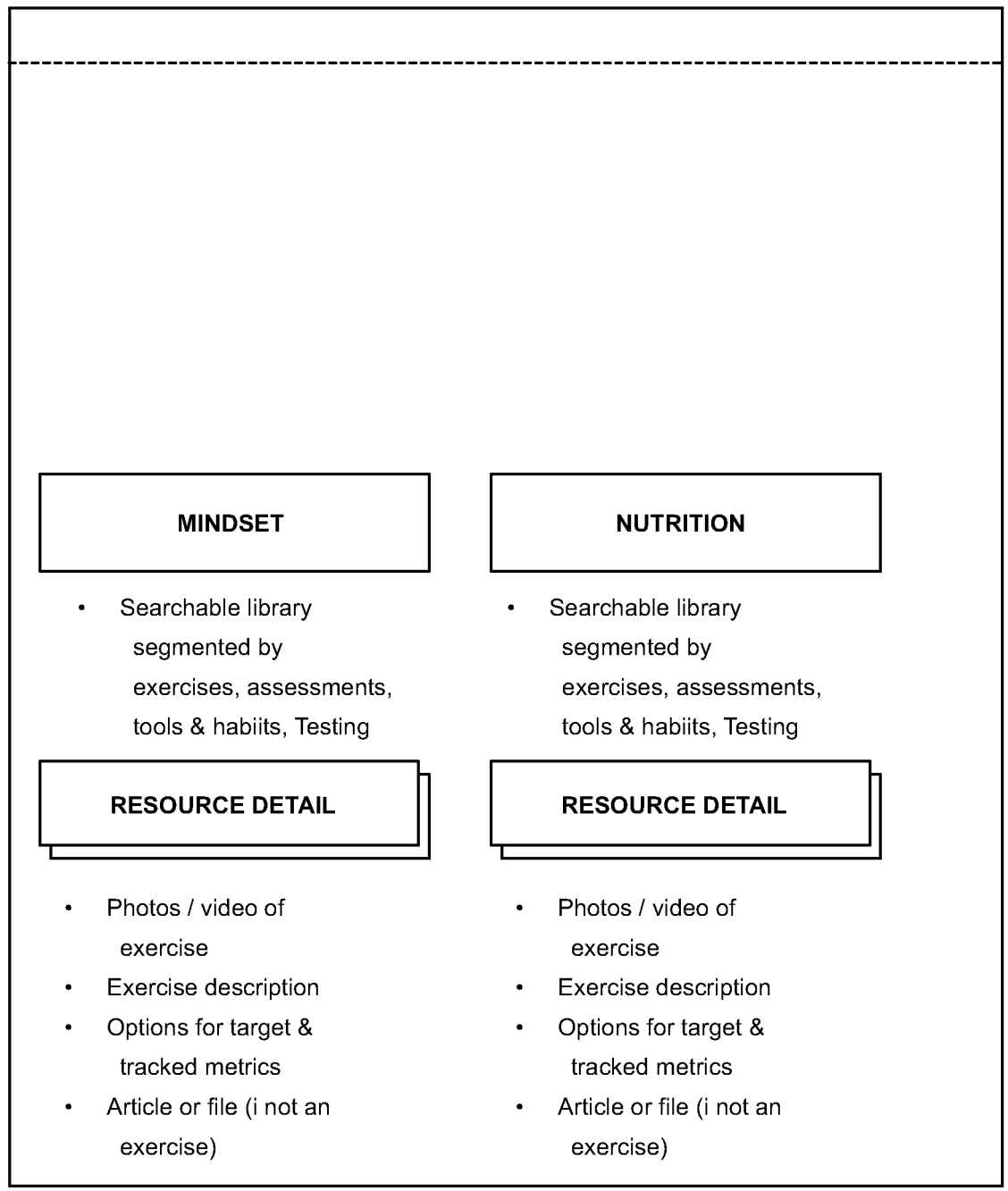
Figure 4H:
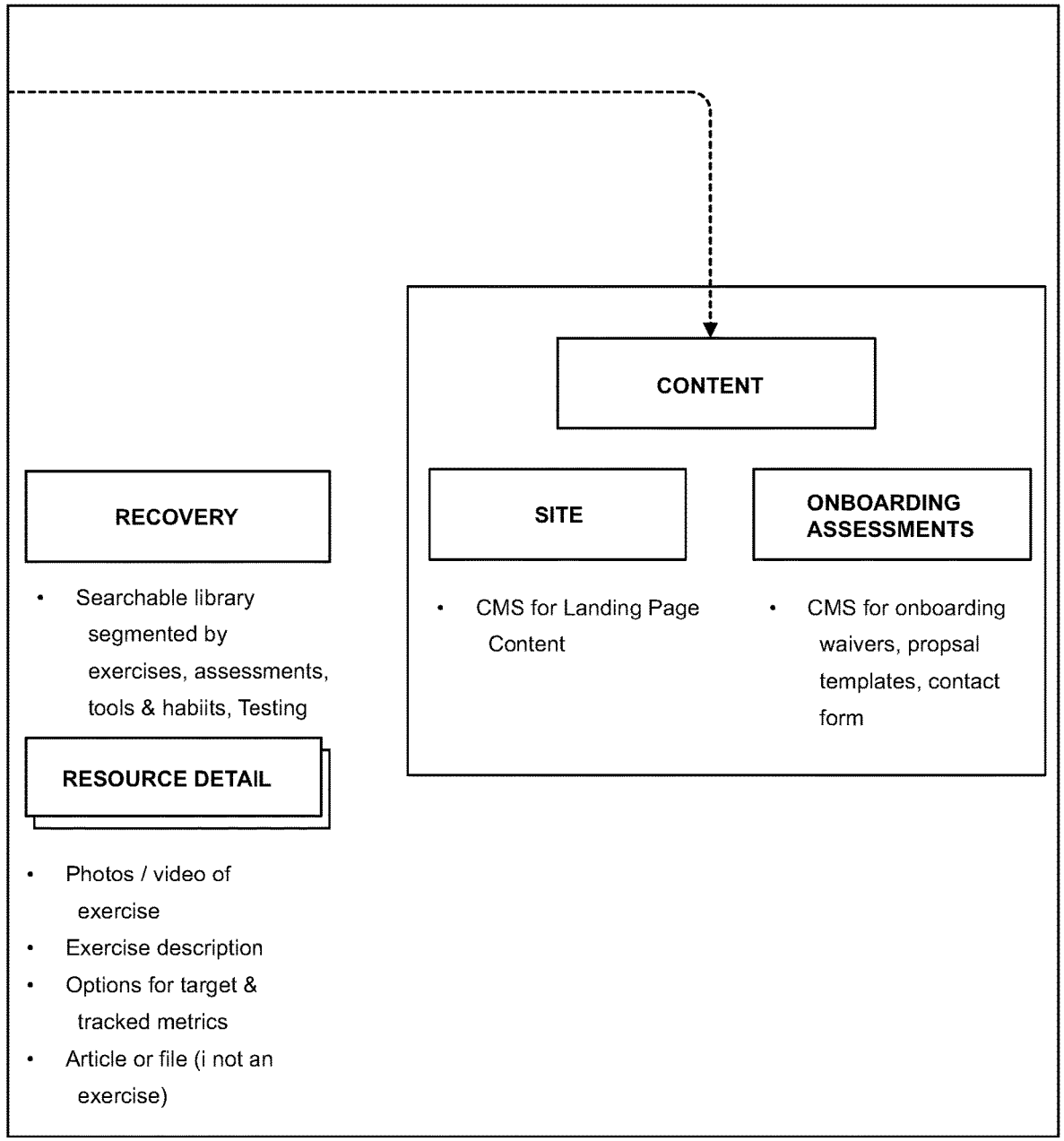
Figure 4I:
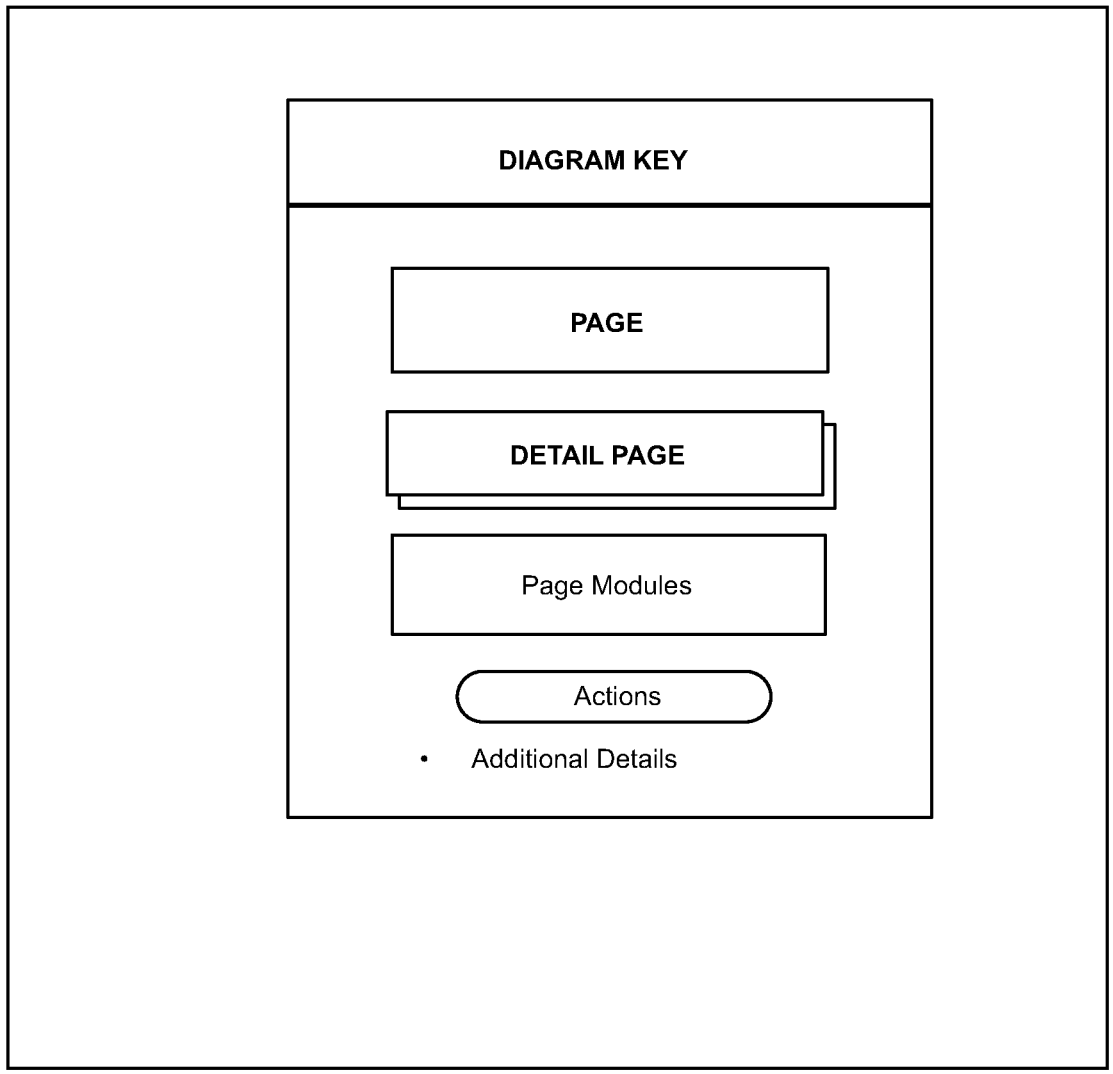
Figure 4J:
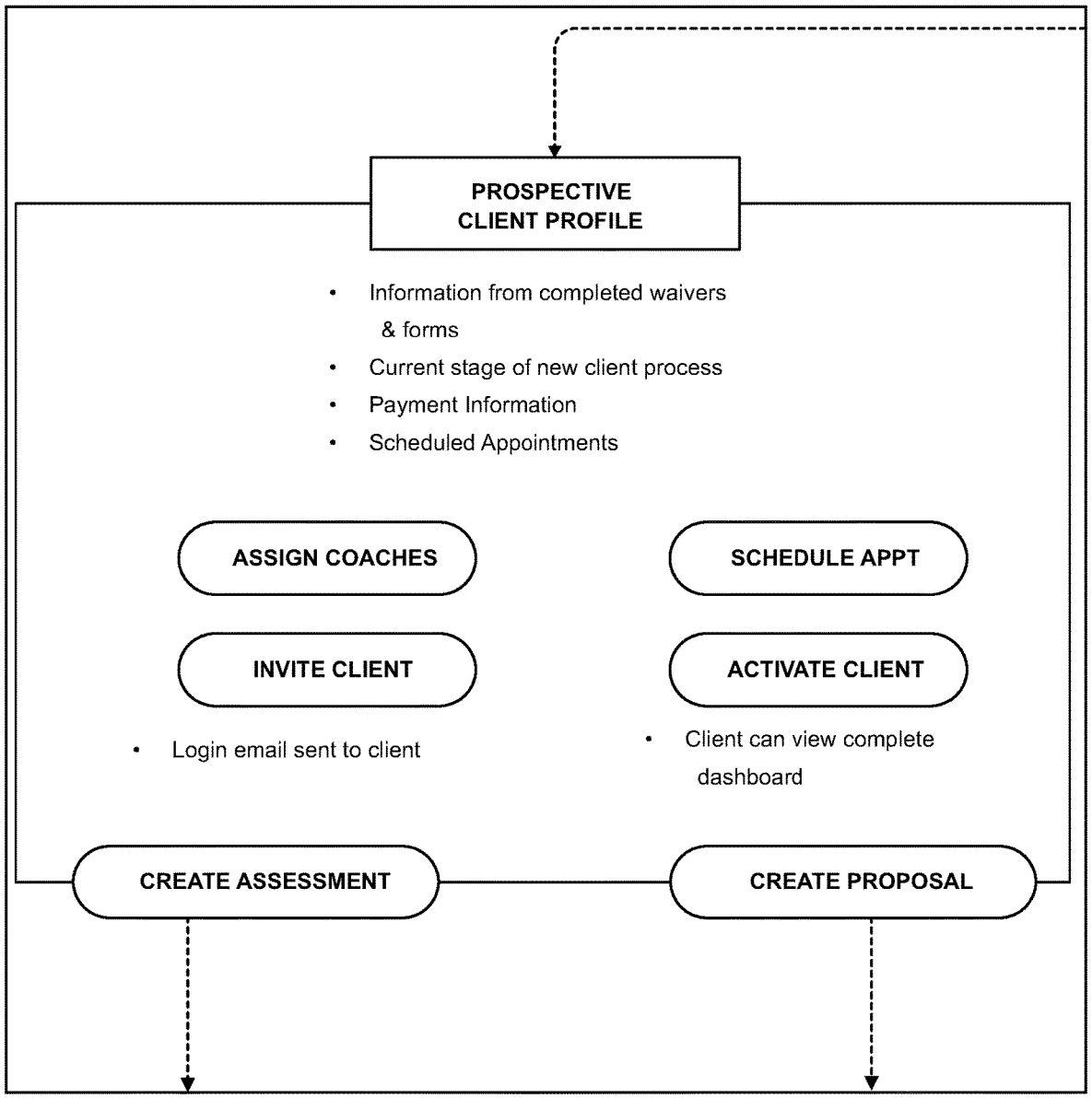
Figure 4K:
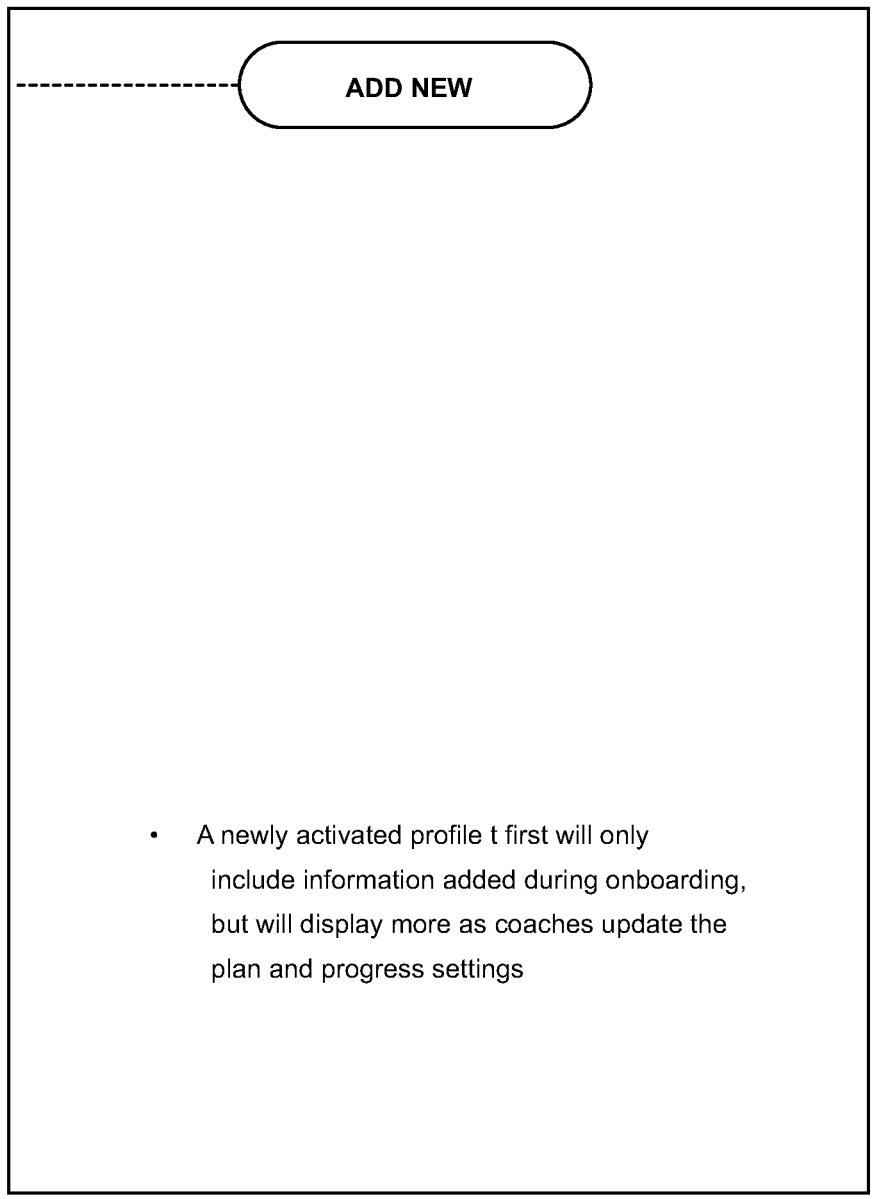
Figure 4L:
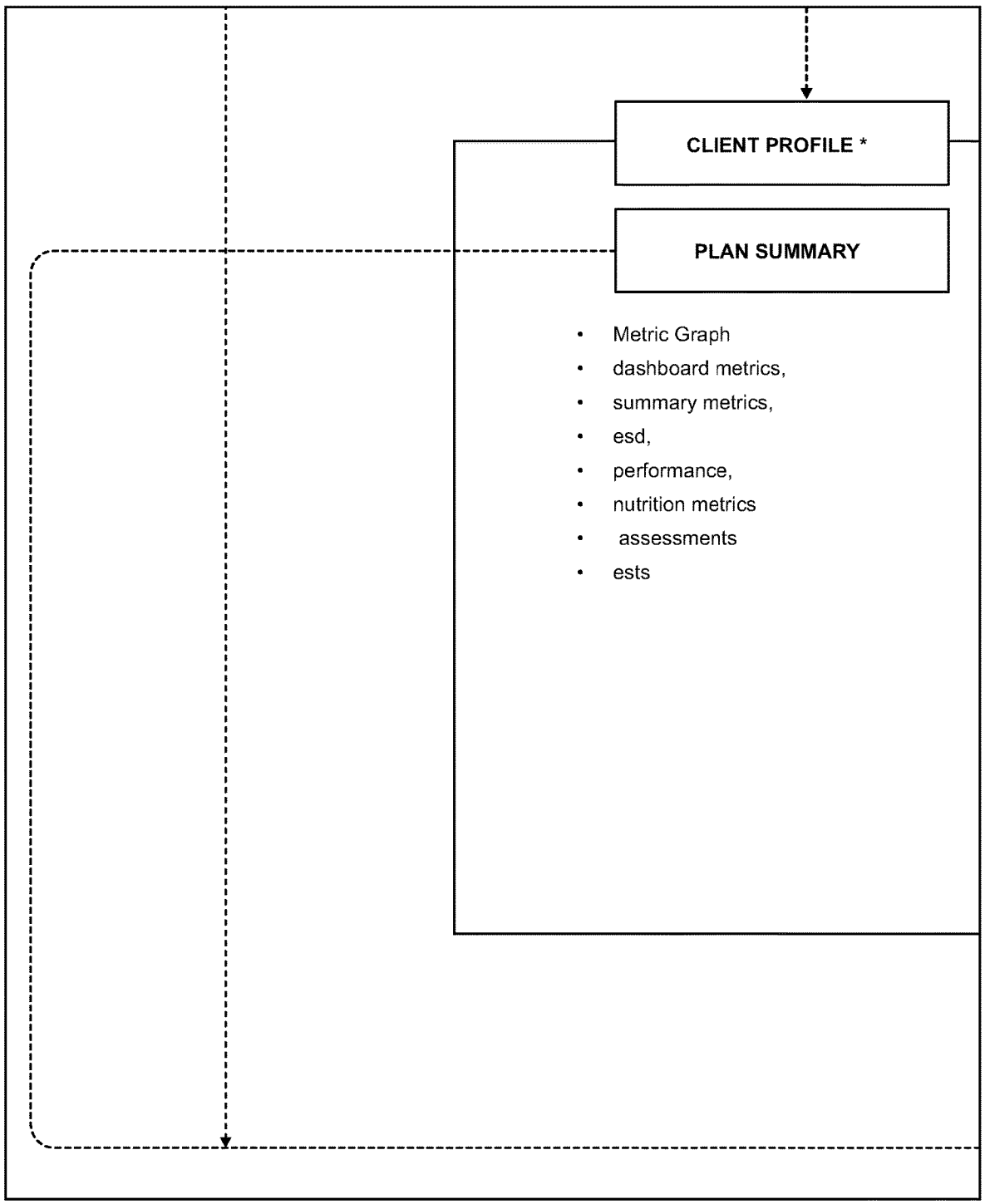
Figure 4M:
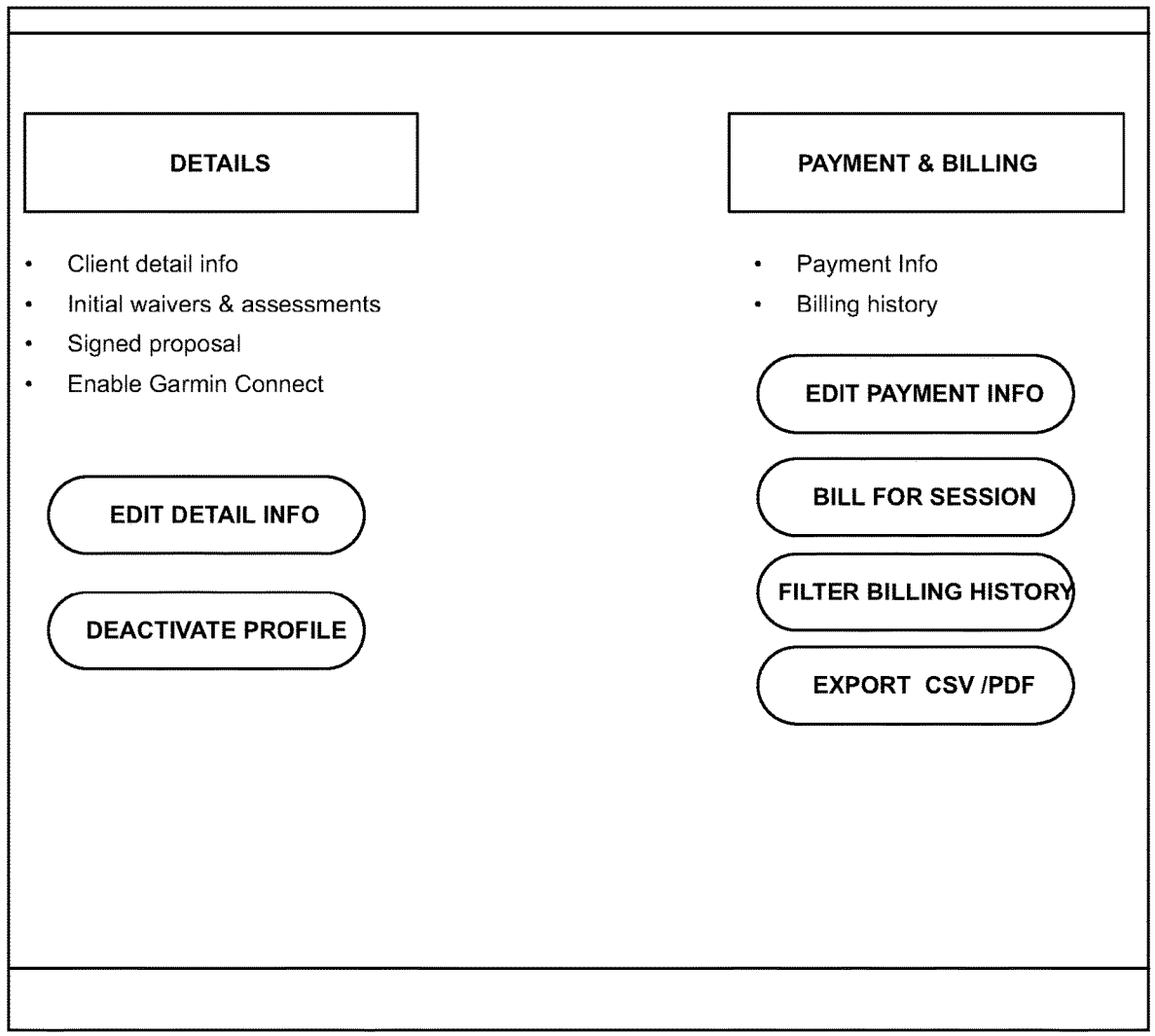
Figure 4N:
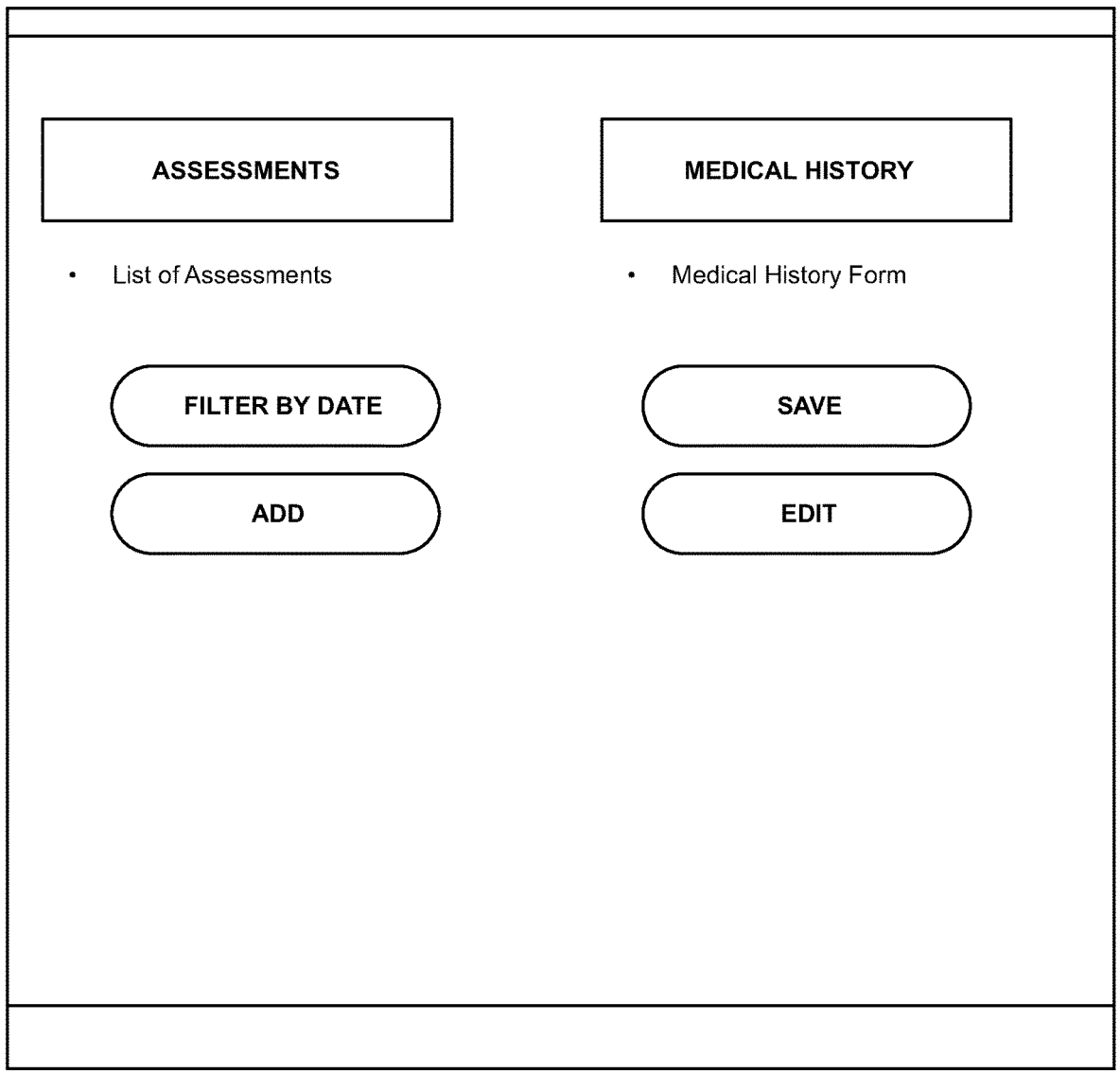
Figure 4O:
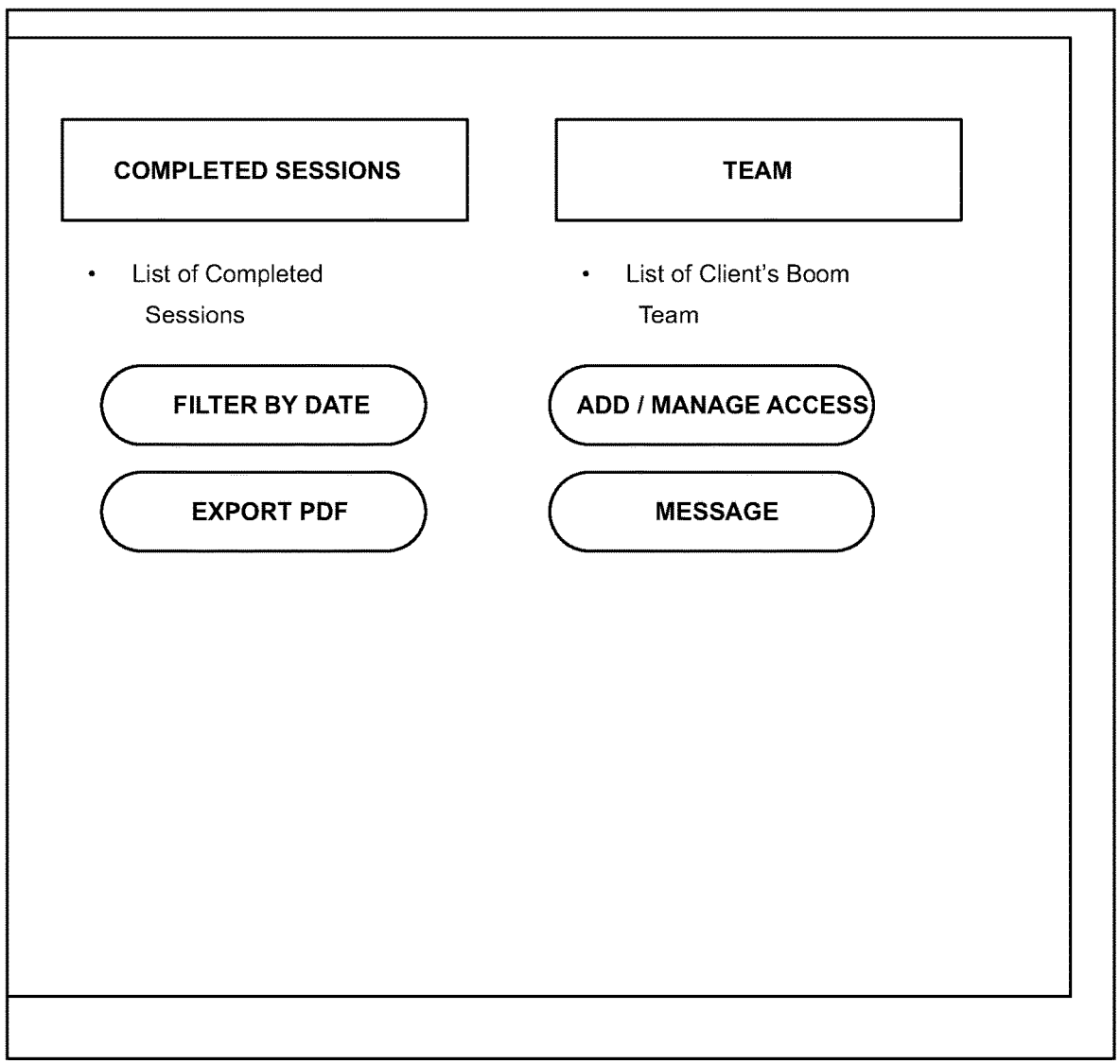

FIGS. 1, 4 (4A-1V), 5 (5A-2J), 6 (6A-3E), 7 (4A-4R) are diagrams showing example components of the biometric monitoring network 200. For example, in FIG. 4A, admin components at the healthcare provider system 204, 160, include a scheduler system that include location and facility scheduling components that provide geofencing, and modeling metrics associated with the location coupled with client specific metrics. In 4B, a communication interface is provided that enables live communications and video conferencing.

Figure 4P:
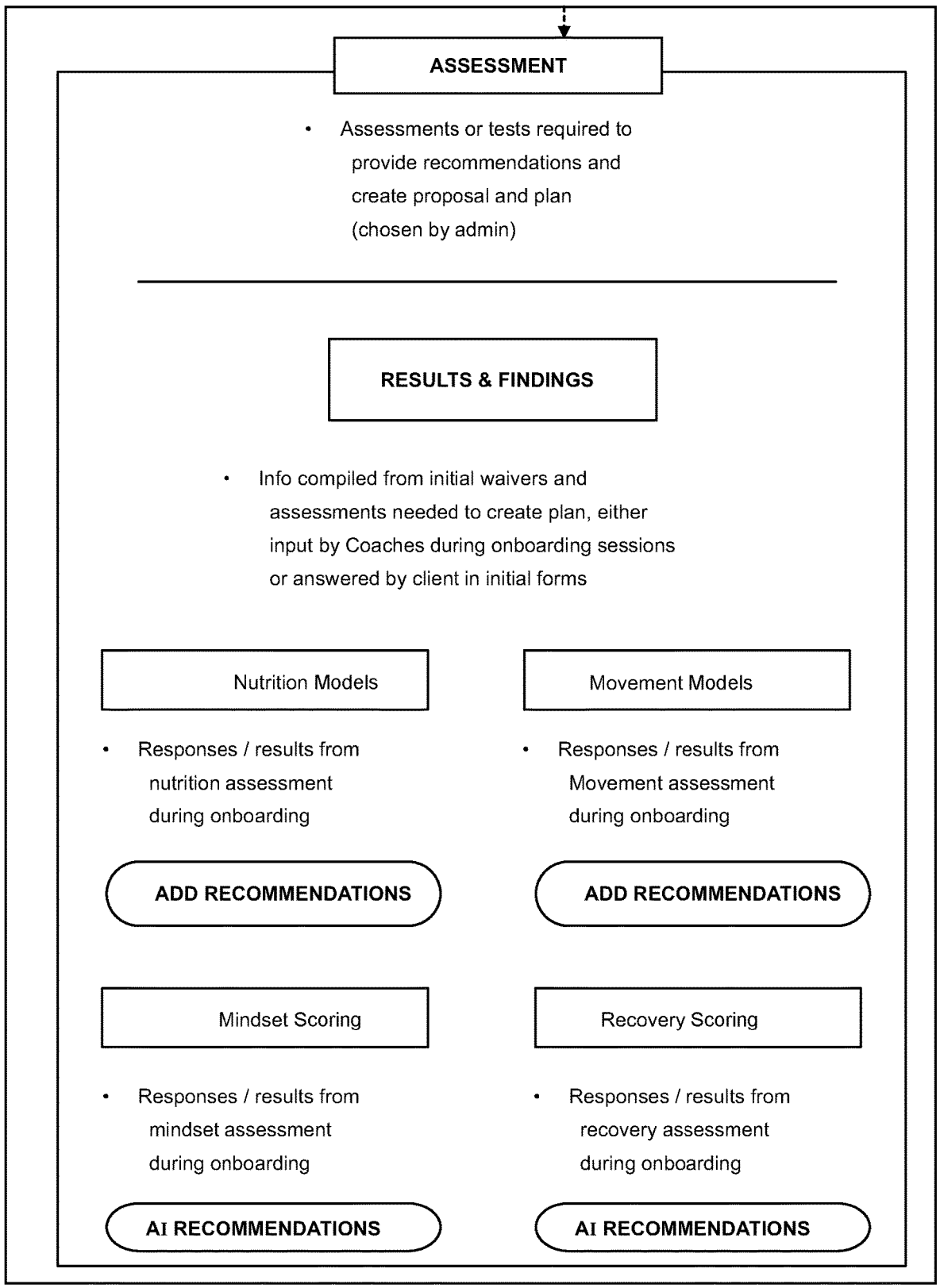
Figure 4Q:
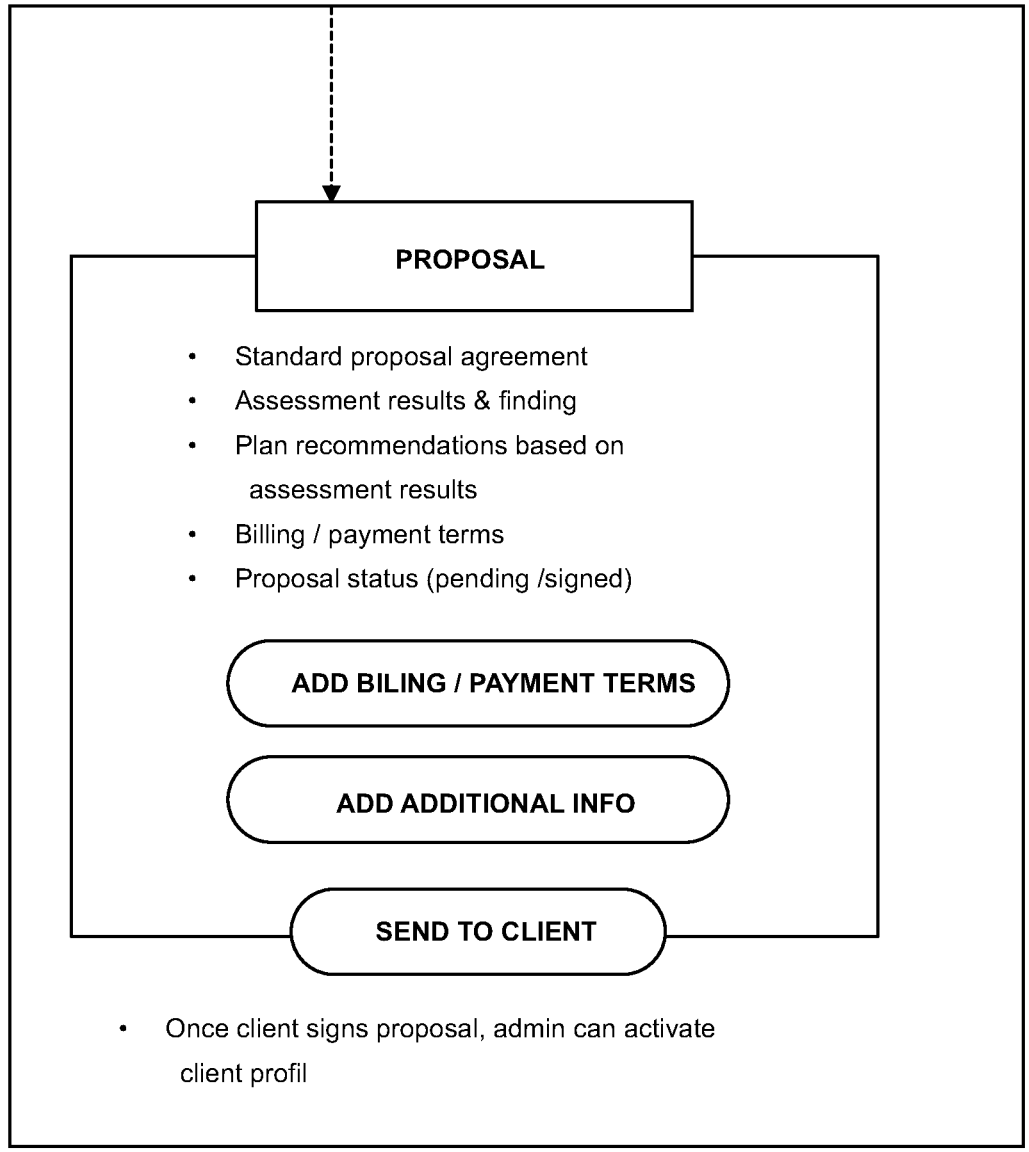
Figure 4R:
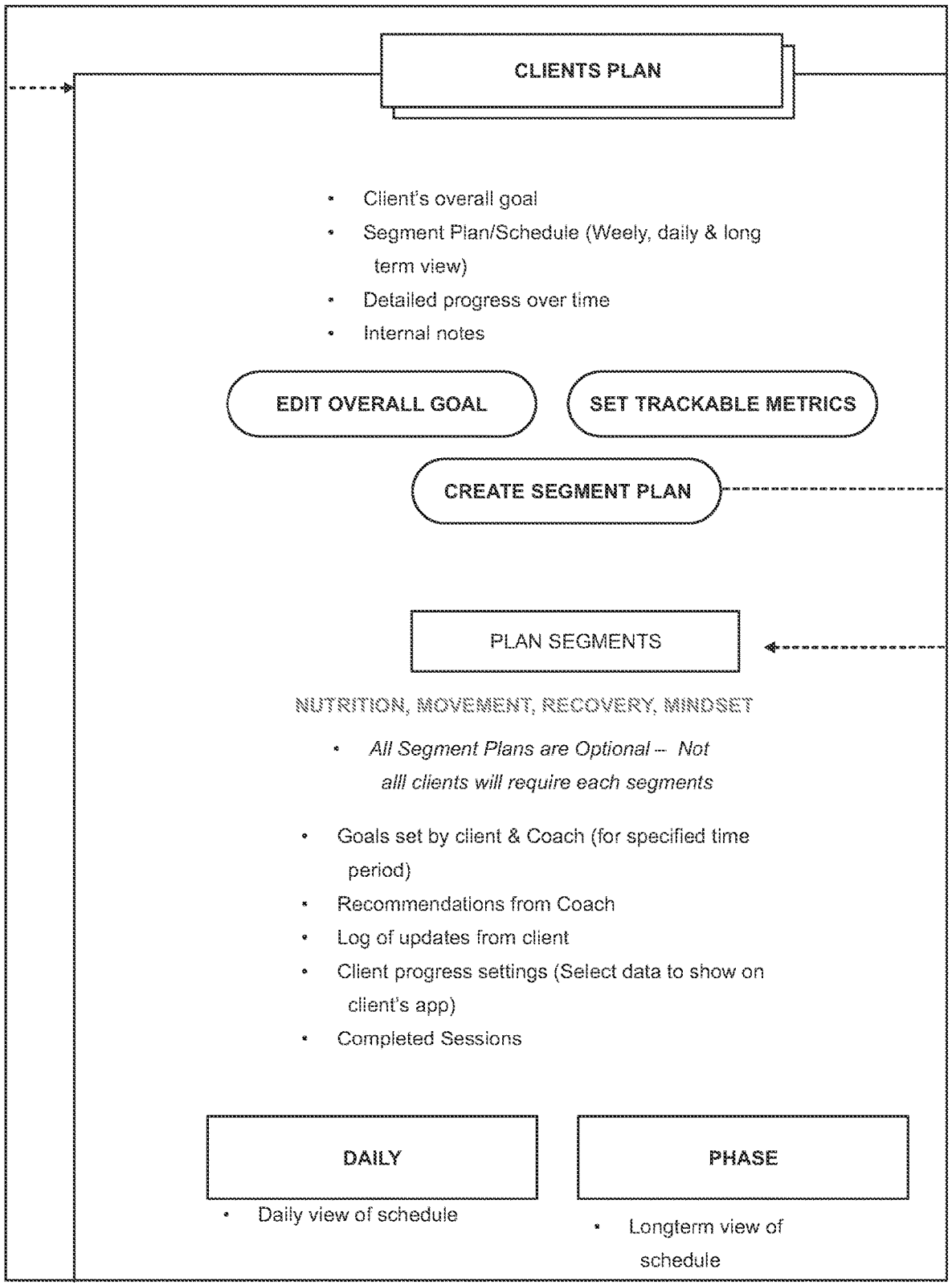
Figure 4S:
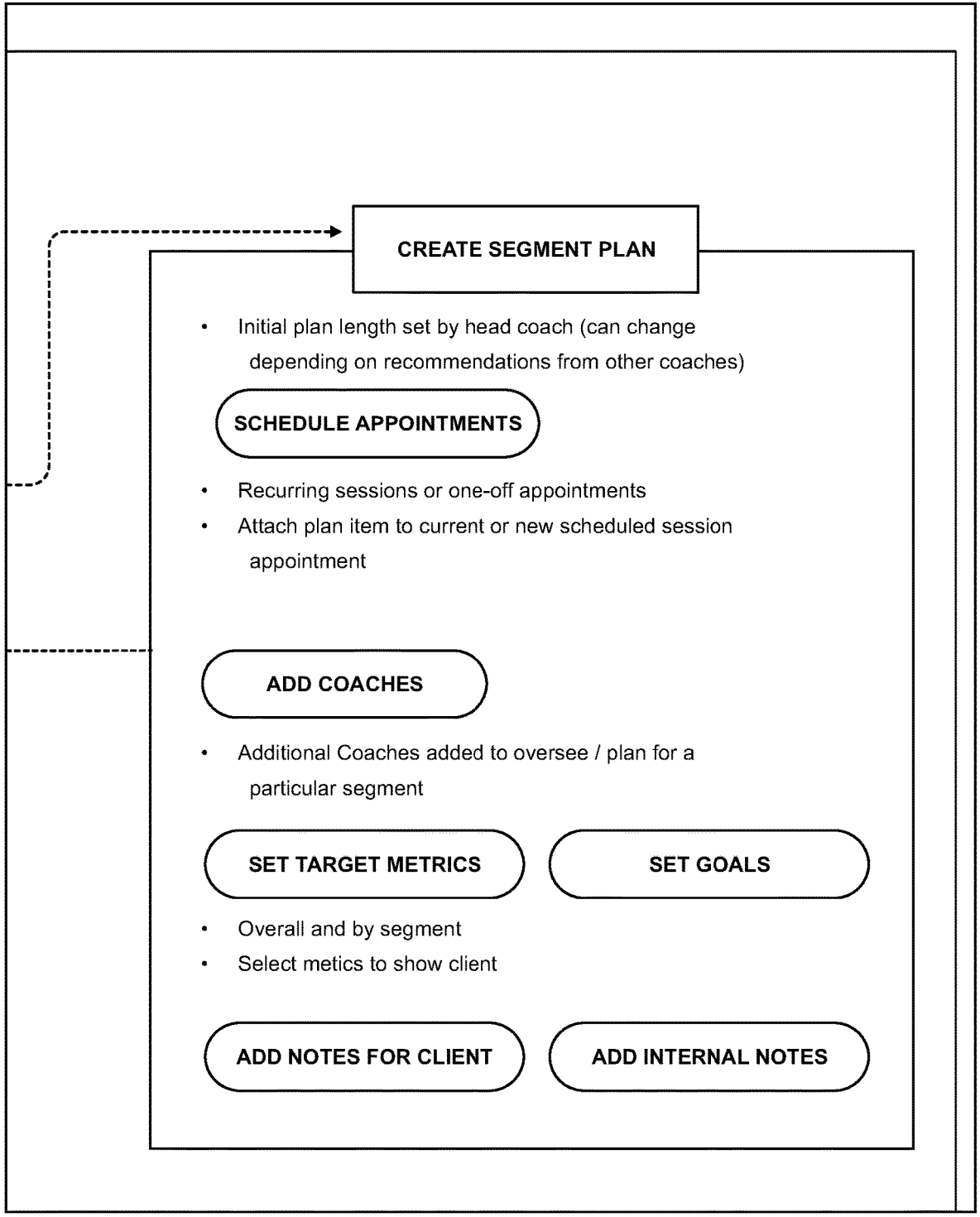
Figure 4T:
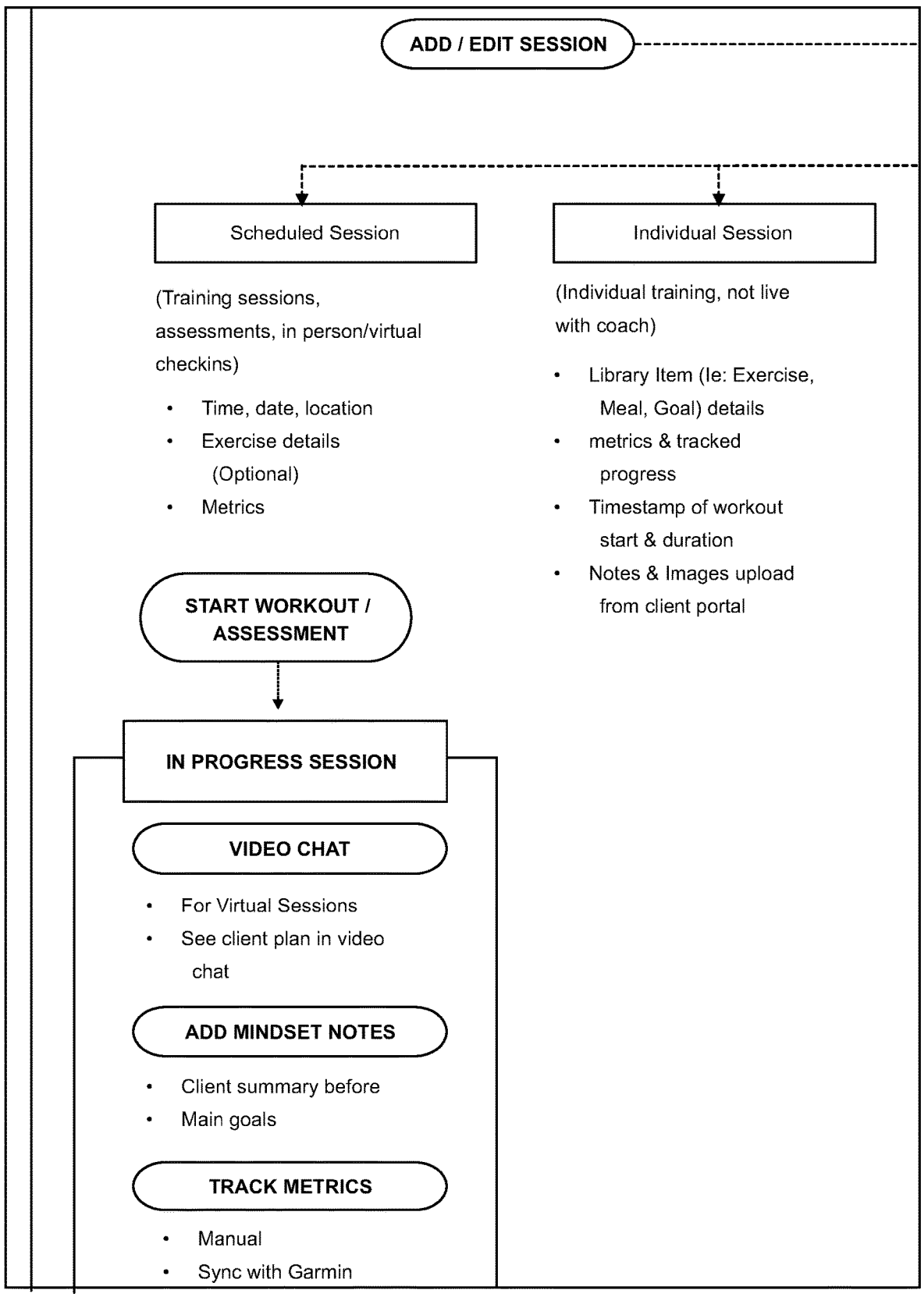
Figure 4U:
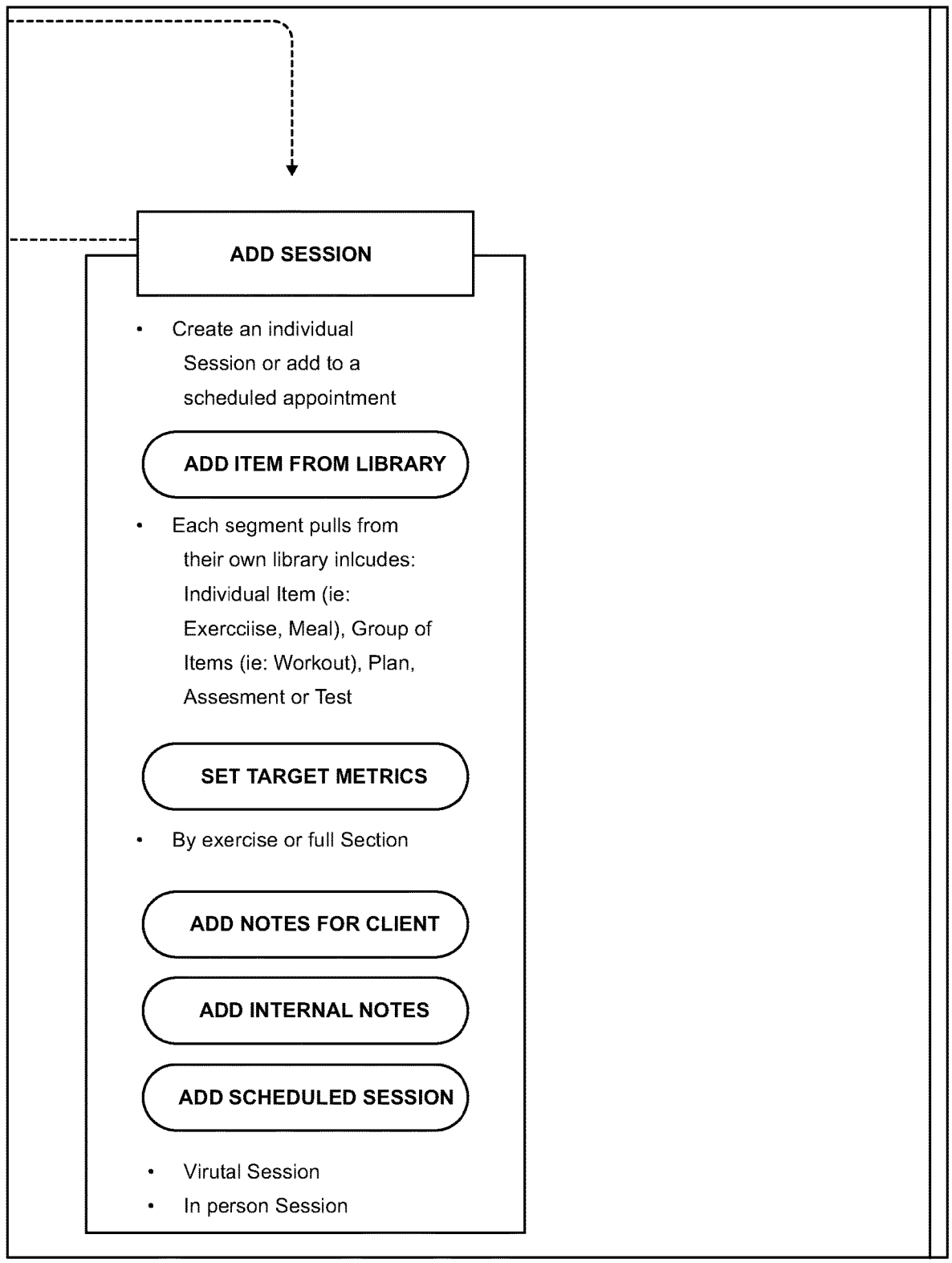
Figure 4V:
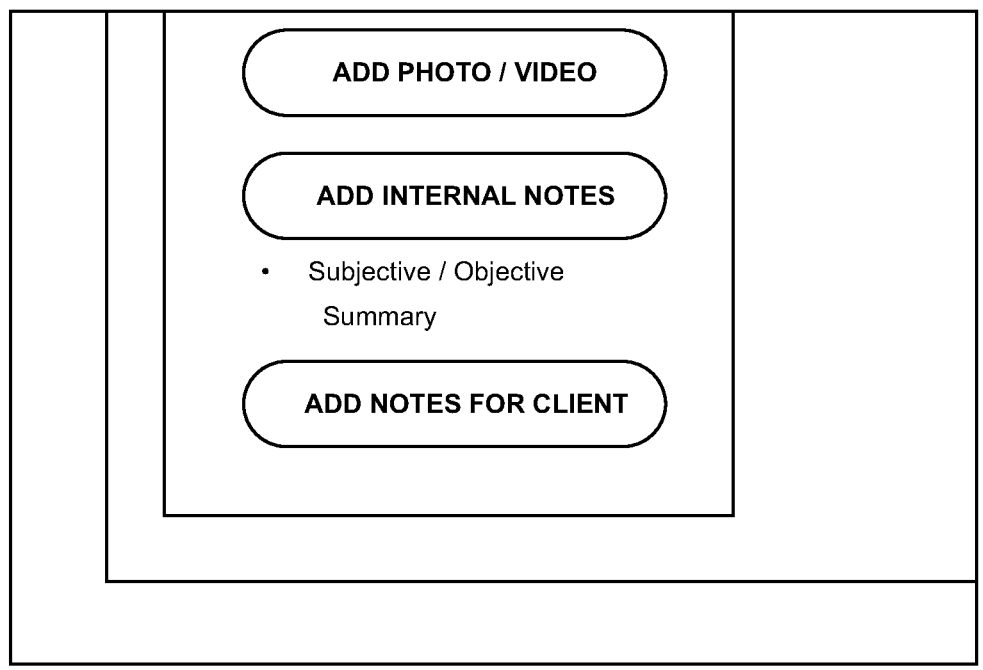
Figure 5:
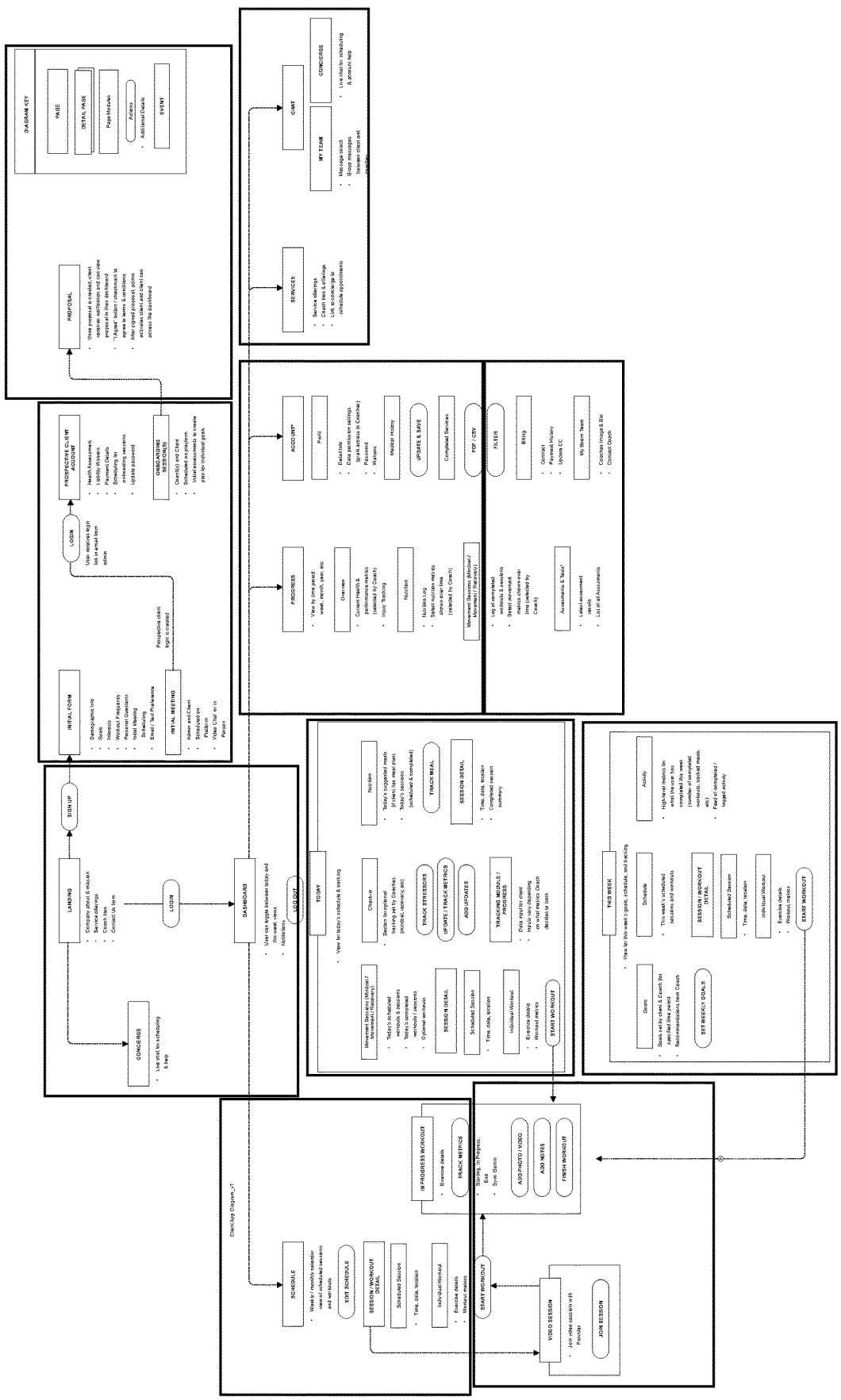
Figure 5A:
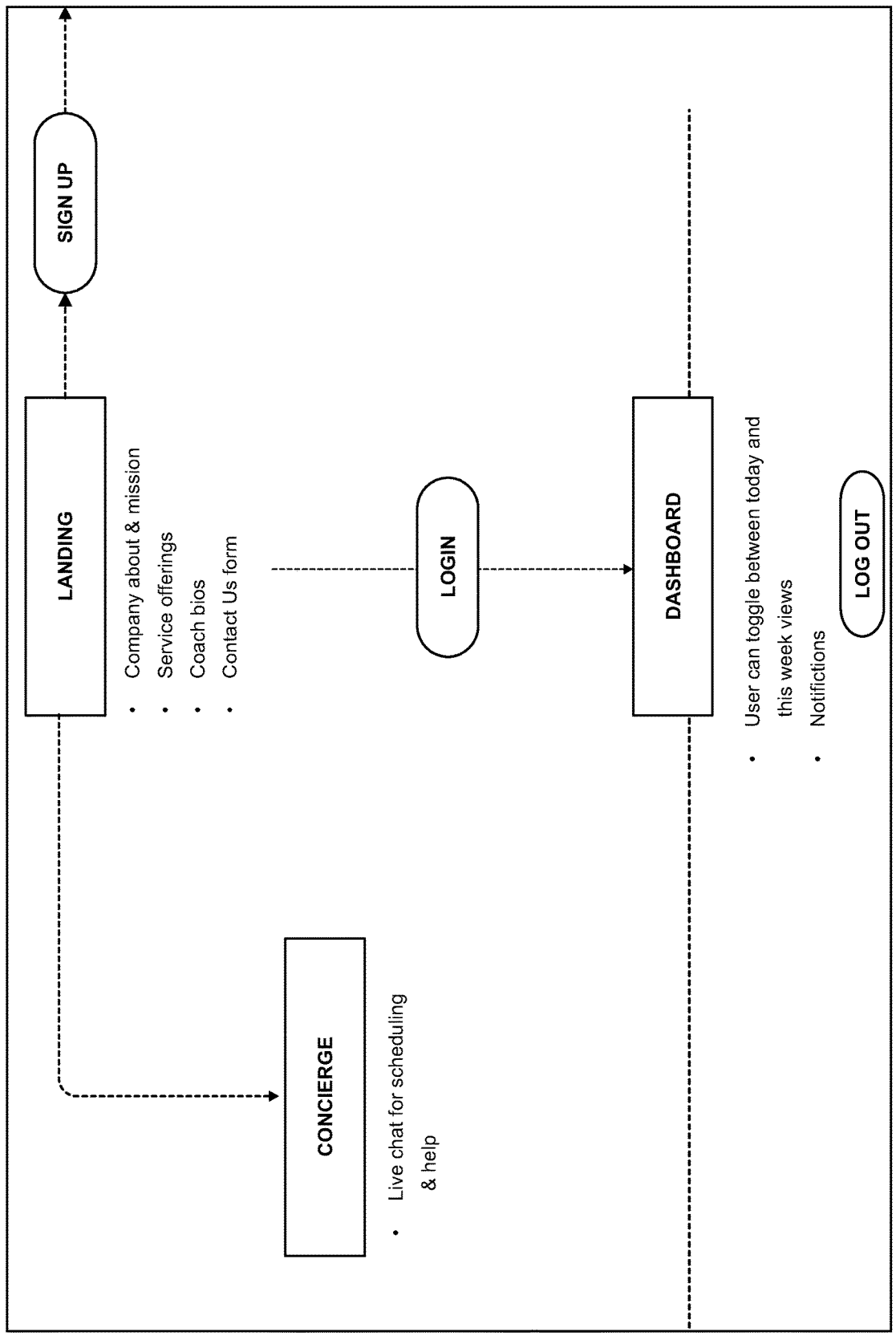
Figure 5B:
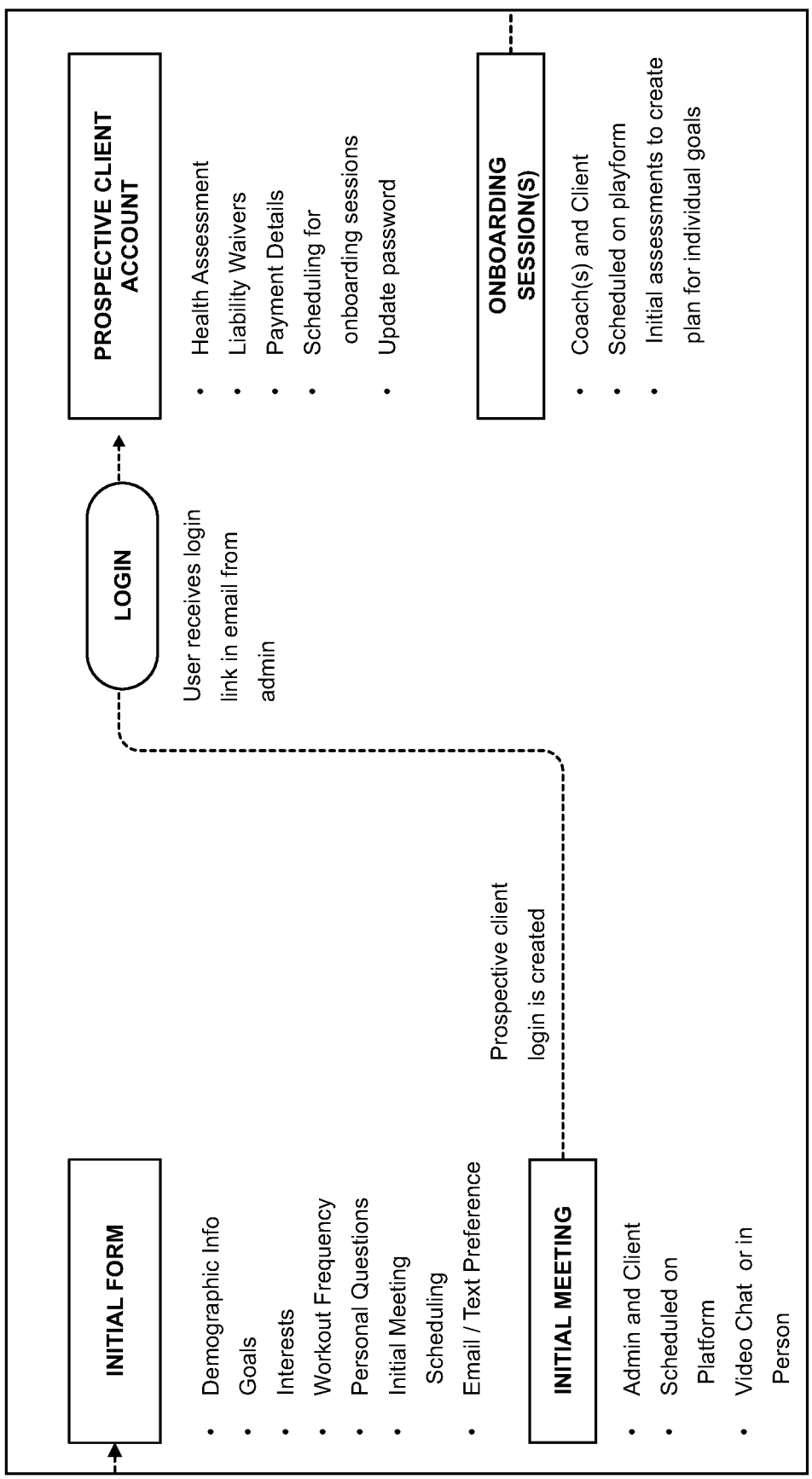
Figure 5C:
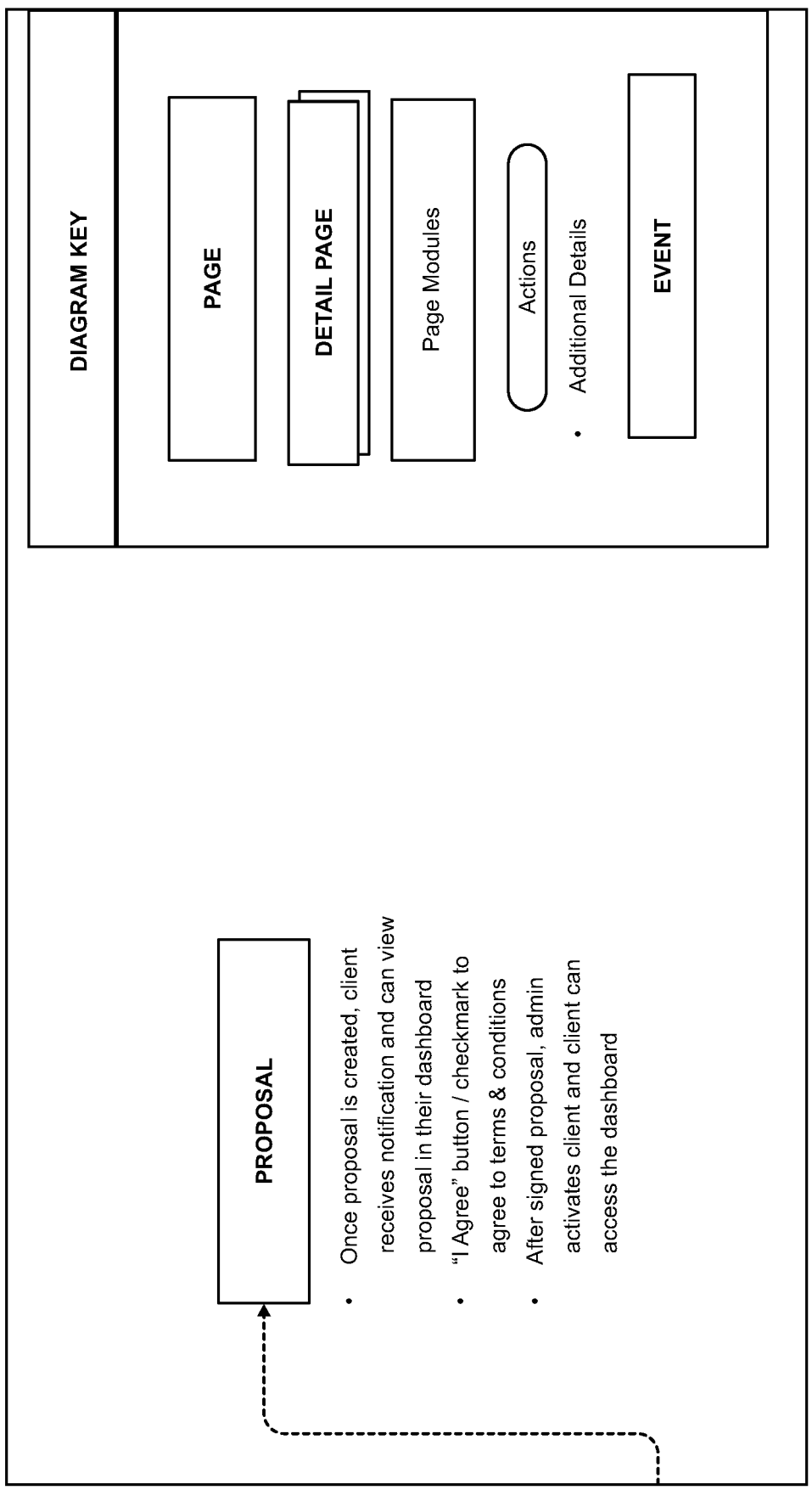
Figure 5D:
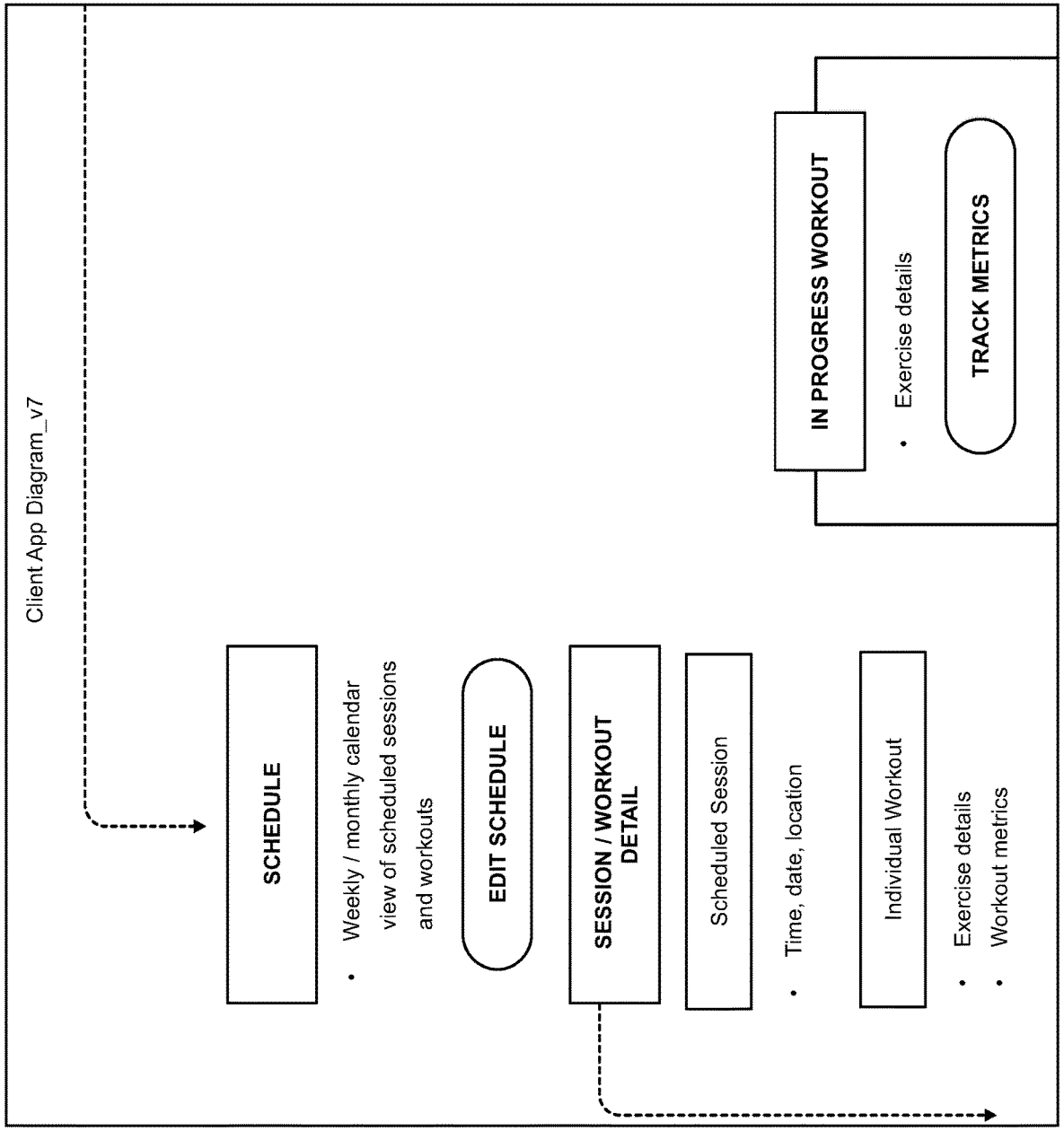
Figure 5E:
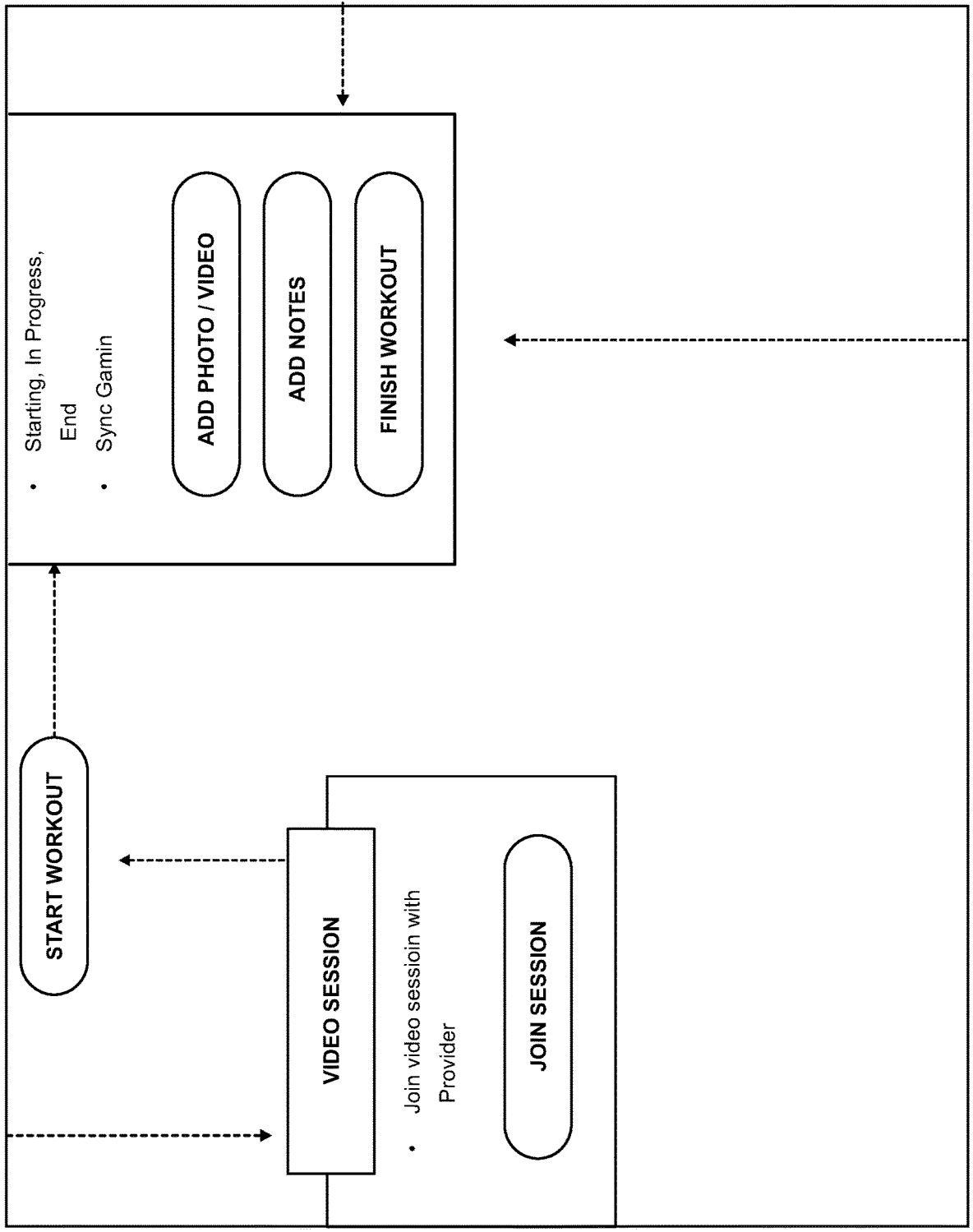
Figure 5F:
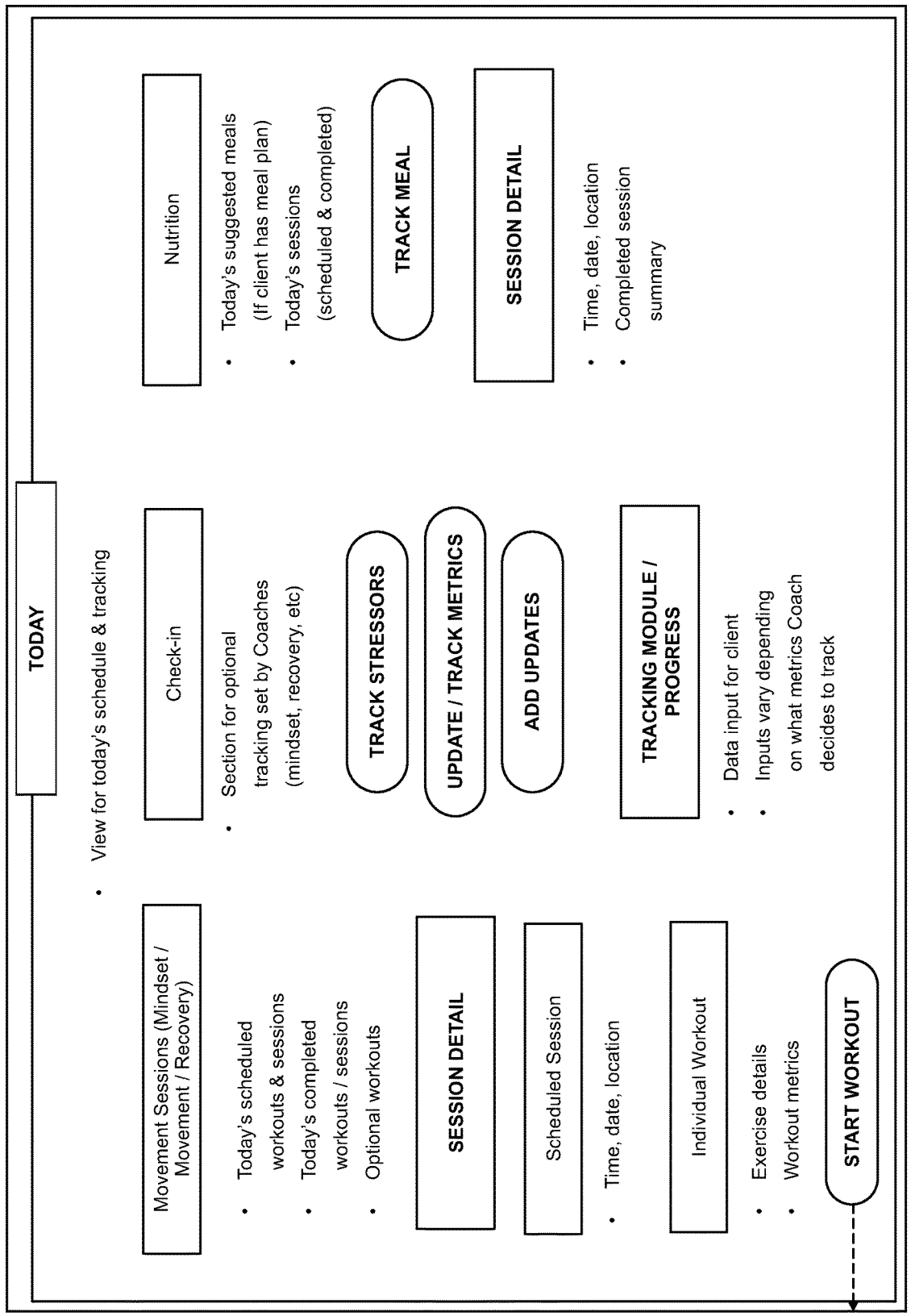
Figure 5G:
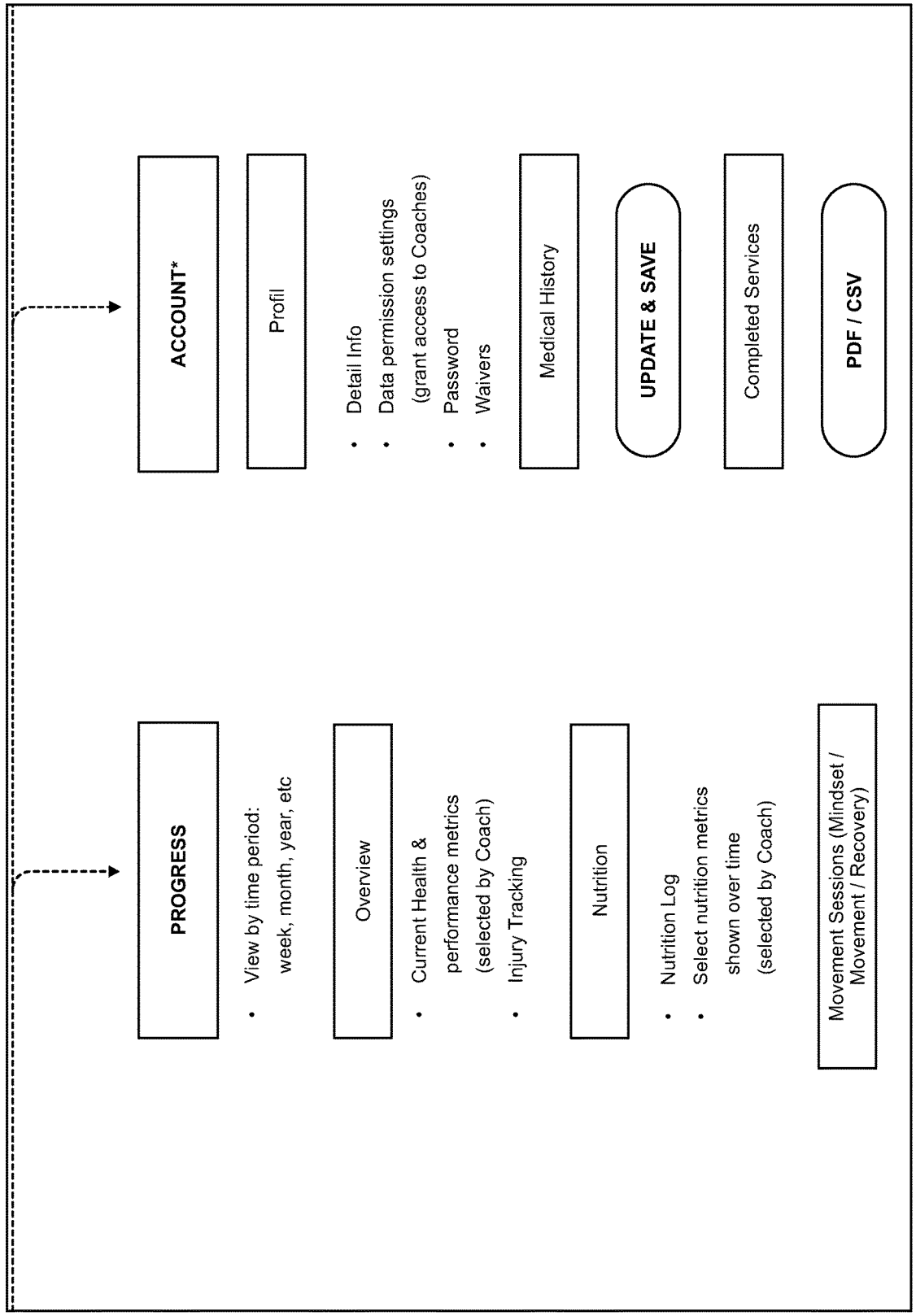
Figure 5H:
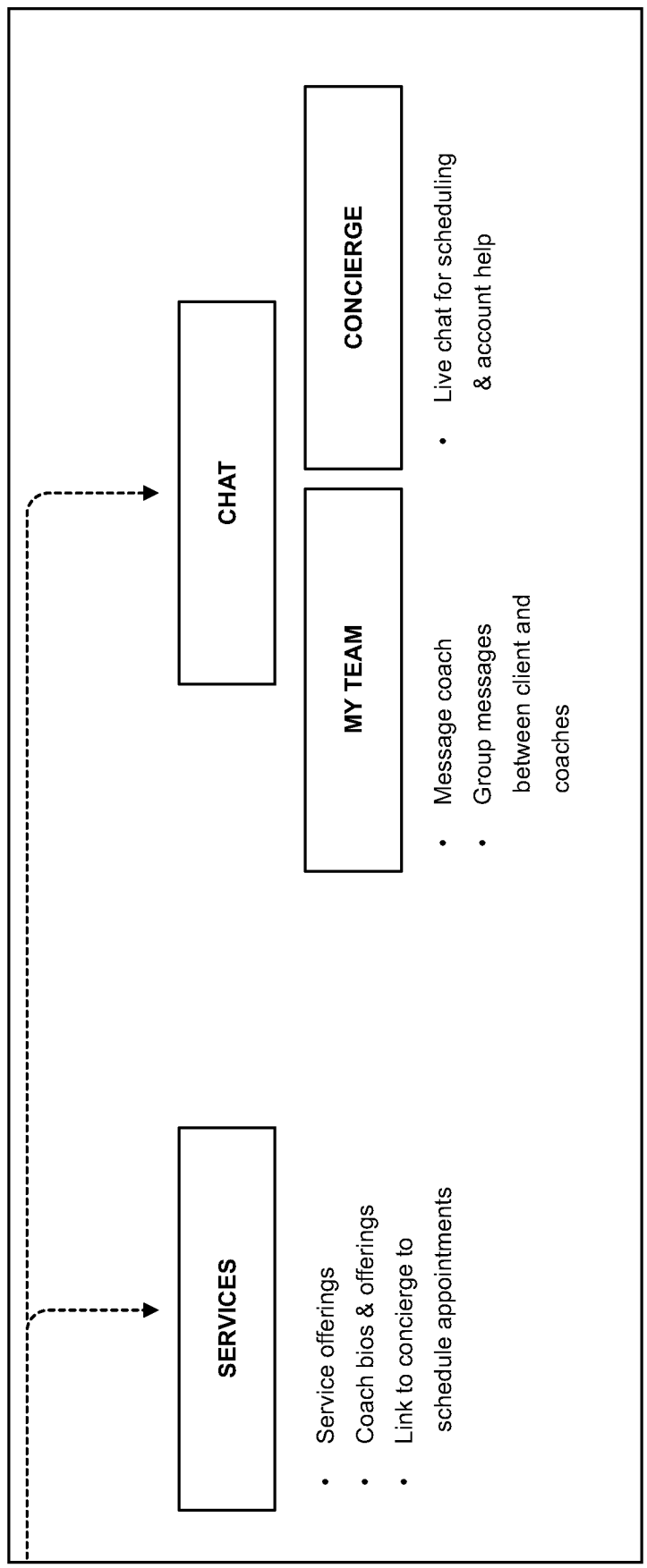
Figure 5I:
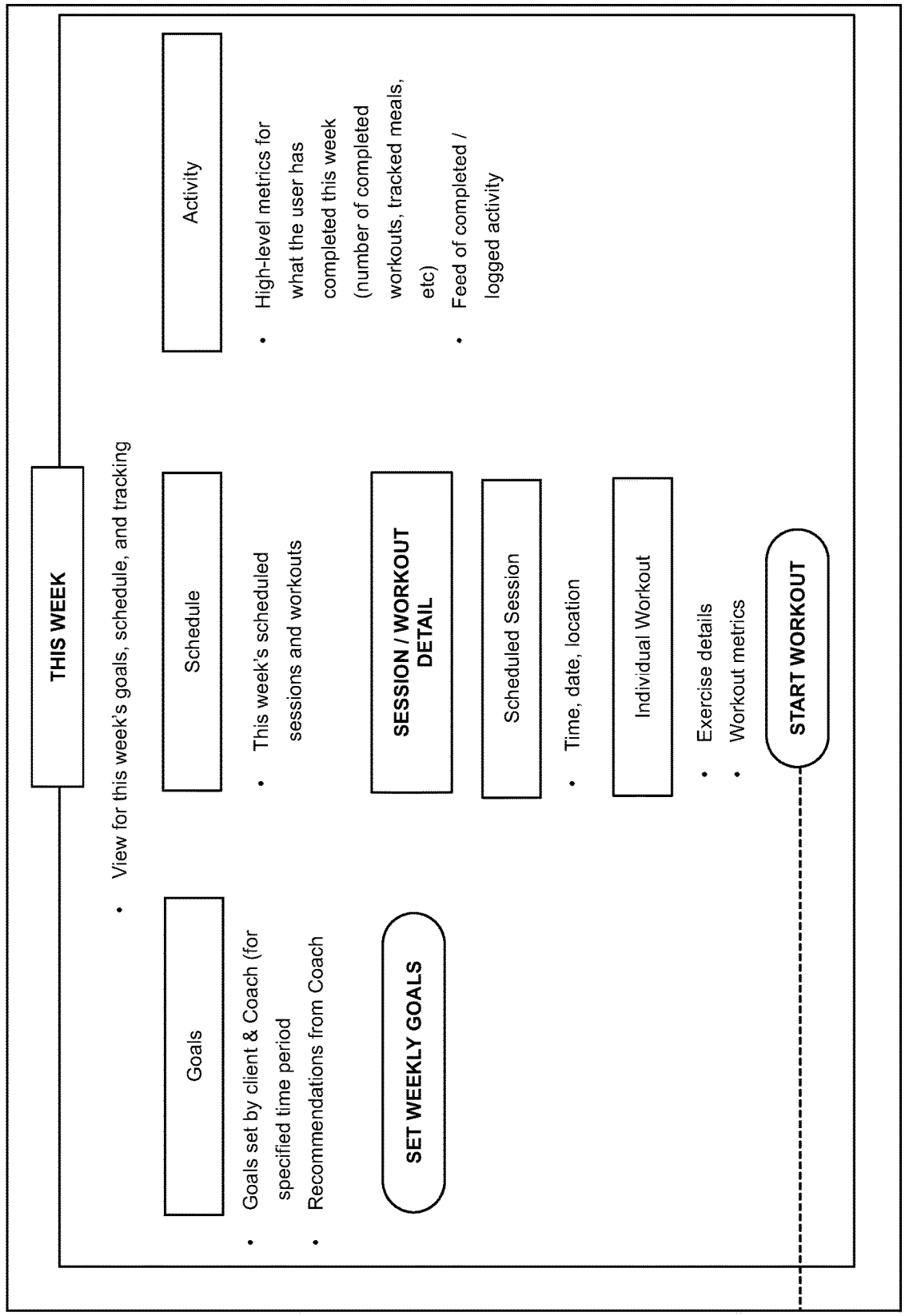
Figure 5J:
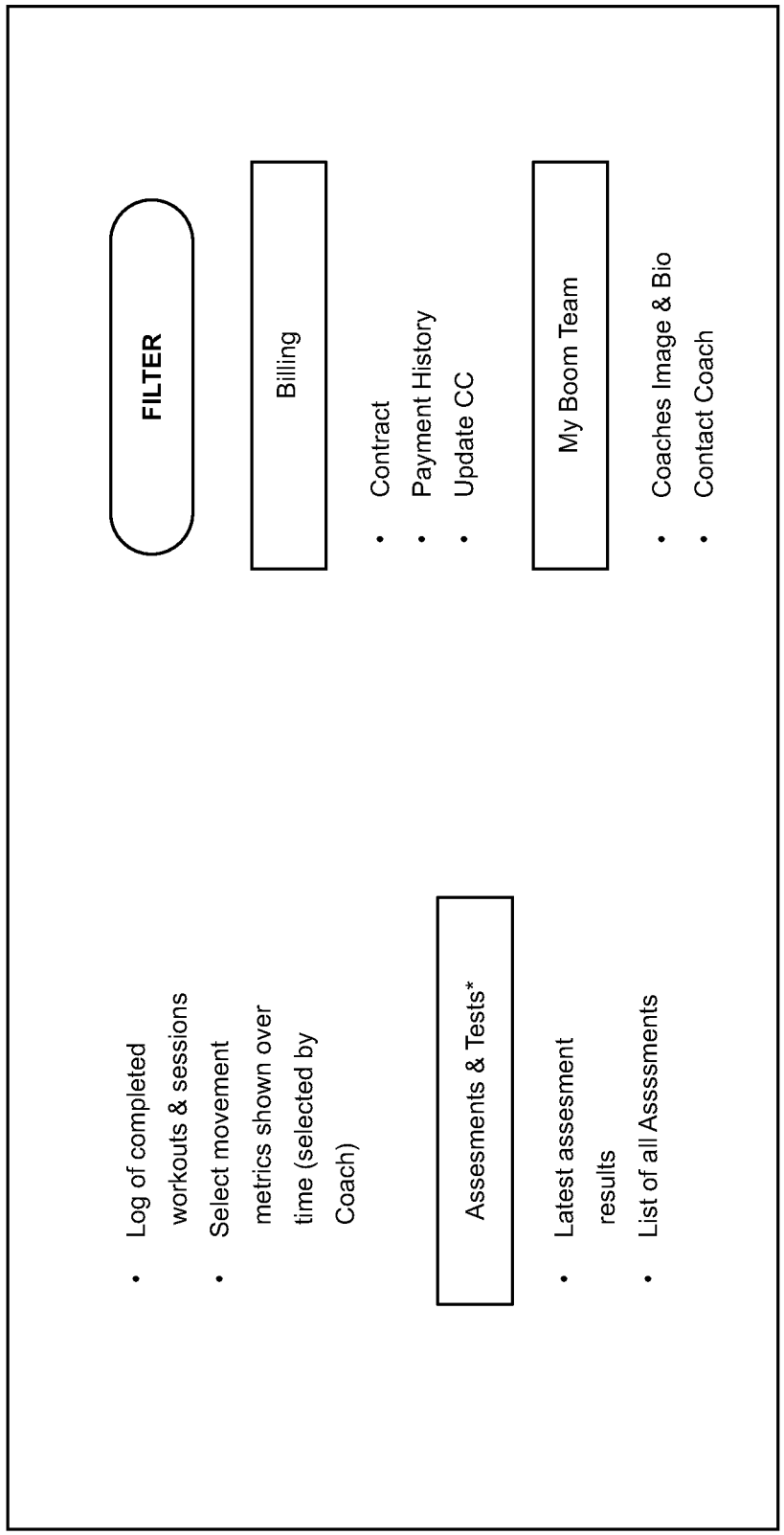
Figure 6:
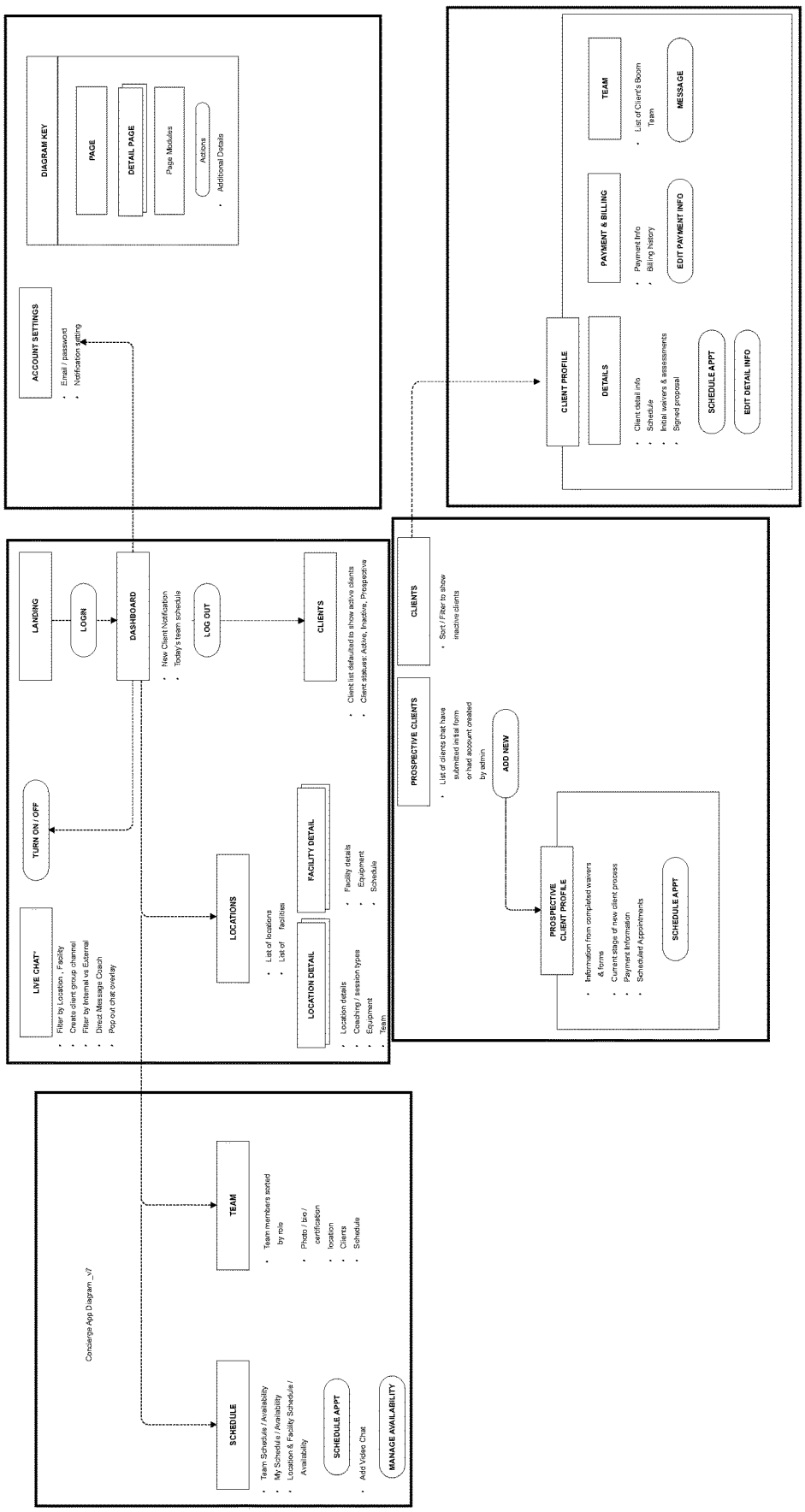
Figure 6A:
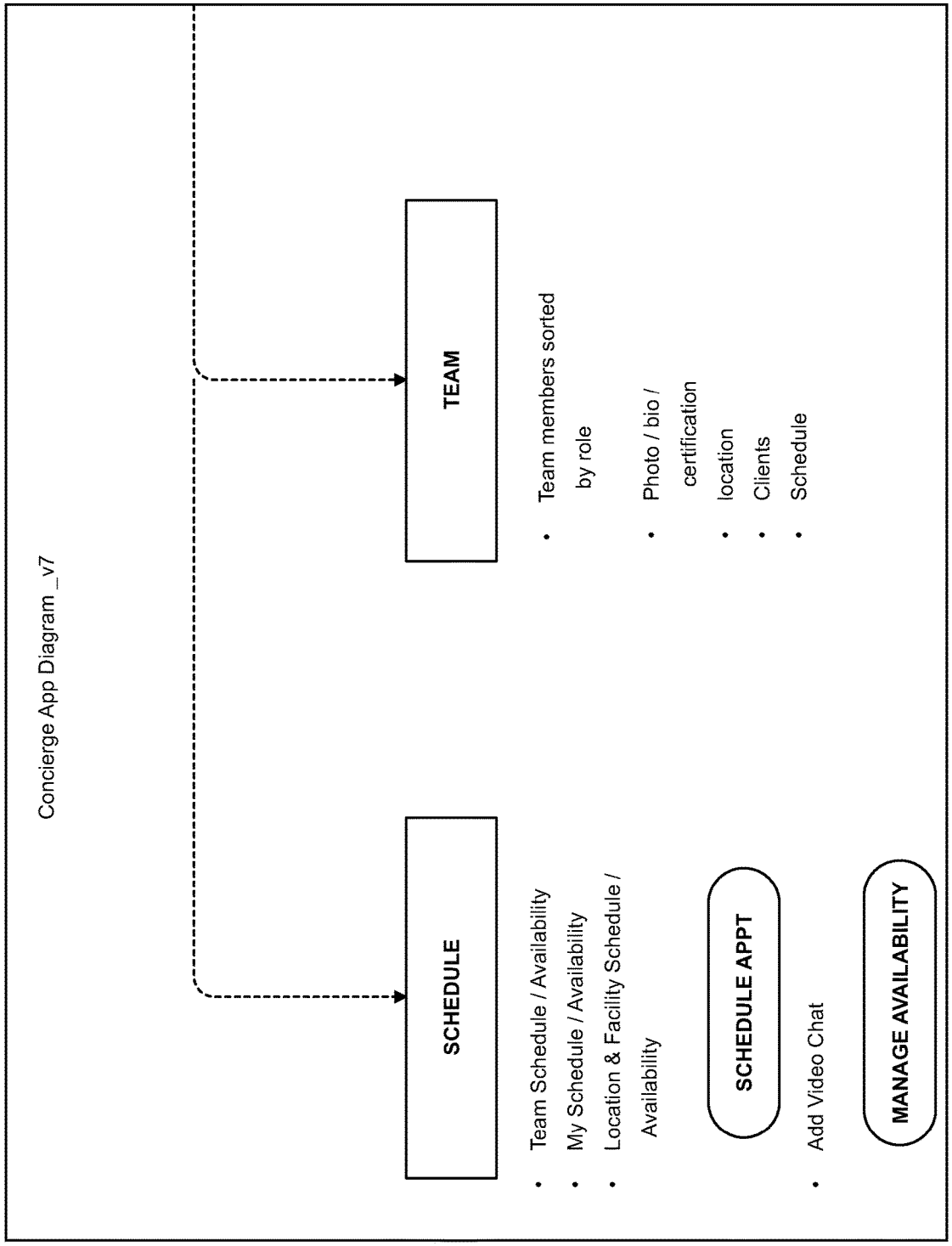
Figure 6B:
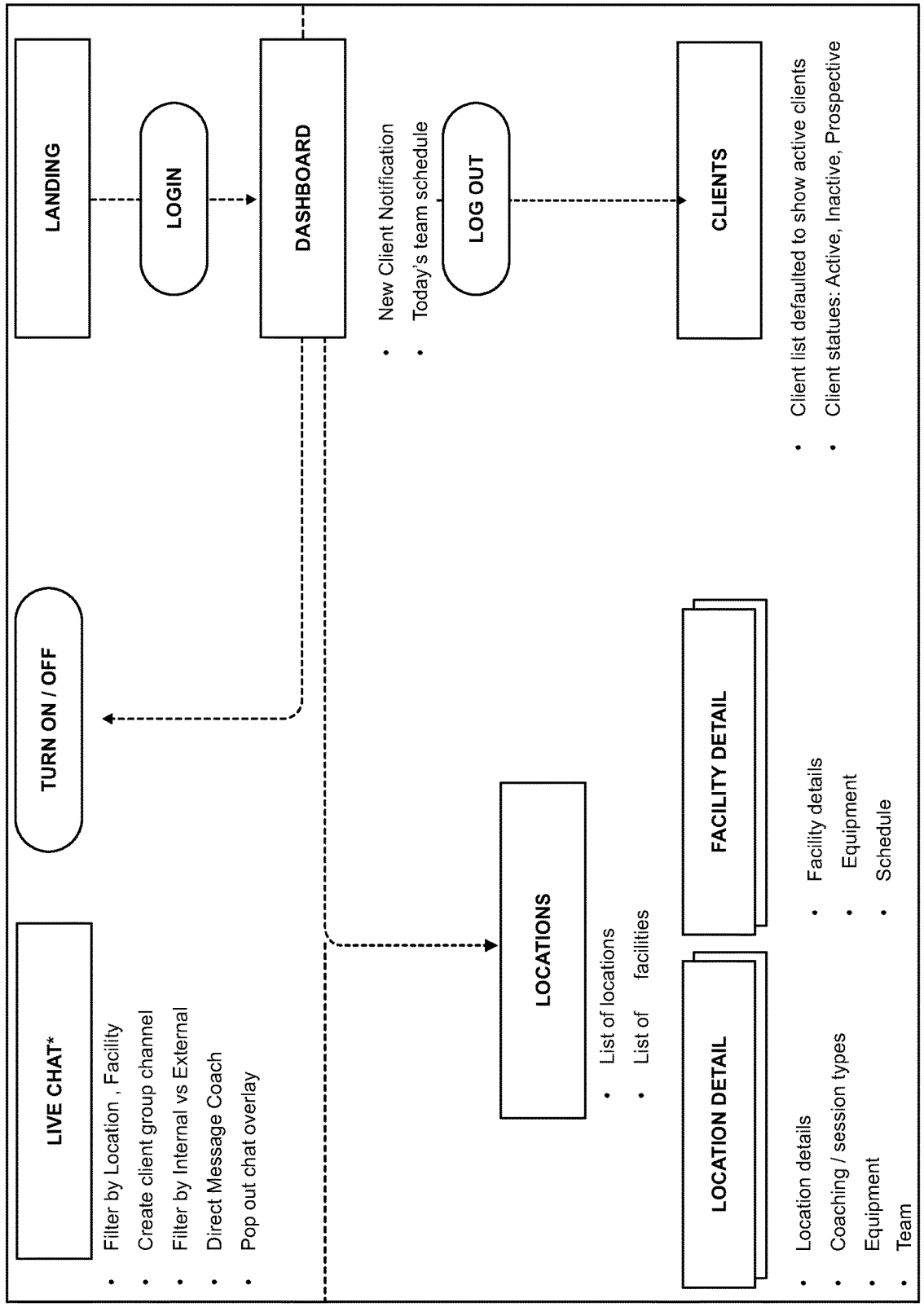
Figure 6C:
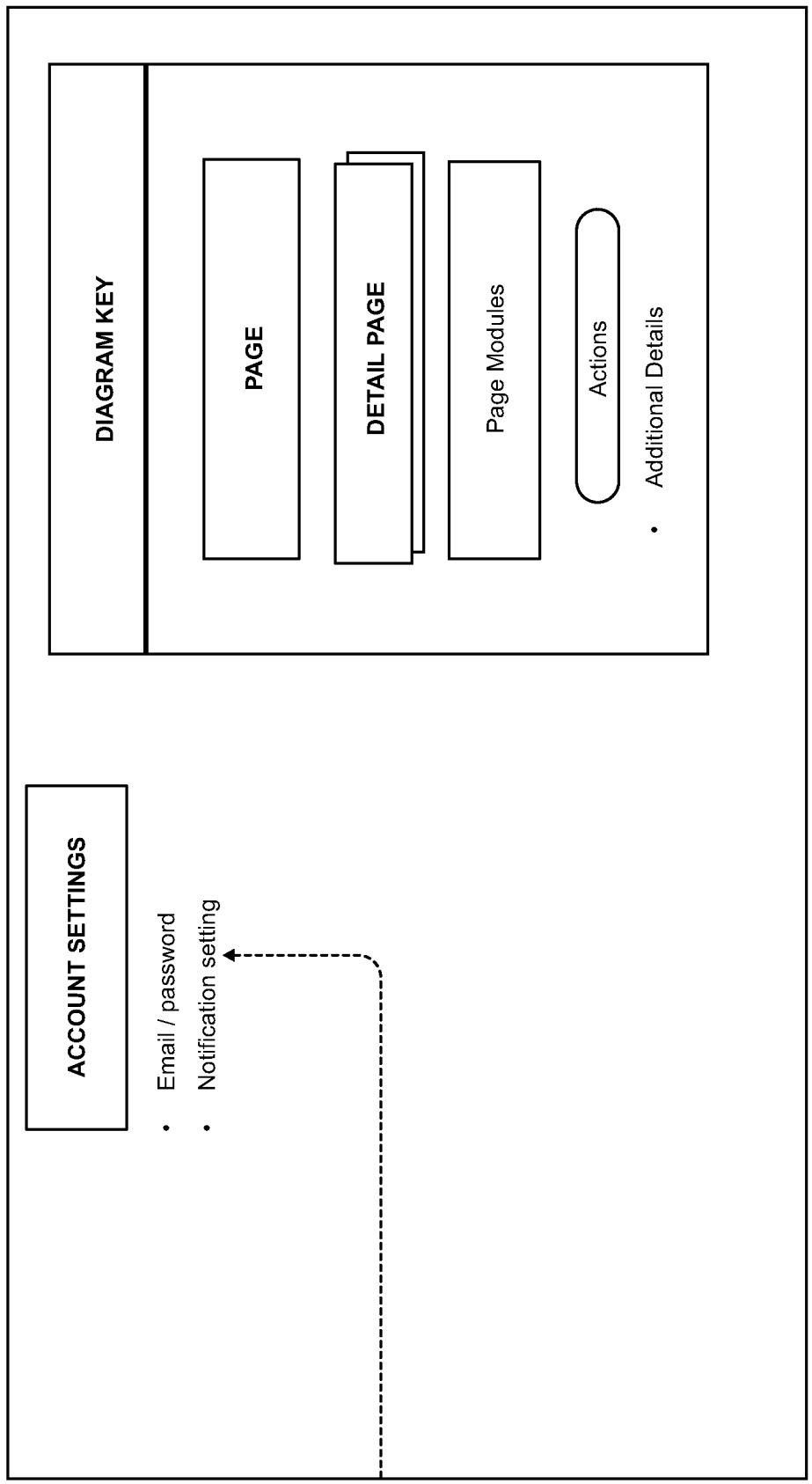
Figure 6D:
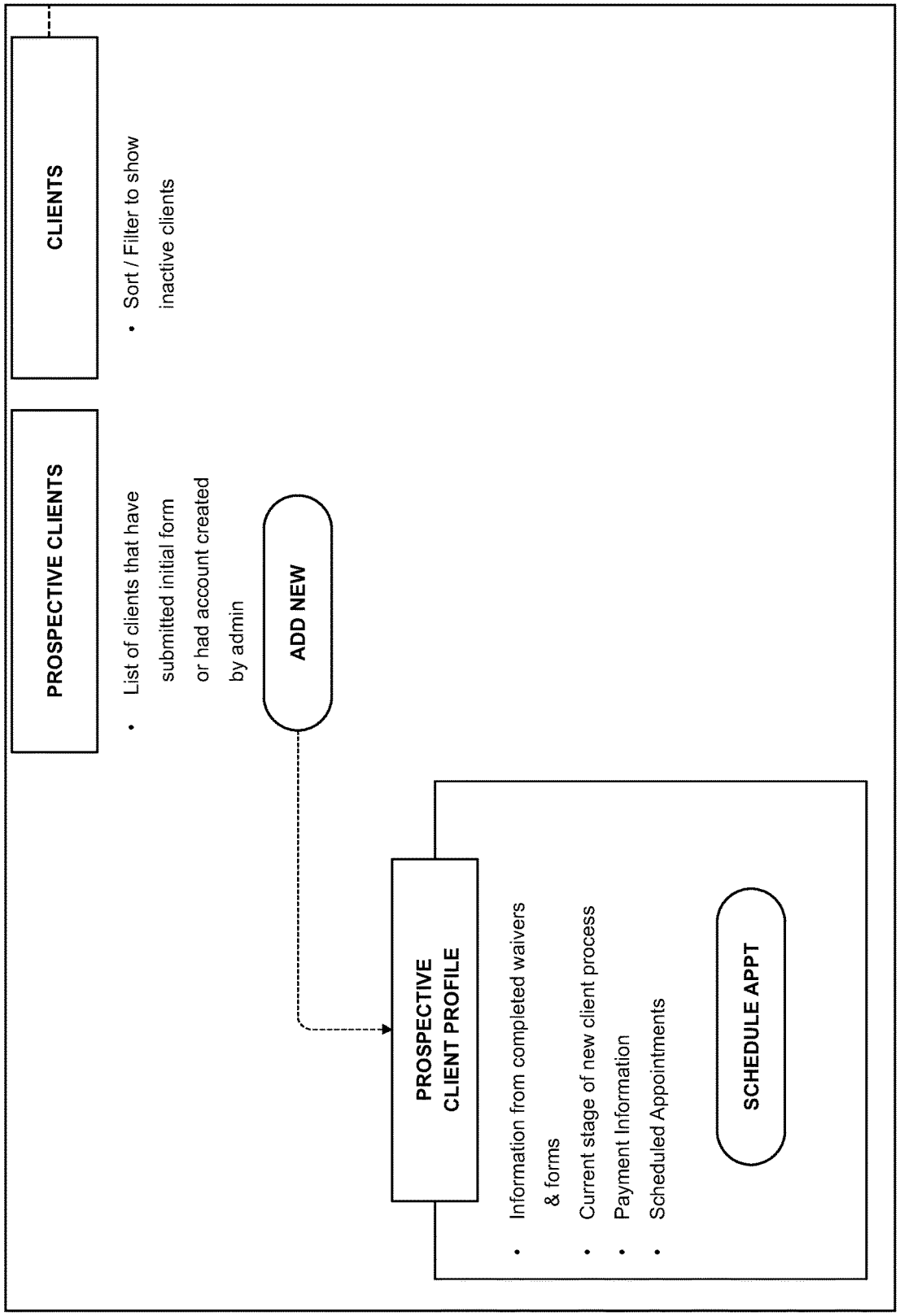
Figure 6E:
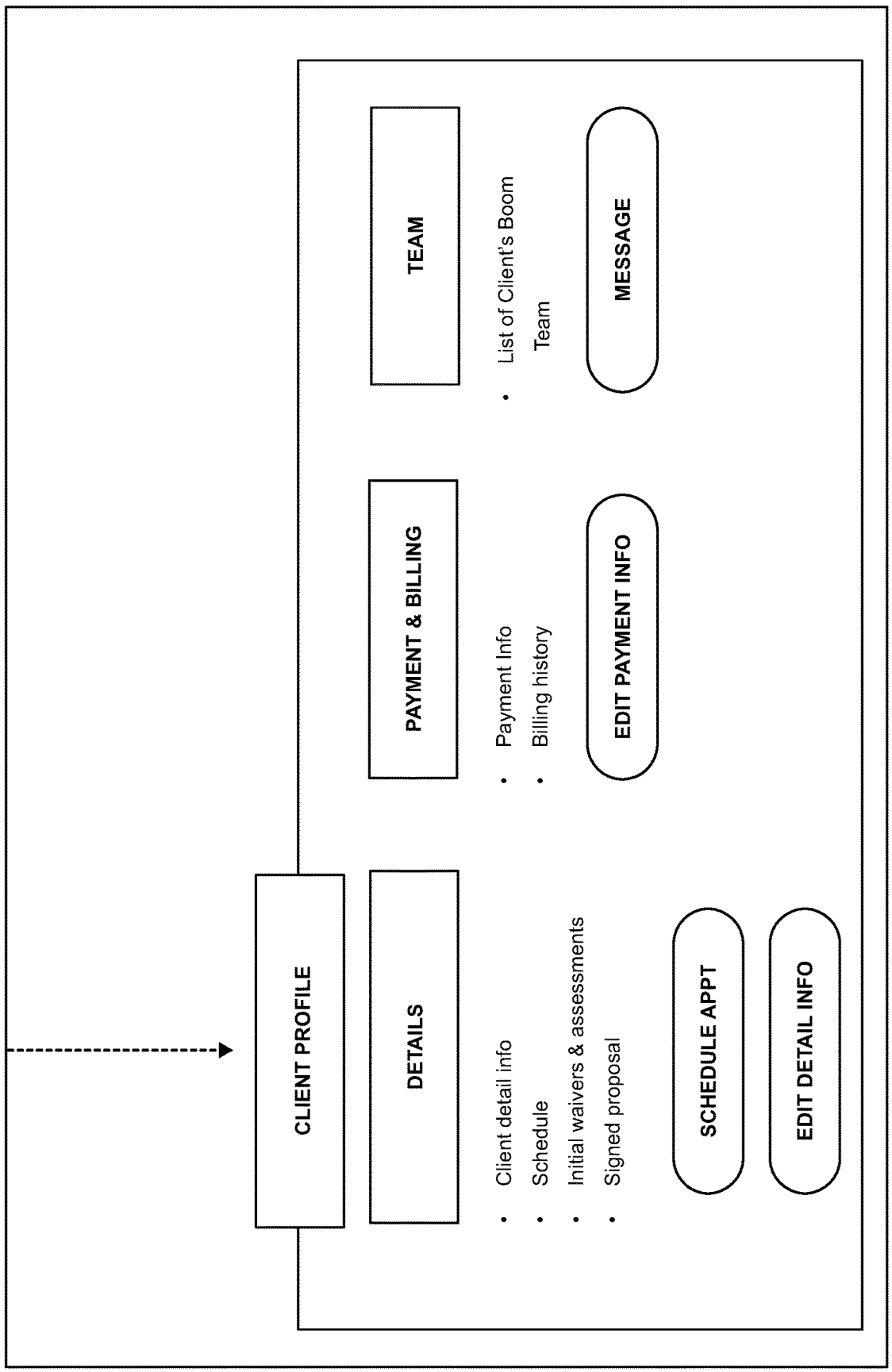
Figure 7:
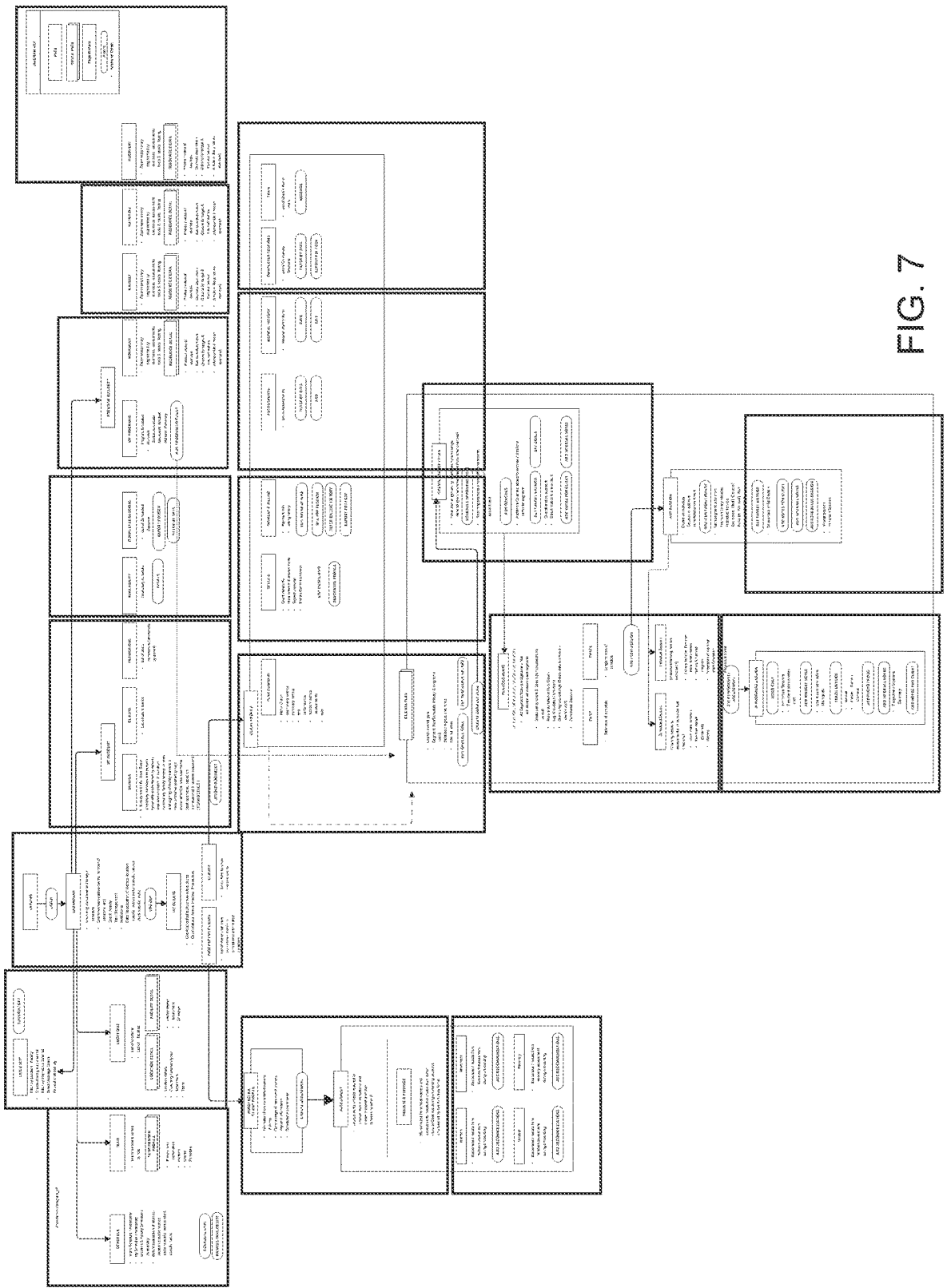
Figure 7A:
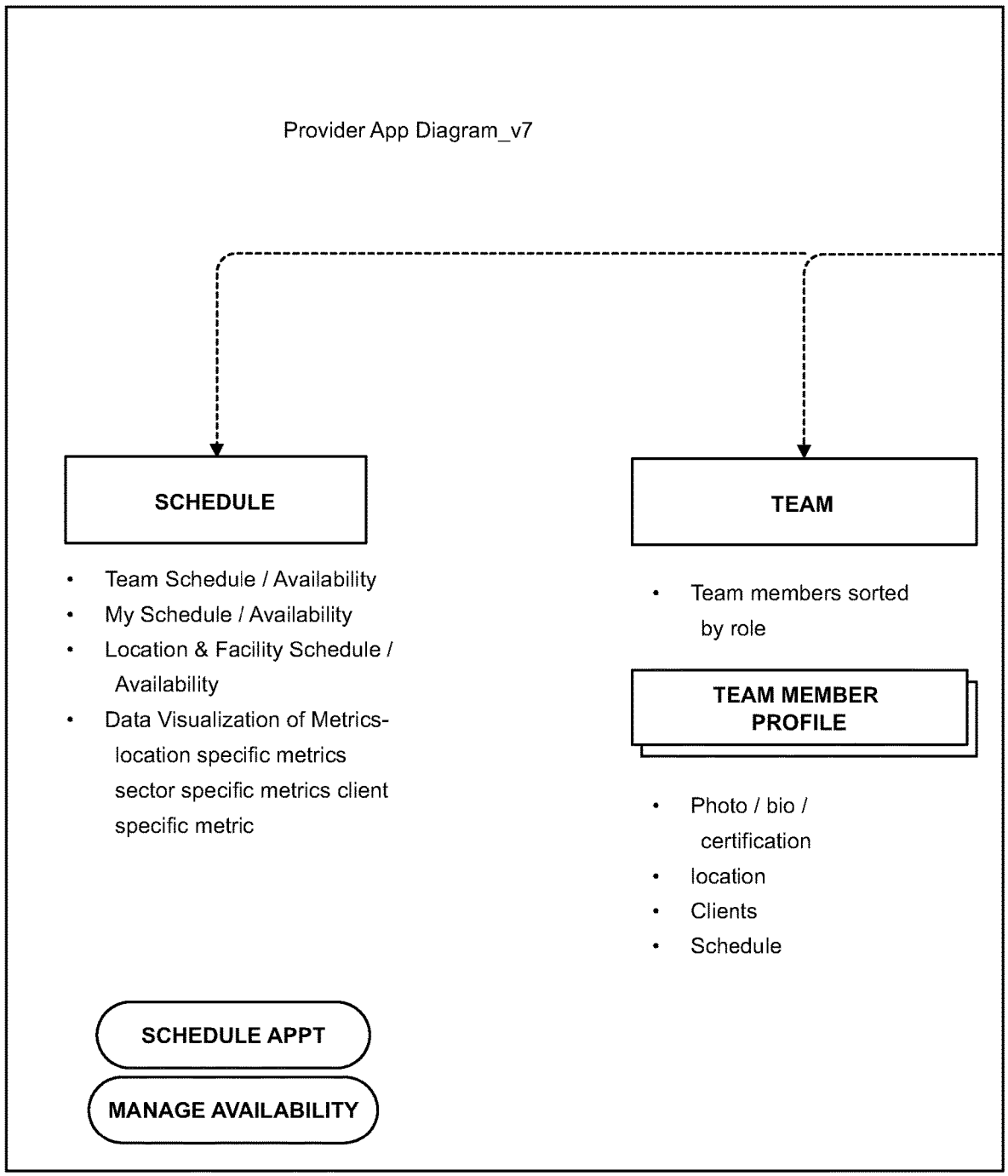
Figure 7B:
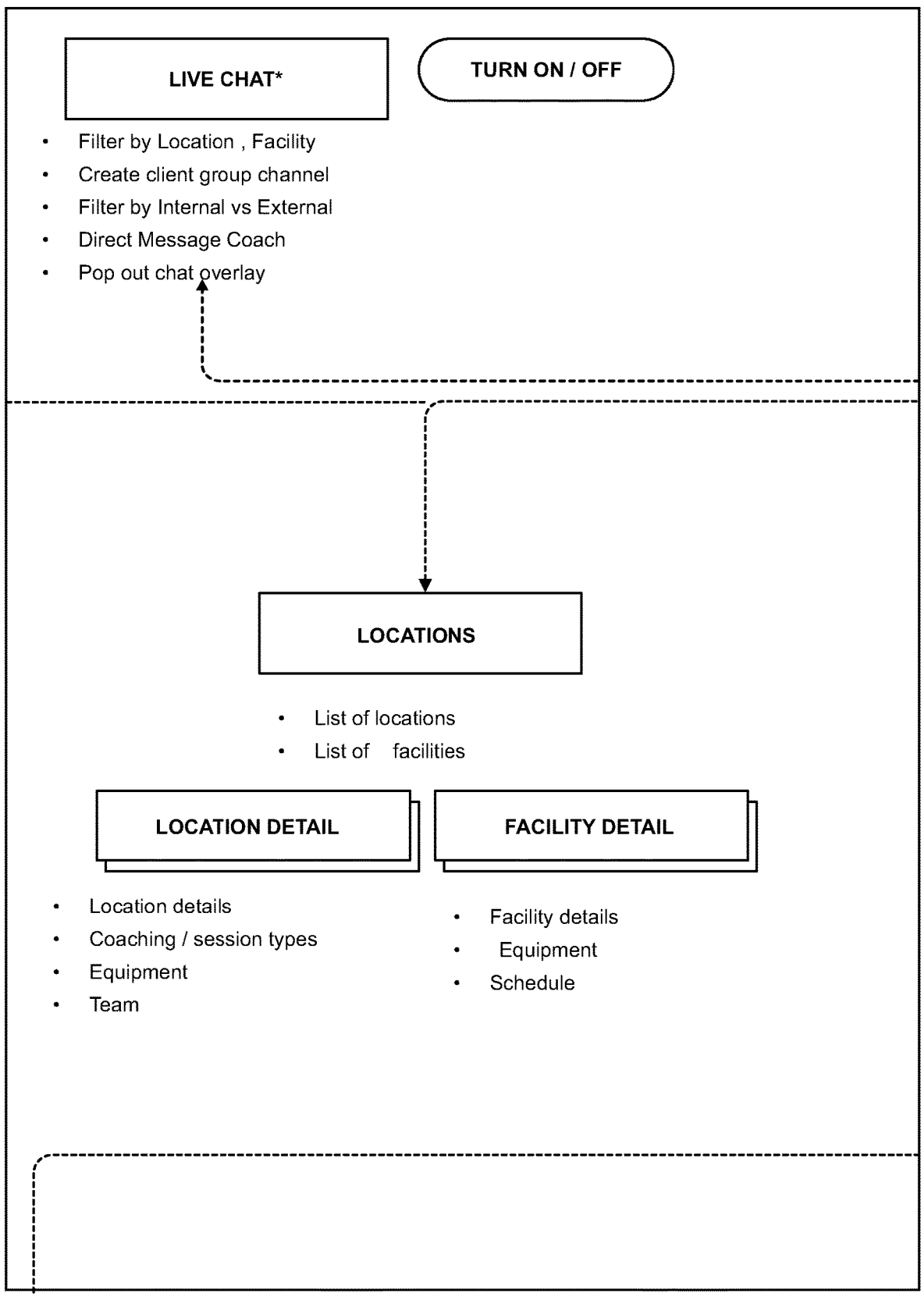
Figure 7C:
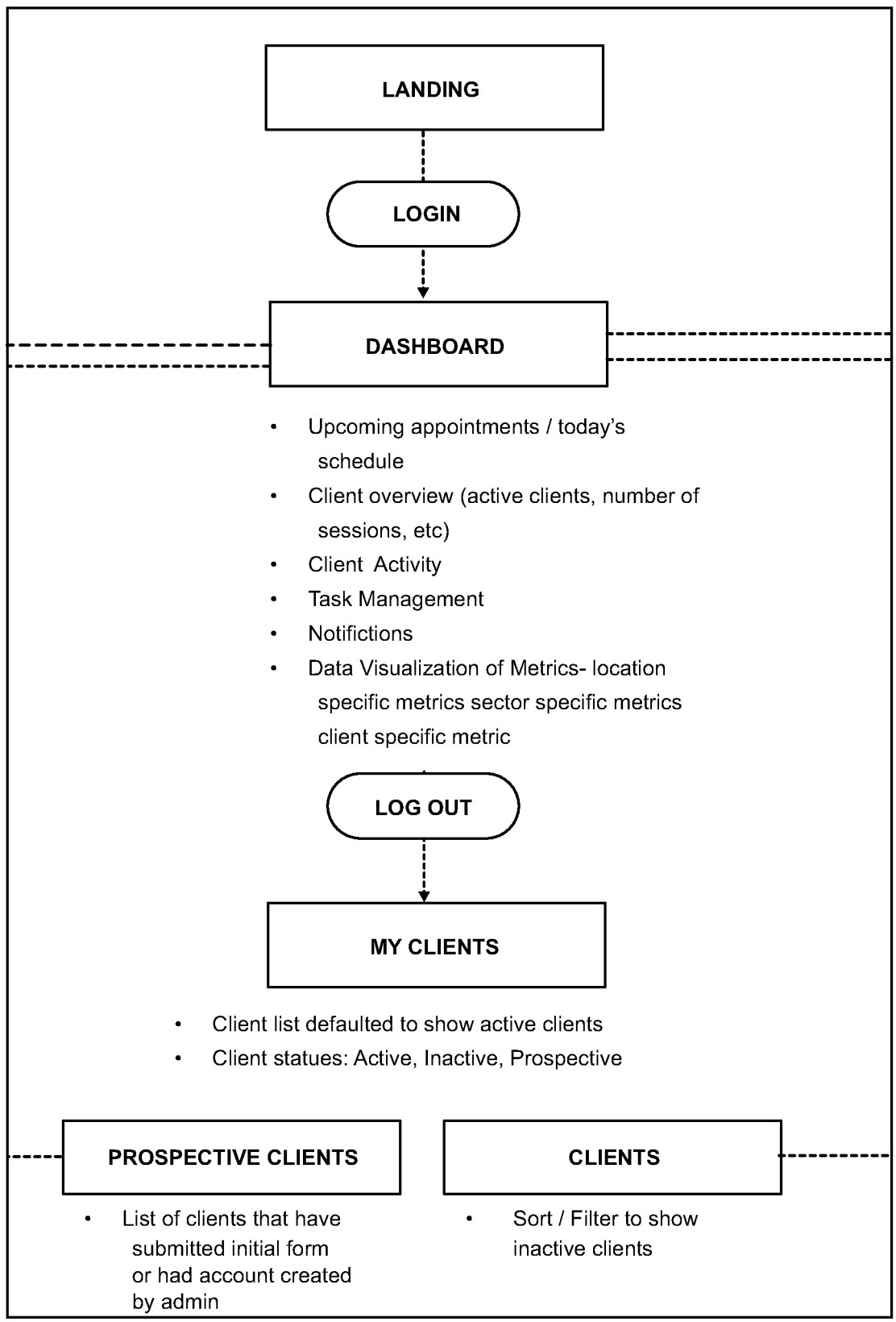
Figure 7D:
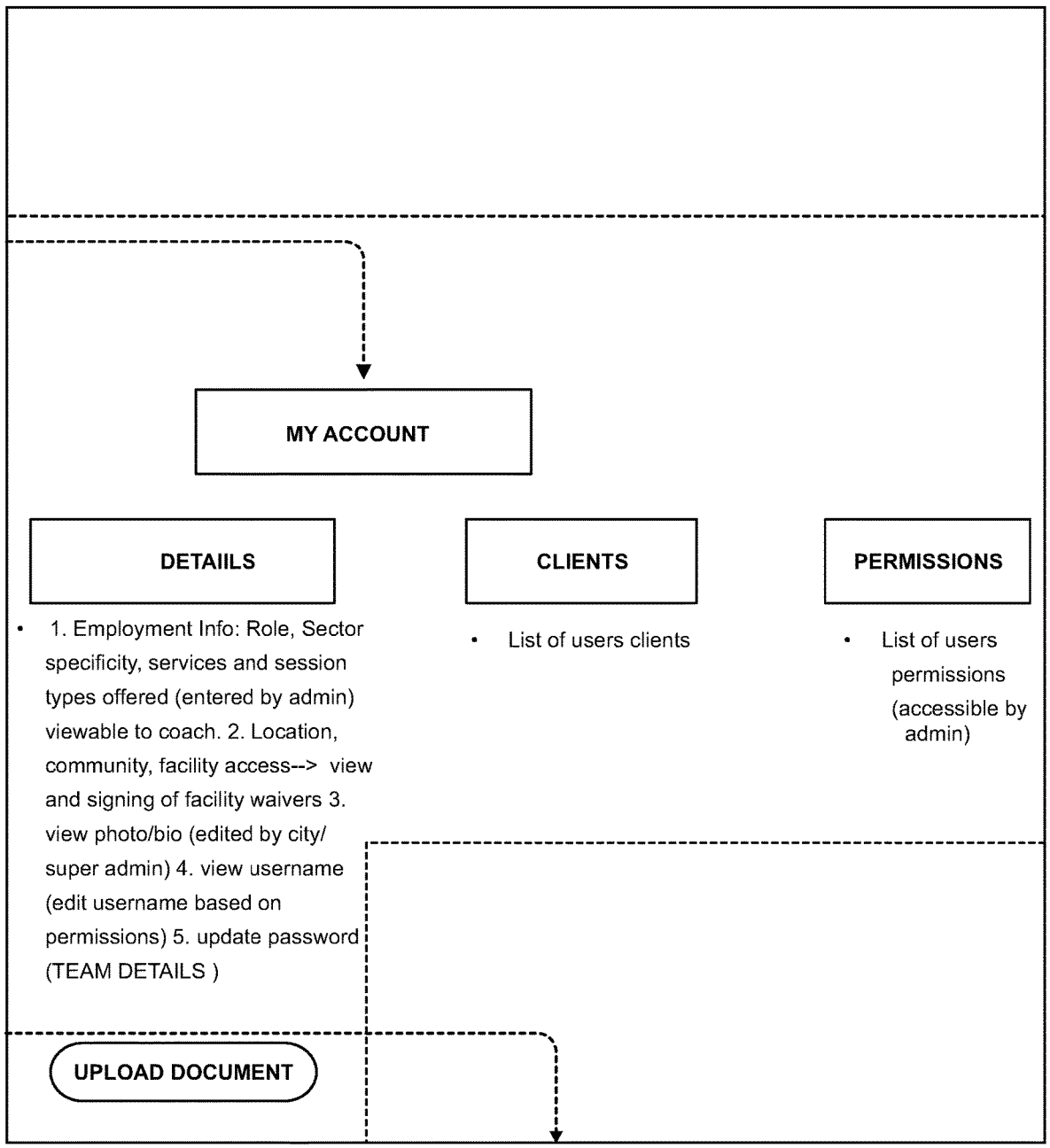
Figure 7E:
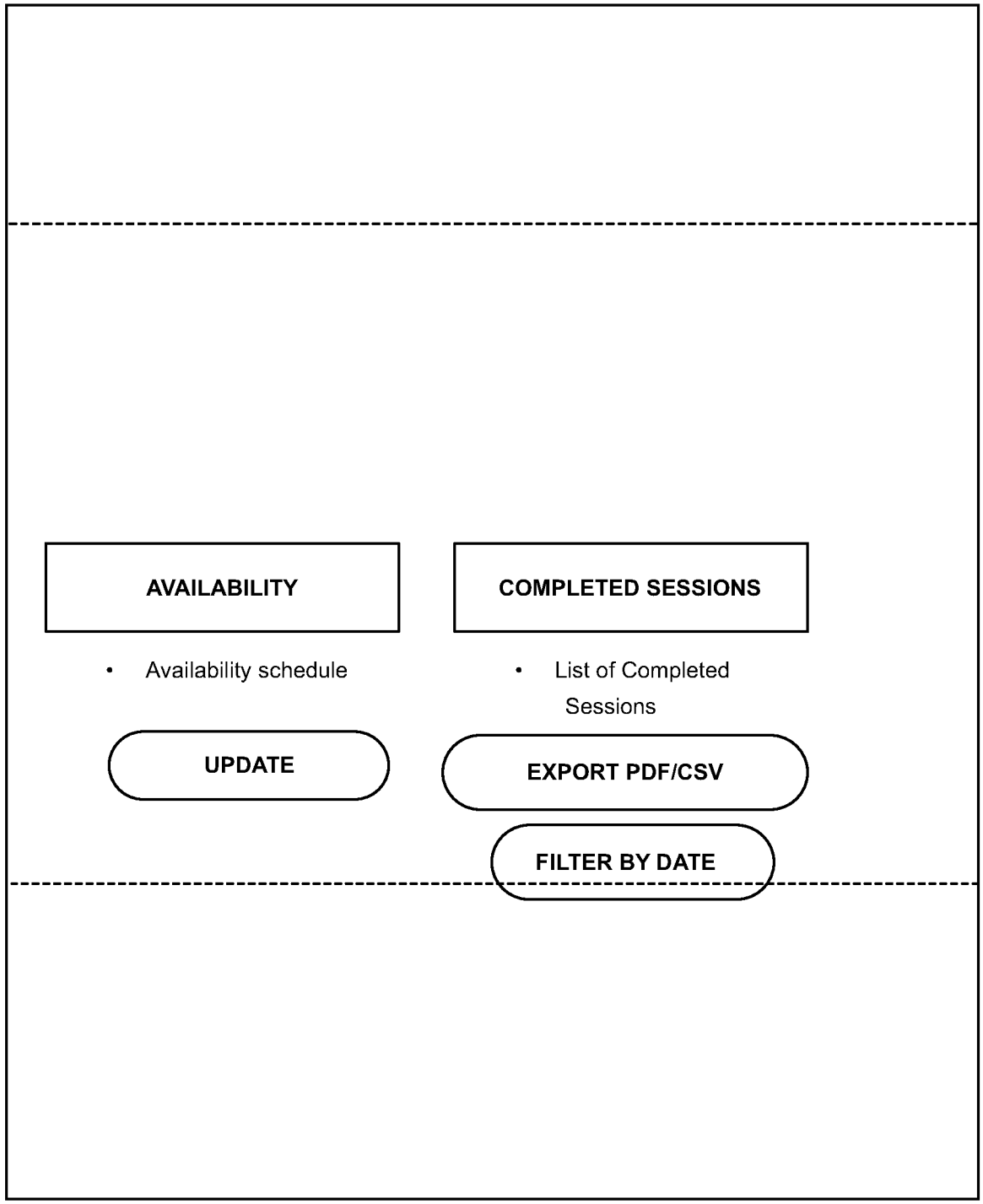
Figure 7F:
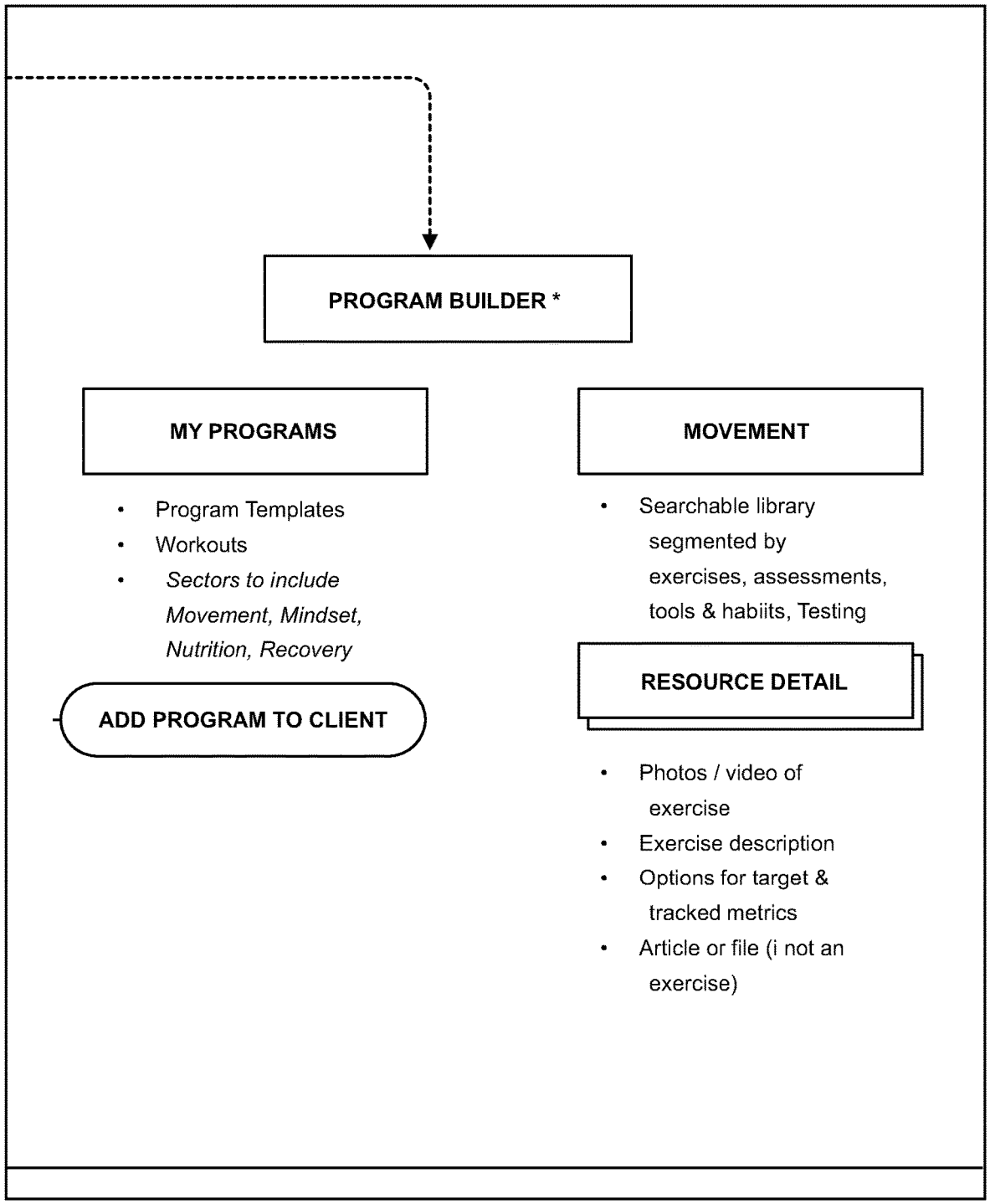
Figure 7G:
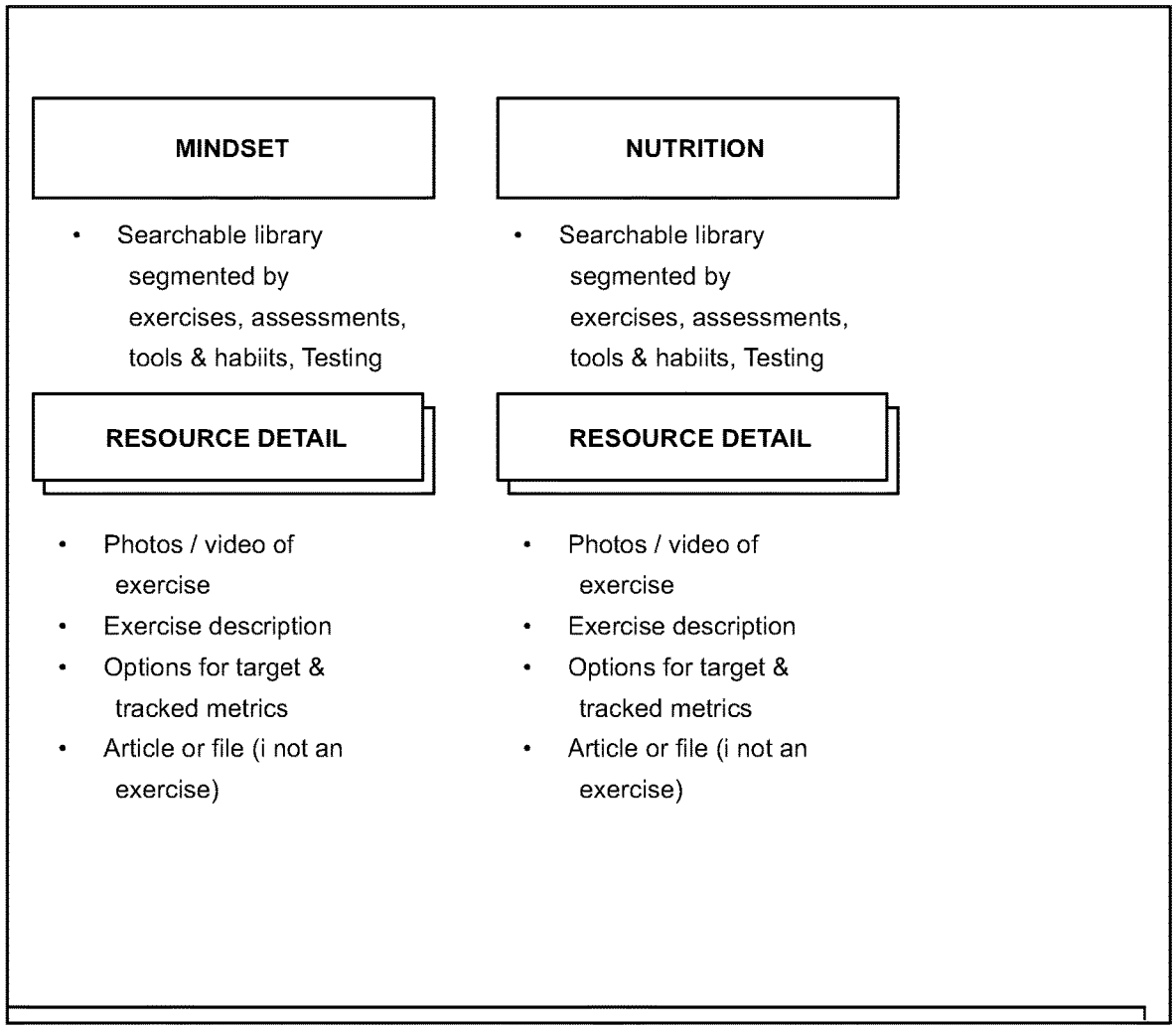
Figure 7H:
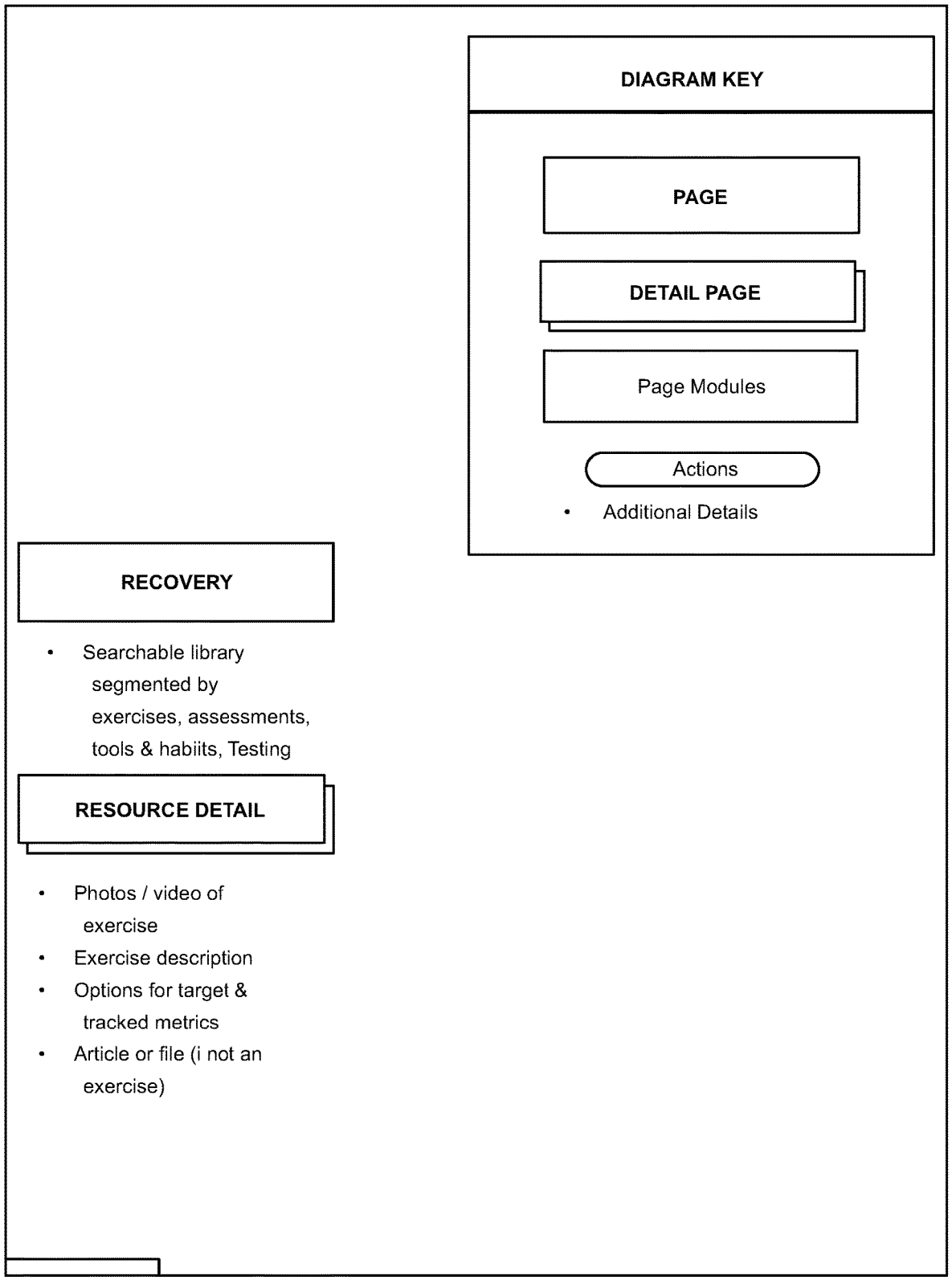
Figure 71:
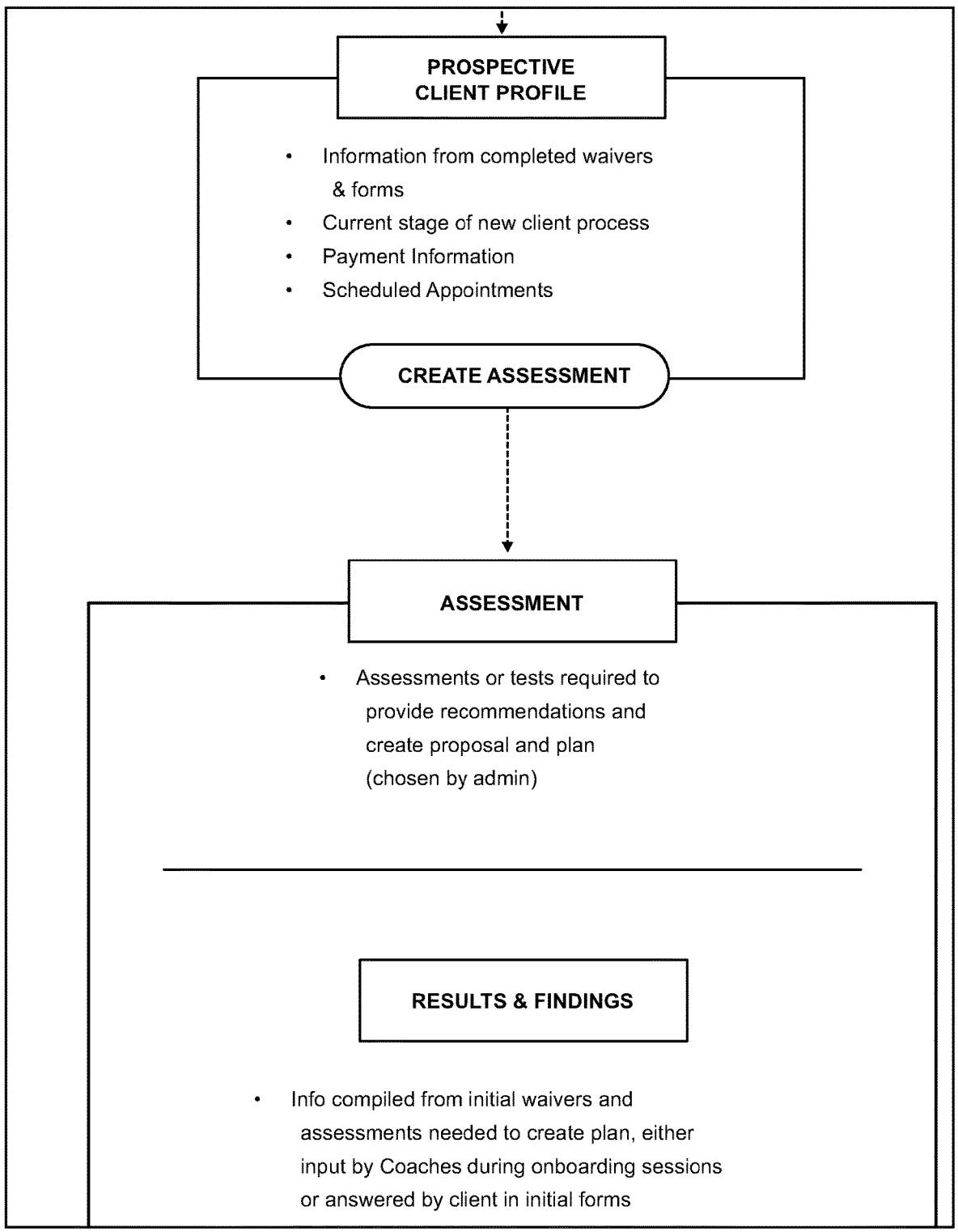
Figure 7J:
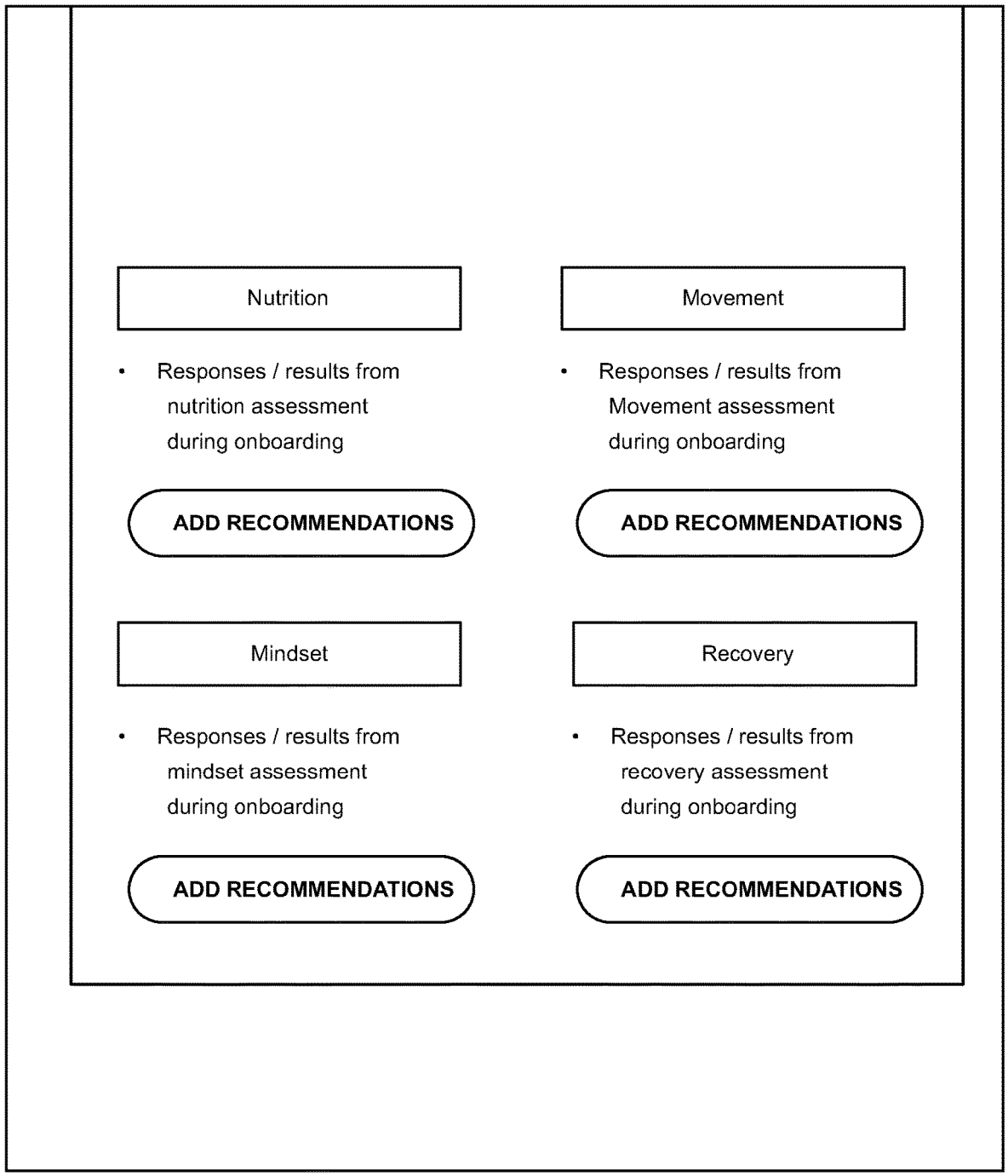
Figure 7K:
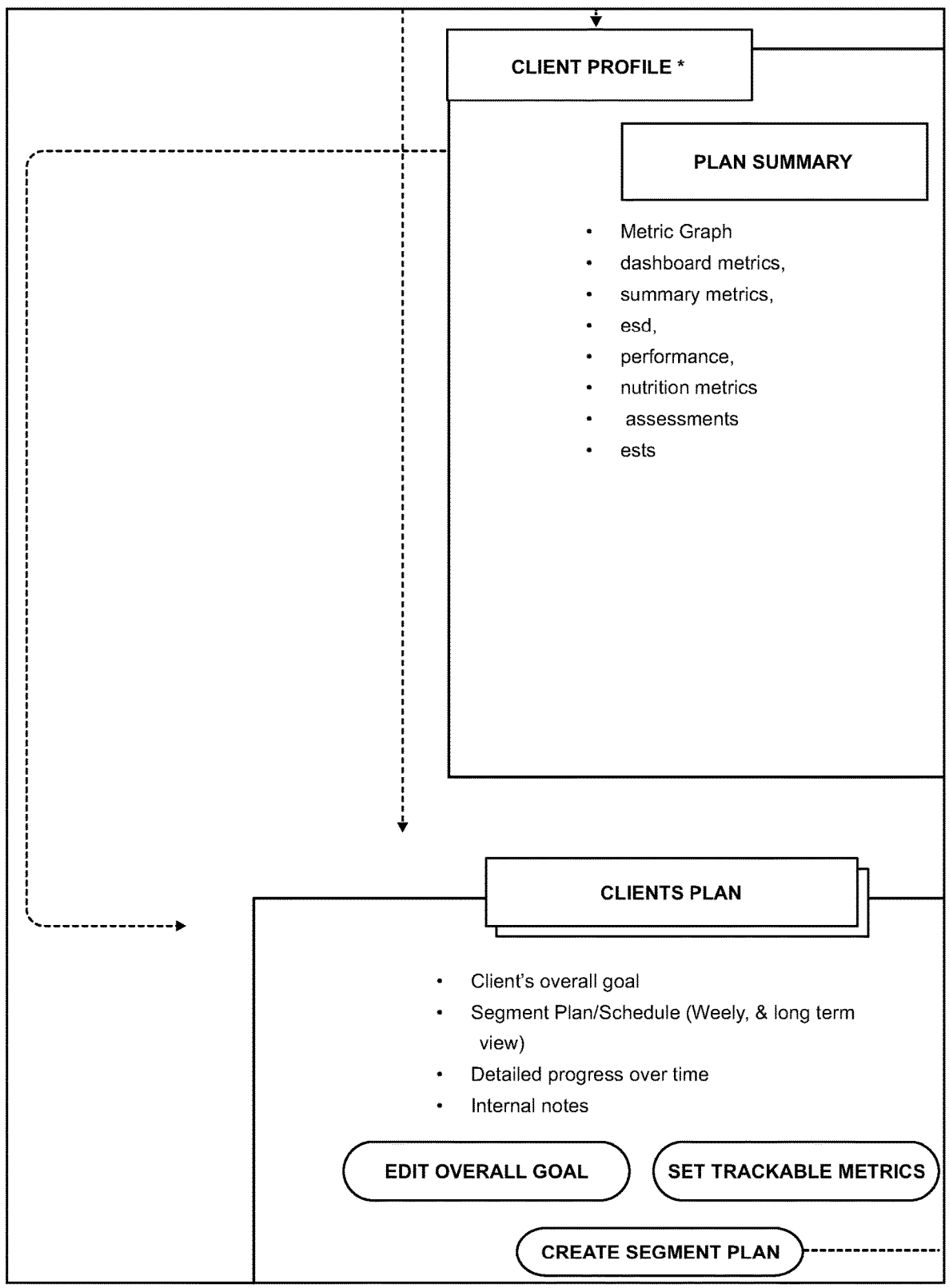
Figure 7L:
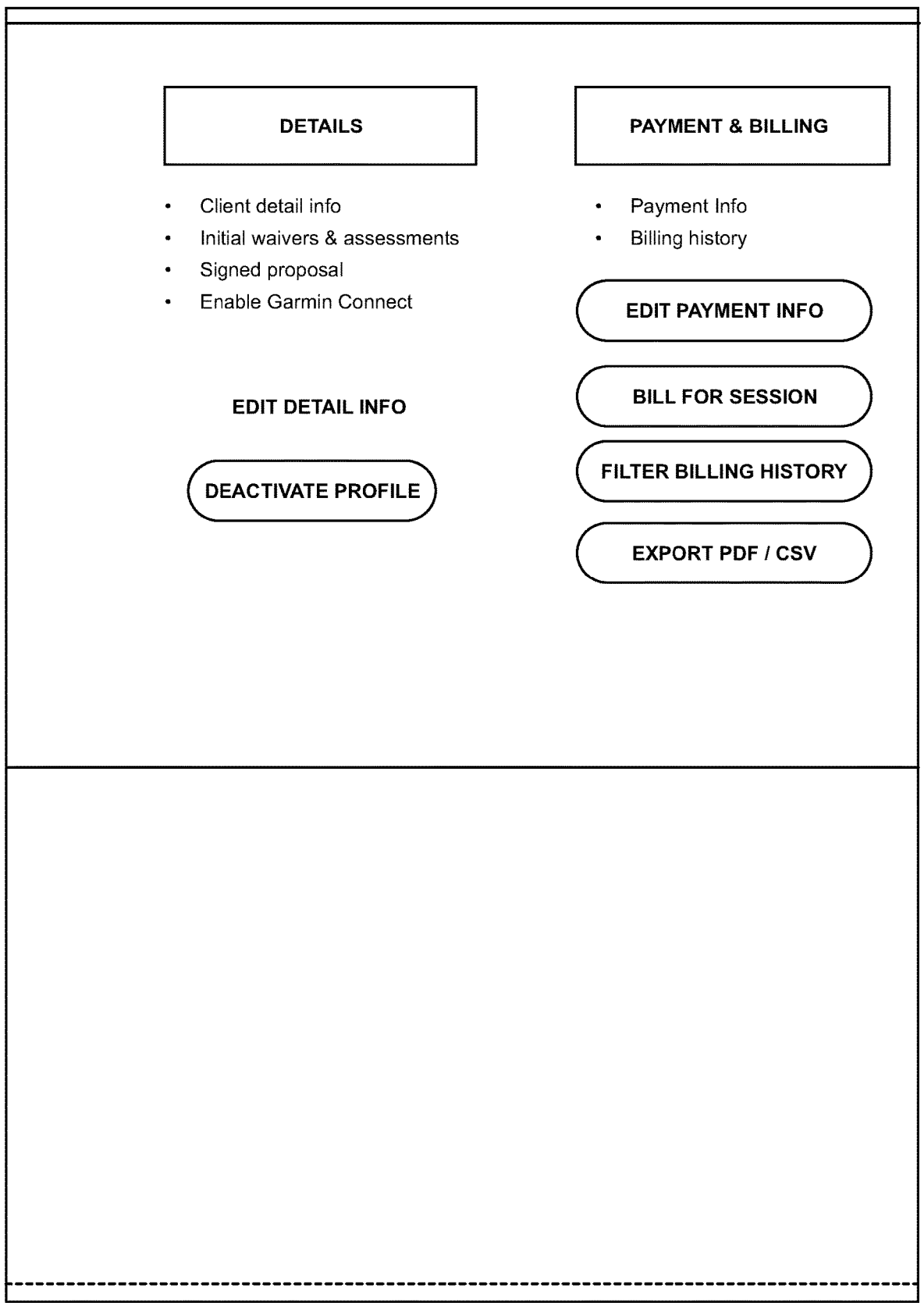
Figure 7M:
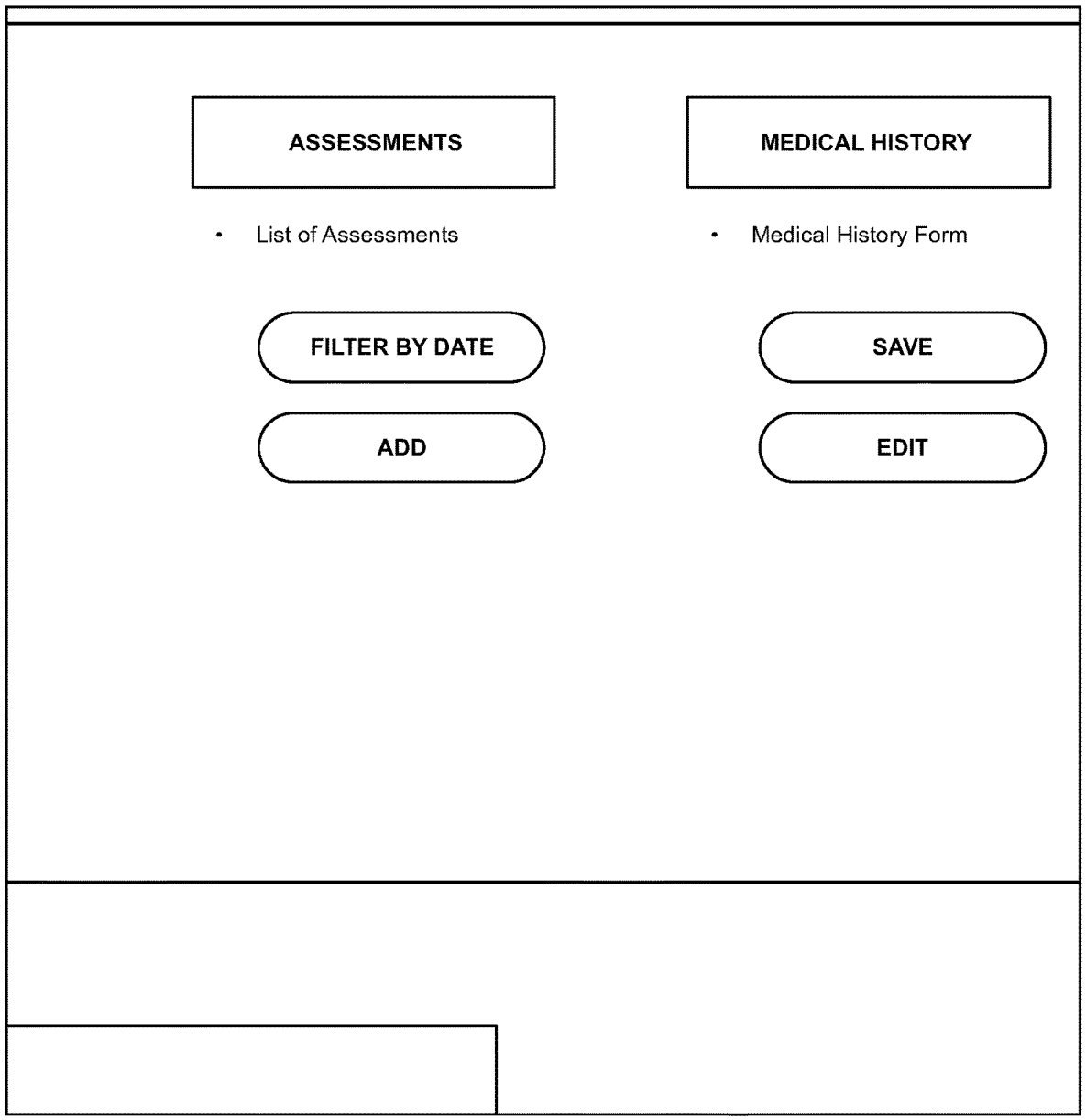
Figure 7N:
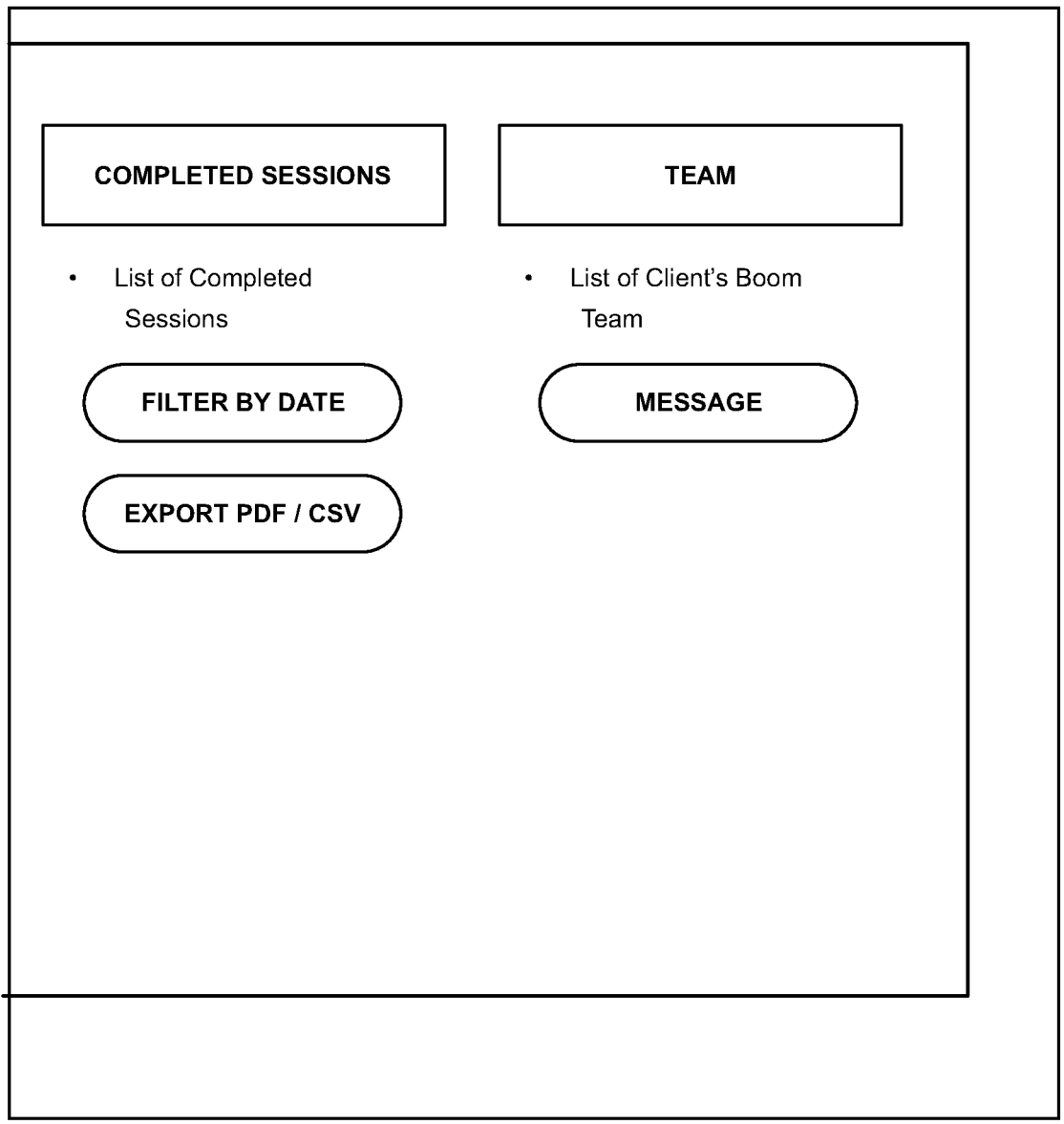
Figure 70:
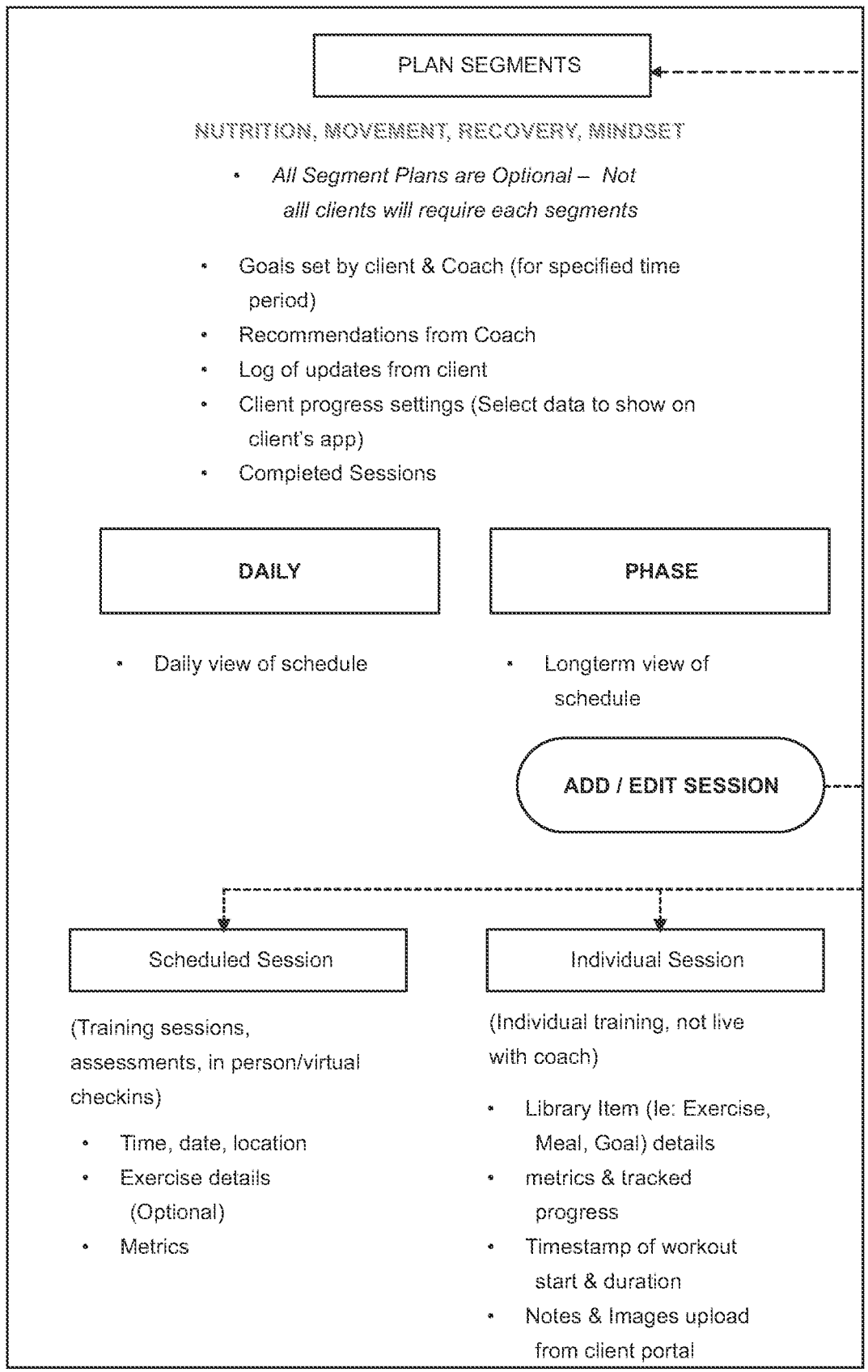
Figure 7P:
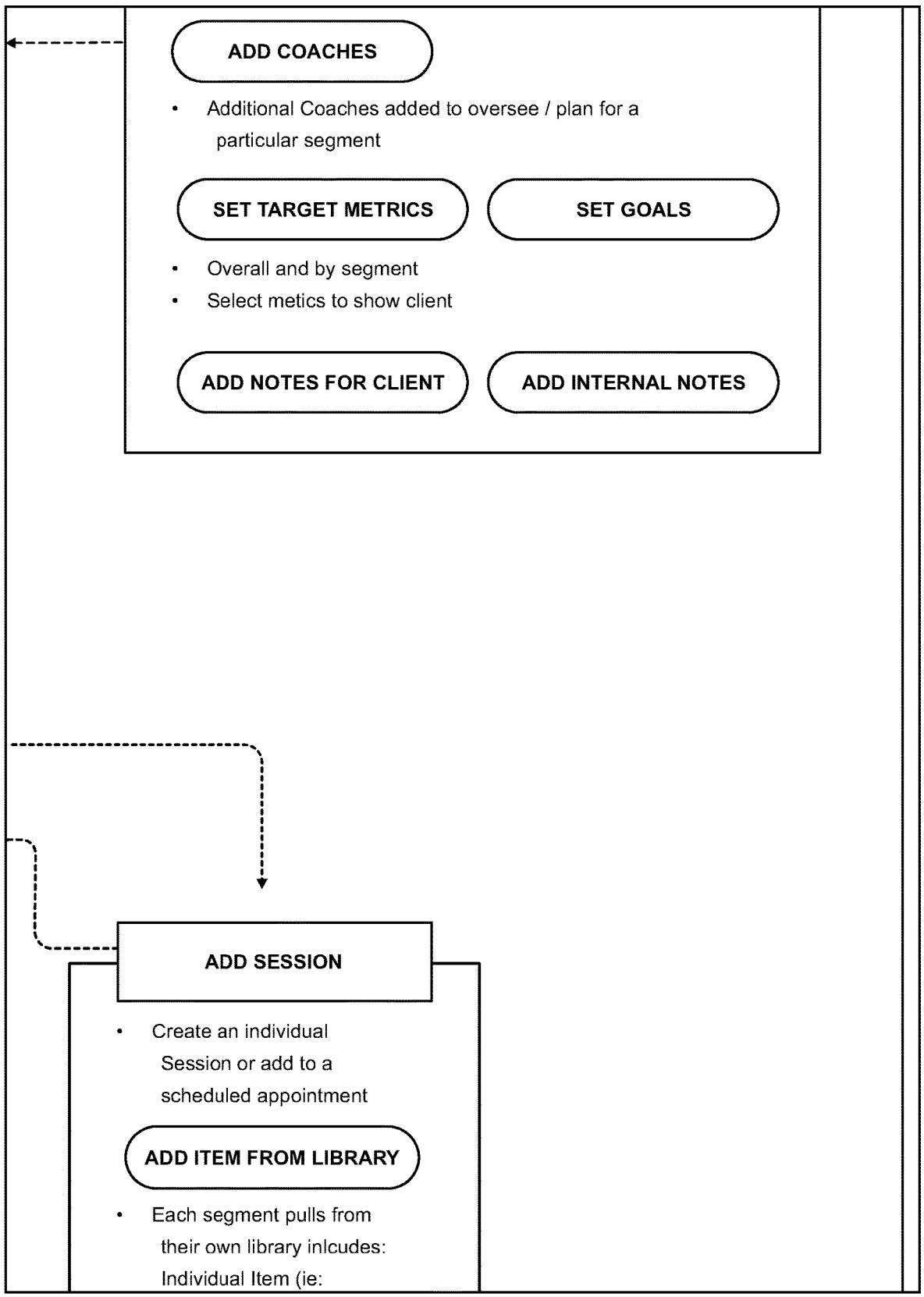
Figure 7Q:
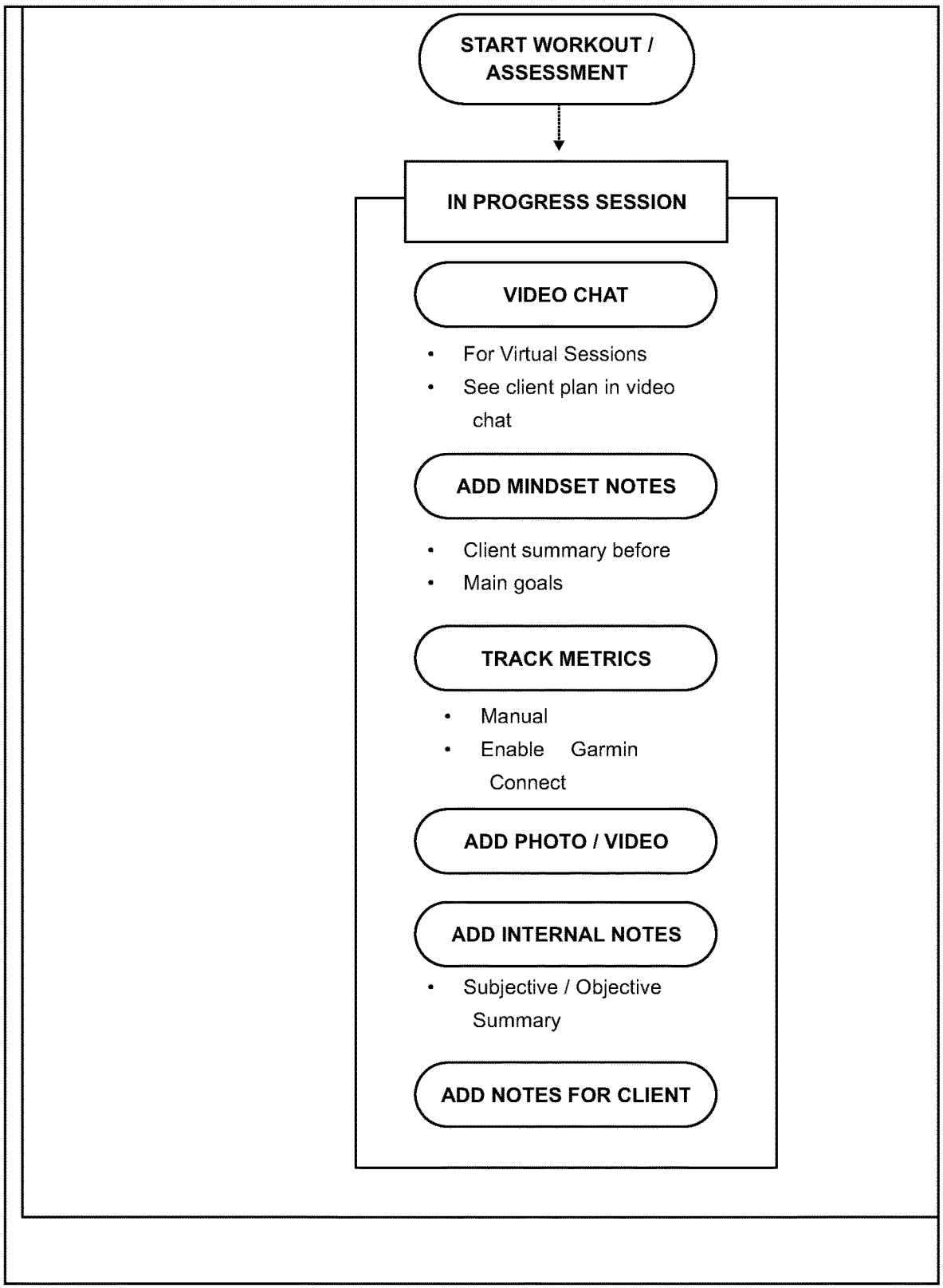
Figure 7R:
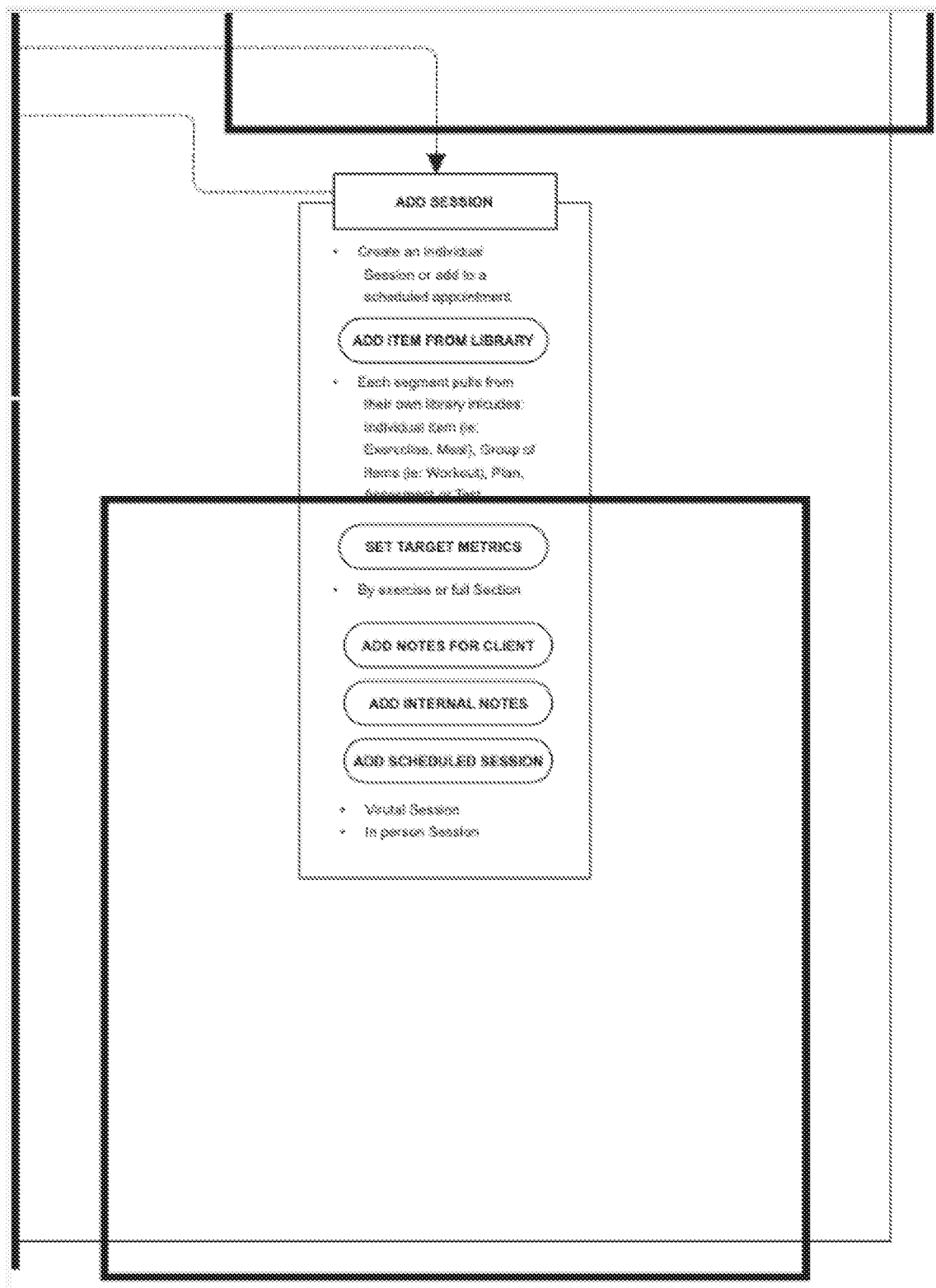

The biometric monitoring network 200 creates a program build, which models trends for the client based on biofeedback and tracking of biometric parameters, including data regarding medical history, behavior, movement, diet, sleep, exercise, heart rate, HRV, blood oxygen levels, physical therapy, and overall fitness. Movement models and nutrition models, as discussed in FIG. 4P, can be computationally calculated using computational assessments, including of calculations made based on user's habits, testing scores, tracked metrics including diet, recovery scores, sleep scores, exercise routines, prior records of health and fitness. Such movement models data can be used by the healthcare provider system in scoring and making recommendations regarding the user (client or patient). For example, trends in heart rate, HRV, blood oxygen levels, weight, exertion, strain, calories burned during exercise and during other daily activity can be used to calculate the confidence score. The confidence scoring can be used to help generate customized algorithms for physical therapy, nutrition, mindset personal training analysis and wellness recommendations for the client. See Appendix S—Metrics and Tracking.

The confidence score can be calculated using machine learning algorithms and deep learning. These algorithms can recognize patterns in the user's biometrics, e.g. medical history, behavior, movement, diet, sleep, exercise, heart rate, HRV, blood oxygen levels, physical therapy, and overall fitness. The system 200 can make predictions based on the program build (e.g. the modeled trends in the user's biometrics) to train the system 200. The system 200 can be trained use the biometric data (input data) to create machine learning models. The machine learning models can be used by the biometric app 208 and the health care provider system 204 to generate health-related AI processes that analyze relationships treatment techniques and client outcomes. AI techniques can be used to calculate the modeling and confidence scoring including support vector machines, neural networks, and decision trees. Each of these techniques have a training goal for the client and the system so classifications agree with the outcomes as much as possible. See, e.g. "Artificial intelligence in healthcare: past, present and future." Fei Jiang, Yong Jiang, Hui Zhi, Yi Dong, Hao Li, Sufeng Ma, Yilong Wang, Qiang Dong, Haipeng Shen, Yongjun Wang Stroke Vasc Neurol. 2017 December; 2(4): 230-243. Published online 2017 Jun 21. doi: 10.1136/svn-2017-000101 PMCID: PMC5829945, which is incorporated by reference in its entirety. https://www.ncbi.nlm.nih.gov/pmc/articles/PMC5829945/

Example Interface Components

In non-limiting examples, features of the biometric monitoring system may include a client portal, a team portal, a marketing site, a mobile application, and the white label product.

In a non-limiting example, the client portal may be implemented as a frontend web application used by clients to manage their health and fitness program, and schedule and track their progress. Users may receive customized health and fitness plans from their team of provider systems, as well as be able to input and track their own progress. The team portal is a backend platform for the client portal. The team portal provides the administrator, providers and concierge roles the ability to coordinate and manage clients and content. Features of the team portal include scheduling (including video conferencing), reporting and time management, task management, team management, location management, client management (such as creating and customizing client plans, and wearable technology integration with Garmin, for example), library and content management (such as sectors of content including movement, mindset, recovery and nutrition, and creating and utilizing health and fitness plan templates), messaging and marketing. Access to features is based on an individual permission structure that allows users to access content based on their assigned sector, location, clients and other individual customized permission criteria designated by the platform's administrator. The super super admin portal manages organizations utilizing the OS system in one or more private clouds. The super super admin is creating a new instance of the OS system that is a secure private cloud to ensure client private data security, and customization of organizational needs based on their biometric data tracking and assessment and evaluation processes of the biomarkers. The super super admin is the highest in the hierarchy.

Within the super super admin certain system components are available within the organization based on their respective, e.g. movement specific content, medical history, privacy data. These components can be securely turned on or off based on upon the needs of the organization as well as the scope and complexity and needs within each organization regarding storage and data allocation levels.

The super admin has the ability to customize the content within the system as it pertains to different elements that are stored within the system, for example, medical history may or may not be stored within the OS. The organization may have an external system server to manage pertinent medical data outside the system. The system may be utilized for health and fitness and patient data, integrating valuable components of wearable technology, smart program design and efficiency technology and patient monitoring. Additional custom elements such as customization of waivers, client information, and session names, i.e. movement may be called strength for a specific organization. This customization allows for an organization to both ensure that its data is securely stored and allows for allows for a seamless plan of care for patients and patient monitoring. See e.g. Appendix AA, Y and X.

In a non-limiting example, the consumer marketing site can allow the client portal users to access the sign up and log in flows from the consumer marketing site. The administrator node can require administrator access to a content management system (CMS) for managing content within the system. The mobile application can support both iOS and Android mobile devices. The app may allow users to quickly login to the system and be directed to the web application. The app may also feature the same pages that are in the healthcare provider website and may be managed from the same CMS.

With respect to the white label product, the sections of the web application may be built in a modular way that may make it easy to deploy the finished product to a white label customer. The technology may meet the needs of a long-term Infrastructure and platform as a service product. For The White Label Product, the separate modules include: content management system (CMS), administrator functionality, sign in and sign out, program builder, prospective client and client workflows, client billing, client medical history, team (employee) management, scheduling, video conferencing, messaging, locations management, room and equipment management for facilities, and wearable technology integration. The program builder includes sector management (a library, and philosophy, assessments and tests) and client planning. Prospective client and client workflows include client information, assessments, progress tracking, and completed tracking sessions. Locations management includes communities and facilities.

The team portal may utilize user-based permissions. The system administrator and users with designated access may be able to control individual user's permissions. The administrator may have all permissions turned on. The following permissions may be available to be turned on and off on a per-user basis. Account permissions, including document and biography and picture access. Locations permissions include adding new and existing locations, which locations a team member can view, which communities a user can view, and which facilities a user can view. Facility management permissions include the ability to see what users have access to a facility and the associated waivers, viewing the facility schedule, and viewing and adding new facility rooms and equipment. Home permissions include what calendars a user has access to view, the ability to schedule sessions for other users, the ability to assign tasks to others. Team permissions include the ability to add new team members, view existing team members, view team member profiles, edit team member profiles, edit team member permissions, view another team member's client list, view team members' completed sessions, export team members' completed sessions, view team members' documents and certifications, view and edit a team member's username and employee ID, and edit a team member's employee information. The program builder permissions include access to sector libraries, the ability to add/edit/delete sector library items, the ability to add/edit/delete sector habits and tools, the ability to create, view and edit program templates, assessments and tests, and access to a meal plan calculator.

Reporting permissions include access to a reporting side bar and the ability to export reports. Messaging permissions include which clients a user can message, viewing messaging history for specific clients, starting a group client channel, starting an internal channel, and access to concierge messaging. Videoconferencing permissions include access to videoconferencing and the ability to view video recordings of other users. Client permissions include viewing a list of active clients, viewing a list of prospective clients, viewing client details, viewing client waiver details, viewing client medical history, viewing completed sessions, exporting completed sessions, viewing and editing billing information, exporting billing history, viewing client's team, viewing client assessment details, viewing client test details, enabling wearable technology access, editing wearable technology analysis data, connecting wearable activities to the client plan, making wearable data visible to the client, and managing client permissions. Client planning permissions include adding a new phase, adding new weeks, scheduling sessions from a client's plan, changing session times from a client's plan, duplicating session content, viewing session details, editing session details, pushing wearable tracked sessions to a client's program, editing sidebar details, adding new sidebar details, editing a habits and routines toolbar, accessing a client's meal plan calculator in the side bar. Prospective client permissions include sending invite links to prospective clients and viewing prospective client contract proposals.

Users may have access to sector content based on their assigned sectors. Access to additional sectors can be granted using user-based permissions. Users may have access to clients based on their assigned clients. Access to additional clients can be granted using user-based permissions.

Team Portal
Marketing Site/CMS (Super Admin)

A site content CMS provides the ability to edit content on the site and create/read/update/delete functionality. An onboarding CMS provides a super admin member the ability to create forms and upload documents that are required during a new client onboarding, such as intake forms, medical questionnaires, and general waivers, for example. Term and conditions on the Site provide a super admin member the ability to add or edit the terms and conditions of the application. A privacy policy on the Site provides a super admin member the ability to add or edit he privacy policy for the application. A contact form CMS provides a team member the ability to edit the contact form in the CMS. A waivers CMS provides a super admin member the ability to edit and upload new waivers in the CMS. Proposal terms provide a team member the ability to edit the proposal terms template in the CMS.

Home and Schedule

Every provider has a home landing page that consists of a schedule, filter items, settings, task list and unique data visualization based on their role & clients. All components should function the same for each provider type with access to information based on permissions. Global components are used for all providers throughout the team portal. Navigation displays for all providers, at all times and displays each section based on permissions: account, home, clients, team, locations, program builder (movement, mindset, nutrition, recovery), messages, and reporting. Navigation states are based on provider permissions. Each section may display if the provider has access to it. Program builder content sections display based on providers assigned to certain sectors. Navigation state functionalities are further described in Appendix A of U.S. Provisional Application No. 63/222,861, filed on Jul. 16, 2021 A at pages 16-17, which is incorporated herein by reference in its entirety.

A calendar page displays for all providers on their home dashboard. Calendar functionality is the same for all providers. Content on a provider's calendar is dependent on the providers permissions and access to clients, locations, communities, facilities and team members. Calendar functionalities are described in Appendix A of U.S. Provisional Application No. 63/222,861, filed on Jul. 16, 2021 at pages 17-18. Dashboard metrics are displayed uniquely for administrators and providers. Metrics display on a provider's dashboard and contain content based on their role and assigned clients. Metrics display functionalities are described in detail in Appendix A of U.S. Provisional Application No. 63/222,861, filed on Jul. 16, 2021 at pages 19-20.

From the Home screen, providers can interact with the calendar in different states utilizing calendar overlays. The calendar overlays are further described in detail in Appendix A of U.S. Provisional Application No. 63/222,861, filed on Jul. 16, 2021 at pages 21-30. The Administrator home screen functionality is described at page 30 of Appendix A of U.S. Provisional Application No. 63/222,861, filed on Jul. 16, 2021. The Provider Home screen includes custom dashboard metrics based only on the Provider's clients. Access to information is based on the Provider's user permissions. The functionality of the Provider's Home screen is described in Appendix A of U.S. Provisional Application No. 63/222,861, filed on Jul. 16, 2021 at page 31. The Concierge's Home screen includes all components except for metrics. Access to information is based on a provider's permissions. The general functionalities of all Home screens are described in Appendix A of U.S. Provisional Application No. 63/222,861, filed on Jul. 16, 2021 at pages 32-34.

The task list is a global function for all team users on their home dashboard. All users have the functionality to view, add and edit their own tasks. Functionalities of the Task List are further described in detail in Appendix A of U.S. Provisional Application No. 63/222,861, filed on Jul. 16, 2021 at pages 35-41. Through the Task List a user can open a new task, edit an open task, and mark a task completed.

"Availability" is a global function for all team users on their home dashboard. All users can set their own availability window. When looking at a user's calendar that has an availability set, there is a visual indicator indicating what is in and out of that user's availability. Appointments can be scheduled outside a user's availability but may display an alert on the calendar creation overlay. Functionalities of Availability are described in detail in Appendix A of U.S. Provisional Application No. 63/222,861, filed on Jul. 16, 2021 at pages 41-47. Through Availability, a user can edit and set availability on one-day, multiple single dates and recurring days.

"Time Zone" is a global function for all users on their home dashboard. All users can set their own primary and secondary time zones to display. Default is to display one primary time zone in a user's current location. Functionalities of the Time Zone are described in detail in Appendix A of U.S. Provisional Application No. 63/222,861, filed on Jul. 16, 2021 at pages 48-52. A user can view a primary and secondary time zone. A user can also view a primary and secondary time zone in the calendar view.

Account

Every user has their own account page that houses their Details, Clients (if applicable), Permissions, and Completed (calendar items). The account dropdown menu appears on a side navigation for all users. Account pages are visible as "My Account" or accessible as a "Team" member account page. Content is either editable, read-only, or hidden based on user-based permissions. Functionalities of the Account page are listed in Appendix A of U.S. Provisional Application No. 63/222,861, filed on Jul. 16, 2021 at pages 52-60.

A team page is where information about the team members is located. Users can see a list of team members by selecting the Team Members tab and view team members based on their permissions. Users can view team member details based on their permissions. The Super Administrator/Administrator can view all team details for all team members. Providers can view a list of team members they have been given permission to view. Concierge can view a list of team members they have been given permission to view. Team detail information is accessible to Admin and those with user permission. View all Team Member Accounts directs the user to view all team members' details. Content is either editable, read-only, or hidden based on user-based permissions. Provider can view Team Member detail information based on the permissions set for them by the Administrator. Concierge can view Team Member detail information based on the permission set for them by the Administrator. A user's abilities to view a list of Team Member's clients is based on a user's permissions set by the Administrator. Permissions on the Team page assigns each user their permission settings. Each user is provided a role that has default permissions and additional user-based permission settings allows users to have more customized functionality and access. The Administrator can view all team member completed sessions. Provider and Concierge can view team member completed session based on user permissions. Functionalities of the Team page are listed in Appendix A of U.S. Provisional Application No. 63/222,861, filed on Jul. 16, 2021 at pages 61-74.

Locations

A "Locations" page displays locations. Locations are geographically designated areas that have one or more communities and/or facilities within that area. Team Members and Clients are assigned to one or more locations. Communities are a subdivision of a location that designates a smaller area of the location. Facilities are a specific building or place within a community. The Administrator, or those with access, have the ability to add and edit any Location, Community, or Facility. Provider can see the locations they have permission to view. Concierge can see only the locations they have permission to view. The Super Administrator/Administrator is able to create a new location, and view and edit information regarding location. The Super Administrator/Administrator is also able to list all communities within a location and add new communities to the database. Functionalities of the Locations page are listed in Appendix A of U.S. Provisional Application No. 63/222,861, filed on Jul. 16, 2021 at pages 74-85.

Facility Management

A "Facility Management" page manages scheduling within a facility that includes facility equipment, room reservations, and facility access. Provider and Concierge roles are based on user permissions. Displays, equipment and rooms are assigned within a facility. The Super Administrator/Administrator can add, edit and delete facility rooms and equipment from the page. Functionalities of the Facility Management page are listed in Appendix A of U.S. Provisional Application No. 63/222,861, filed on Jul. 16, 2021 at pages 85-87.

Reporting

A "Reporting" page is used by the Super Administrator/Administrator or by other users based on their permissions. Users can access data and pull reports from team members, clients, locations, communities and facilities. Functionalities and examples of the Reporting page are in listed in Appendix A of U.S. Provisional Application No. 63/222,861, filed on Jul. 16, 2021 at pages 88.

Program Builder

A "Program Builder & Library" page allows the Administrator and permissioned users to build out programs, templates, and sector-specific content for users to access. Team providers with permissions can access content in the program builder and libraries they have been granted access. The Administrator and Provider may also apply program templates to client plans. The content of this page is different for each sector, but the structure is the same. The content library of tools and habits on this page are functionally the same for all sectors. The tools and habits screen shows a high-level view of the various tools and habits that are searchable by name or applied tags. The detailed view of the tools and habits screen is only editable for providers if they have the appropriate user permission. The Program Builder & Library page contains a list of library items within a specific sector, with the unique ability to search via tags associated with each library item. Only users with appropriate user permission can edit the library items within a specific sector. The Program Builder & Library also contains a list of assessments within a specific sector. New assessments can be viewed, edited, deleted, or added by the Administrator or Team Members with the appropriate permission. Assessments are specific for each sector. Library Testing is a page accessible by the Administrator, contained within the Program Builder & Library page. Through the Library Testing page, an Administrator can view, edit, delete and add new tests to the library. Providers can edit and add new tests on the Library Testing page based on user permissions. Functionalities and examples of the Program Builder & Library page are listed in Appendix A of U.S. Provisional Application No. 63/222,861, filed on Jul. 16, 2021 at pages 89-103.

An Administrator can add new, edit, or delete programs or build a program template or a single template to be saved in the "Program Builder" for other users. Through the Program Builder page, a Provider can add new or edit programs or build a program or single template based on their permissions. Functionalities, accessible views and examples of the Program Builder are listed in Appendix A of U.S. Provisional Application No. 63/222,861, filed on Jul. 16, 2021 at pages 103-135.

Videoconferencing

Team Members with access to video conferencing can access the "Videoconferencing" pages and screens. Videoconferencing can be added to calendar sessions, based on permission to add videoconferencing. The time of a video chat is tracked as a "session" time under "Completed." Team Members can record video, screenshare, and view and edit the assigned client plan details alongside with video. Videoconferencing is configured to provide the Team Member with the ability to calculate movements, such as track angles, distance, and speed, for example. Functionalities, accessible views and examples of the Videoconferencing page are listed in Appendix A of U.S. Provisional Application No. 63/222,861, filed on Jul. 16, 2021 at pages 135-142.

Messages

A Team Portal user has access to a Messages page or window. Based on the user's role and permissions, they can have access to "Internal," "Clients," and/or "Concierge" messages. Users have access to send direct messages, access existing channels, and create new channels for specific locations and clients. Providers cannot start new channels or add participants to a channel unless they have the appropriate user permissions enabled. A user can elect to pop out their chat overlay so they can navigate through the portal while viewing the chat. Functionalities, accessible views, and examples of the Messages page or window are listed in Appendix A of U.S. Provisional Application No. 63/222,861, filed on Jul. 16, 2021 at pages 142-155.

Clients and Client List

A "Client List" is a list of clients. The Provider and the Concierge have access to clients within a selected location, community, facility, or specific clients based on their user permission. Users can view client details based on their permissions. The Provider can see a list of clients the Provider is assigned to, or clients at the location, community, or facility to which the Provider has access, based on the user's permissions. Every client has a detail page that includes their Progress, Plan, Assessments, Client Information, Team, Medical History, Completed Sessions, and Billing. The Administrator has access to all sections of Client Details. Providers and Concierge have limited access based on their permissions. On the Administrator's view, the client's progress summary displays high level metrics that are selected by the user to track in sectors over time. The Administrator or Provider has the option to make the metrics visible to the client and display on the client's portal on the Client's Progress page. The Provider view of the Client's Progress page displays high level metrics that are selected by the lead provider to track in sectors over time. Lead providers have the option to make the metric visible to clients and display on the client's portal. Functionalities, accessible views, and examples of the Client List are listed in Appendix A of U.S. Provisional Application No. 63/222,861, filed on Jul. 16, 2021A at pages 155-166.

Client Planning

A "Client Planning" page includes an Administrator's view of a Client Day and a Provider's view of a Client Day. A Client's Day Plan page provides views including an Administrator's view of the client's day plan view with the sector selector overlap open. The Client's Day Plan page also includes a Provider's view of the client's day plan with the sector selector overlay open. A Clients Day Plan Detail page includes a Provider view of the client day plan with a movement session opened without content added. The Client Planning page includes an Administrator view of the client day plan with overlay to add library items. In an example embodiment, an Administrator adds library items to a client session. The Client Planning page also includes a provider view of the client day plan with overlay to add library items. In an example embodiment, a Provider adds library items to a strength session. The Client Planning page also includes an overlay metric, which includes an Administrator and a Provider view of a client day plan with overlays related to adding Metrics to a Library Item. The Client Planning page also includes an Administrator view and a Provider view of a client day plan with the calendar/item schedule overlay. The Client Planning page also includes an Administrator view and a Provider view of a client plan with a session schedule. That view includes an expanded view of a session in the client plan that has been scheduled. The Client Planning page also includes an Administrator view of a completed session in the client plan. The Administrator and Provider views include a view of a client plan for a week. The Client Planning page also includes a Client Week Plan. The Client Week Plan includes an Administrator view and a Provider view of the client plan week view with a sector being added. A Client Week Plan detail view includes an Administrator view and Provider view of the client plan week view with a movement session opened without content added, and also includes an Administrator view and Provider view of the client plan week view with the overlay to add library items. In an example embodiment, the Administrator view and the Provider view of the client plan week view includes a function for adding library items to a high intensity interval training (HIIT) movement session. The Client Week Plan view also includes an Administrator and a Provider view of the client plan in the week with the overlays related to adding Metrics to a Library item. The Client Week Plan view also includes an Administrator view and a Provider view of the client plan in week view with the calendar item/schedule overlay. The Client Week Plan view also includes an Administrator view and a Provider view of the client plan week view with a scheduled session. The Client Week Plan view also includes an Administrator view and a Provider view of session details in the client plan week view. The Client Week Plan view includes an Administrator view and a Provider view of the client plan week view with a completed session that shows session details. The Client Planning page also includes an Administrator view and a Provider view of the client plan in the phase view. The Administrator view and Provider view of the client plan in the phase view includes a view of the client plan phase view with a sector being added. The client plan phase view includes an Administrator view and a Provider view with a movement session opened with or without content added. The client plan phase view also includes an Administrator view and Provider view of the client plan phase view with the overlay added to library items. In an example embodiment, the client plan phase view with the overlay includes adding library items to a HIIT movement session. The client phase plan page includes an Administrator view and a Provider view of the client plan phase view with the overlays related to adding Metrics to a Library item. The client plan phase view also includes an Administrator and a Provider view of the client phase plan view that includes the calendar item/schedule overlay. The client plan phase view also includes an Administrator view and a Provider view of the client plan phase view with a scheduled session. The client plan phase view includes a detailed schedule view, wherein an Administrator and a Provider view include an expanded view of a session in the client plan phase view. The client plan phase view also includes an Administrator view and a Provider view of the client plan phase view with a completed session with session details opened.

The Client Planning page also includes an Administrator view and a Provider view of a Client Plan Side Bar, also referred to herein as the Side Bar. The Side Bar view includes an Administrator view and a Provider view of a side bar for adding and viewing a client's plan overview. The Side Bar also includes an Administrator view and a Provider view of a side bar for adding and viewing a client's plan overview. The Side Bar view also includes a side bar with an Administrator view and a Provider view of a side bar to add or view a client's plan goals. The Side Bar view also includes an Administrator view and a Provider view for adding and viewing a client's Habits and Routines. The Side Bar view also includes an Administrator and a Provider view of a side bar for adding and viewing library items, which can be dragged and dropped into a client's plan. The Side Bar view also includes an Administrator view and a Provider view of a side bar for adding and viewing program templates, which can be dragged and dropped into a client's plan. The Side Bar view also includes an Administrator view and a Provider view of a sidebar for adding and viewing Assessments. New assessments can be dragged and dropped into a client's plan. The Side Bar view also includes an Administrator view and a Provider view of a side bar for adding and viewing tests. New tests can be dragged and dropped into a client's plan. The Side Bar view also includes an Administrator and a Provider view of a Meal Plan Calculator. Details regarding the Meal Plan Calculator can be found in Appendix B of U.S. Provisional Application No. 63/222,861, filed on Jul. 16, 2021 B. Functionalities, accessible views, and examples of the Client Planning page and the views included therein are listed in Appendix A of U.S. Provisional Application No. 63/222,861, filed on Jul. 16, 2021 at pages 166-213.

Client Details

A Client Details page includes an Administrator and a Provider view of a client's completed sessions, general assessments and detailed assessments, medical history, billing, invoice, team and team members, and permissions with respect to team members. Users can only view a client's medical history if the user has the appropriate permission. In an embodiment, there is an additional layer of security before a user accesses a client's medical history. An Administrator can view and update a client's contact and edit a client's billing information. The Administrator can export billing history in pdf or csv format. Other team members may only access the billing page for a client if having appropriate permissions. An Administrator manages and edits, adds, or deletes Team members within the Manage Permissions overlay in the Client Details page. Functionalities, accessible views, and examples of the Client Details page and views included therein are listed in Appendix A of U.S. Provisional Application No. 63/222,861, filed on Jul. 16, 2021 at pages 213-220.

Prospective Clients

Prospective clients are users that have not yet signed a contract for biometric monitoring services or been activated as a client. The users have access to the prospective client dashboard. Once a user has signed a contract, the Super Administrator/Administrator, or permissioned users can activate their account and gain access to the full client portal features. A prospective clients page includes prospective client information and progress. Once a user has completed the intake form, they become a prospective client. Information from the intake form feeds into the "Prospective Clients" information. The Super Administrator/Administrator, or user with permission, can view a list of prospective clients. Prospective clients have a series of steps and corresponding client portal tasks to complete to move to an Active Client. Administrators, Providers, and Concierge have access to view waivers signed by a prospective client. The progress on a prospective client's page includes assessments. Administrators and Providers have access to prospective clients' assessments. Functionalities, accessible views and examples of the Prospective Clients page are listed in Appendix A of U.S. Provisional Application No. 63/222,861, filed on Jul. 16, 2021 at pages 220-224.

Client Planning—Prospective Clients

A Client Planning for Prospective Clients page includes a view of a prospective client's day; a client's day plan with a sector added; a client's day plan with details added; an added library item to a sessions details in the prospective client plan day metrics associated with an assessment for the prospective client; a view for scheduling a session for a prospective client; a view of a scheduled assessment for a prospective client; a view of a completed assessment for a prospective client; a general week view of a prospective client; a week view of a prospective client with a sector added; a week view of a prospective client with a session added; a view of adding a library item to a session in a prospective client plan week; a view of setting up a session for a prospective client in the week view; a view of a scheduled assessment for a prospective client in a week view; a view of a scheduled session for a prospective client in a week view; a prospective client phase view; view of a prospective client's phase plan with a sector being added; view of a prospective client's phase plan with a session added; a view of adding a library item to a session in the prospective client's plan phase view; a view of setting up a session adding metrics for a prospective client in the phase view; a view of a scheduled assessment for a prospective client in the phase view; a view of a scheduled session with details for a prospective client in the phase view; a view of a completed assessment, including assessment details, for a prospective client in the phase view; a view of the prospective client's side bar details; a sidebar for adding library items, program templates, assessments, tests, and meal plan calculator to a prospective client plan; a view of a prospective client's completed sessions; a form editor for contract proposals; a view of a prospective client's invoices and billing statements; and a view of a prospective client's team members. Administrators can manage, edit, and delete prospective clients' Team Members with a "Manage Permissions" overlay. Functionalities, accessible views, and examples of the Client Planning for Prospective Clients page are listed in Appendix A of U.S. Provisional Application No. 63/222,861, filed on Jul. 16, 2021 at pages 224-249.

Client Planning—Garmin

A "Client Planning-Garmin" page includes a view of Garmin flow of the Client Plan day view; a view of the Garmin flow of a client day plan with a sector being added; a view of the client day plan with a new session being added and an option to enable Garmin; a view of creating a session and adding library items to a client day plan with Garmin enabled; a view of adding Garmin metrics to a client's session in a day view of the plan; a view of scheduling a session; a view of a scheduled session in a client's day plan view; a view of a scheduled session showing session details, wherein the Garmin function is enabled in a day view; a day view of the Garmin Connect Widget after a session has been completed; a day view of a client's full data set collected from Garmin after a completed session; a day view of client's session summary metrics, with metrics added from Garmin; a day view of a client's completed Garmin Activities; a week view of the Garmin flow of a Client Plan; a week view of the Garmin flow of a Client Plan with a sector being added; a week view of a client plan with a new session being added and an option to enable the Garmin function; a week view of creating a session and adding library items to a Client Plan with Garmin enabled; a week view of adding metrics to a session; a week view of scheduling a session in week view; a week view of a scheduled session in the Client Plan week view; a week view of a session with details scheduled with Garmin enabled; a week view of the Garmin Connect Widget after a session has been completed in the week view; a week view of the full data set collected from Garmin after a completed session in week view; a week view of session summary metrics with metrics added from Garmin in week view; a week view of completed Garmin Activities in week view; a phase view of the Garmin flow of a Client Plan in phase view; a phase view of the Garmin flow of a Client Plan with a sector being added; a phase view of the Client Plan with a new session being added and an option to enable Garmin; a phase view wherein a user creates a session and adds library to a Client Plan with Garmin enabled; a phase view of adding metrics to a session; a phase view of scheduling a session; a phase view of a scheduled session in the Client Plan; a phase view of a session with details scheduled with Garmin enabled; a phase view of the Garmin Connect Widget after a session has been completed; a phase view of the full data set collected from Garmin after a completed session; a phase view of session summary metrics with metrics added from Garmin; and a phase view of completed Garmin Activities. Functionalities, accessible views, and examples of the Client Planning page with the Garmin function are listed in Appendix A of U.S. Provisional Application No. 63/222,861, filed on Jul. 16, 2021 at pages 249-268.

Onboarding Sign-Up/Sign-In

Users that already have an account can log in via the "Sign In" page. Users that have forgotten their password can begin the "Recover Password User Flow" on the "Recover Password" page. The user must first enter their email address or username to receive an email with the link to reset their password. After a user submits their email address or username, the user may see a confirmation message that instructs them to check their email. The message should include the email address where the email was sent. A user should receive an email with a link to reset their password. The email includes the username for the user's account. The Recover Password page allows the user to reset their password to gain access to their account. If the user has forgotten their username, they can enter the email associated with their account to receive an email reminder of their username. After the user submits their email address, the user may see a confirmation message that instructs them to check their email. The user should receive an email with their username. The email should also include a link to the Sign In page. To begin the onboarding process for a new user, the new user must complete the "General Intake Form" during a sign-up process. The General Intake Form provides an administrator with information about the prospective client. After the user submits the General Intake Form, a confirmation message is displayed. The user receives an email confirmation that their intake form has been received and that a provider system affiliated with the biometric network system may contact them. The administrator, or users with permission, can send a "Login" email to the prospective client via the prospective client's profile in the Team Portal. The Login email links to a "Create Account" page, whereon the user can enter their given username to create an account in the Client Portal. On the Create Account page, a user is able to login with their username and set their password so they can gain access to their "Prospective Client" account in the Client Portal. Functionalities, accessible views, and examples of the Sign-Up and Sign In pages are listed in Appendix A of U.S. Provisional Application No. 63/222,861, filed on Jul. 16, 2021 at pages 268-271.

OS Client Portal

Landing

A "Landing" page is an example consumer marketing site for the biometric network system. Client portal users are able to access the sign up and log in flows from the consumer marketing site. The side navigation for the client/prospective client portal contains links to the main pages of the application. A top navigation bar contains an account and quick chat links. Functionalities, accessible views, and examples of the Landing page are listed in Appendix A of U.S. Provisional Application No. 63/222,861, filed on Jul. 16, 2021 at pages 272-273.

Dashboard

An "Active Client Portal Dashboard" includes a side bar component, a greeting component, a schedule component, a daily check-in component, and a habits and goals component. The schedule component is displayed in a "Today" view, by default. The schedule component is made up of a "Date/View" selector, and a "Schedule Block." The Date/View selector shows the dates of the schedule shown in a "Schedule Block." A dropdown allows the user to select which view of the schedule is displayed (month or week). In some example embodiments, the Schedule Block shows a week view. The week view includes a daily schedule. The daily schedule displays the client's schedule for that particular day. The schedule includes session blocks, each of which includes a sector, session details (showing detailed information about the selected session), a provider name (if a session is scheduled), a location (if associated), and a time (including time zone). An indicator displays the current time of any day. The daily check-in component appears below the schedule and corresponds to the date shown on the schedule, and includes metrics that providers designate to a user to input as prescribed or recommended. The daily check-in includes a date component, a metric inputs component, and a daily journal component. The date component corresponds to the day shown in the schedule above. The metrics input component allows the lead provider to select which metrics appear in the Daily Check-In page in the client's profile in the Team Portal. Input type is determined by the metric. The daily journal component is an open text field where the user can keep notes about their day and performance. The habits and goals component appears below the daily check-in items as designated by providers to focus on during the plan cycle. Habits Widgets display items that are recommended to focus on by the Team on the client's dashboard, the items comprising a tracking metric, habits, and goals. Functionalities, accessible views, and examples of the Dashboard page are listed in Appendix A of U.S. Provisional Application No. 63/222,861, filed on Jul. 16, 2021 at pages 273-274.

Account—Client

An "Account-Client" page includes a client's view of the client's account; a client's view of a list of completed sessions; a client's view of their contract, payment/billing details, and billing history; and a client's view of the invoice detail; a client's view of the client's medical history; and a client's view of the client's providers. With respect to medical history, the client first completes the medical history form during onboarding, but can access it in the account section to update it at any time. Access to that section requires a user to pass through a second layer of security. When a provider is assigned to a client in the Team Portal, the provider's photo and biography may appear on the My Team page with the ability to message the provider. Functionalities, accessible views, and examples of the Account—Client page are listed in Appendix A of U.S. Provisional Application No. 63/222,861, filed on Jul. 16, 2021 at pages 274-277.

Account—Garmin

An "Account — Garmin" page includes a client's view of their account with the ability to link their Garmin Connect Account; a client's view of the screen to connect their Garmin Connect Account; a client's view of logging into their Garmin Connect Account; a client's view of giving Garmin Connect permission to send and receive data from OS; a client's view of agreeing to the Garmin Privacy Policy; a client's view of their account information with Garmin Connect connected; a client's view of disconnecting their Garmin Connect account; and a client's view of their Garmin Connect activities. Functionalities, accessible views, and examples of the Account—Garmin page are listed in Appendix A of U.S. Provisional Application No. 63/222,861, filed on Jul. 16, 2021 at pages 277-279.

Dashboard—Prospective Client

A "Dashboard—Prospective Client" page displays a view prompting the prospective client to complete onboarding paperwork, required waivers and forms, and features the schedule component so the user can view upcoming onboarding consultations and assessments. When an administrator authorizes the contract proposal to be viewed by the client, a link to the contract proposal may appear on the prospective client's dashboard. To complete onboarding, the prospective client must accept terms of required waivers and input payment information. Functionalities, accessible views, and examples of the Dashboard — Perspective Client page are listed in Appendix A of U.S. Provisional Application No. 63/222,861, filed on Jul. 16, 2021 at pages 279-281.

Dashboard—Client

A "Dashboard—Client" page includes a today view, a session view including a workflow for clients to add notes, an individual view, a virtual session view, a location view, a schedule view showing completed and uncompleted sessions, an expandable week view, and an expanded view of a session detail. After completing a session, a client can view session summary metrics and the ability to share session summary to social media. Clients can view unscheduled sessions with full session details and multiple library items shared with the client. Clients have the ability to input metrics associated with library items or sets. Functionalities, accessible views, and examples of the Dashboard—Client page are listed in Appendix A of U.S. Provisional Application No. 63/222,861, filed on Jul. 16, 2021 at pages 281-287.

Dashboard—Garmin

Once a user has connected their Garmin Connect, the user can send a workout to their Garmin Device to follow a program sent to the device by a team provider. When the user has enabled Garmin Connect, activity from the device is synced to their account in the Client Portal. A "Dashboard—Garmin" page includes a view of a completed session pulling from Garmin and a data visualization from a session with Garmin Connect enabled. Functionalities, accessible views, and examples of the Dashboard—Garmin page are listed in Appendix A of U.S. Provisional Application No. 63/222,861, filed on Jul. 16, 2021 at pages 287-289.

Messages

A "Messages" page includes a client view to message a provider; a client view to message a concierge; a client pop-up to message a provider; a client pop-up to message a concierge; and a prospective client's view of messaging a concierge. Functionalities, accessible views, and examples of the Landing page are listed in Appendix A of U.S. Provisional Application No. 63/222,861, filed on Jul. 16, 2021 at pages 289-291.

Progress

A "progress" page shows data about the user's progression their program. The data shown is customizable and the client's providers control what data is shown on the Progress page. The progress page for a prospective client shows only the assessments and tests completed to view the results prior to becoming an active client. Functionalities, accessible views, and examples of the Progress page are listed in Appendix A of U.S. Provisional Application No. 63/222, 861, filed on Jul. 16, 2021 at pages 291-291.

Services

A "services" page contains information regarding non-limiting example features of the biometric network system. An active client and a prospective client service page contains the same information. Functionalities, accessible views, and examples of the services page are listed in Appendix A of U.S. Provisional Application No. 63/222, 861, filed on Jul. 16, 2021 at page 292.

Videoconferencing

A "videoconferencing" page includes a landing screen for users joining a video chat, a client's default view of active video chat, a client's gallery view of active video chat, and a client's gallery view of active video chat when more than two users are in the session. Functionalities, accessible views, and examples of the landing page are listed in Appendix A of U.S. Provisional Application No. 63/222, 861, filed on Jul. 16, 2021A at pages 293-294.

While example embodiments have been particularly shown and described, it may be understood by those skilled in the art that various changes in form and details may be made therein without departing from the scope of the embodiments encompassed by the appended claims.

What is claimed is:

1. A biometric computer network system comprising:
   a biometric monitoring cloud computing platform having a plurality of biometric monitoring network nodes configured to process biomarkers from biometric devices associated with a user device;
   each of the biometric devices being configured with one or more sensors, one or more processors, and memory;
   the one or more processors of the biometric devices are operatively connected with the memory, and the one or more sensors, where the memory stores computer-executable instructions for causing the one or more processors to transmit the biomarkers to the biometric monitoring cloud computing platform;
   the biometric monitoring cloud computing platform quantifying biomarkers to facilitate computation of movement models;
   the biometric monitoring cloud computing platform computing an encapsulated quantified assessment based on the movement models;
   the biometric monitoring cloud computing platform using the movement models to create a software movement library dynamically adapted to a movement profile generated for the user device; and
   at least one of the plurality of biometric monitoring nodes executing an instance of a virtual machine at a healthcare provider computing system to deploy an encapsulated quantified assessment derived at least in part on the biomarkers, the movement models, and the movement profile.

2. The biometric computer network system as in claim 1 wherein an artificial intelligence based video processing system component of the biometric monitoring cloud computing platform computationally processes a video signal having a plurality of frames depicting a user performing movements;
   the biometric monitoring cloud computing platform processing the plurality of video frames from the video signal to create a movement profile and movement models, where the movement models are an encoded form of video signal data from a plurality of video frames.

3. The biometric computer network system as in claim 2 wherein the artificial intelligence based video processing system component of the biometric monitoring cloud computing platform is configured to model such correspondences to generate the movement models.

4. The biometric computer network system as in claim 3 wherein the artificial intelligence based video processing system component of the biometric monitoring cloud computing platform is configured to model such correspondences to generate the movement models.

5. The biometric computer network system as in claim 3 wherein the artificial intelligence based video processing system component triggers a resampling request to dynamically update the software movement library, the artificial intelligence based video processing system responding by requesting another transmission of video signal having video framings depict the user performing further movements in response to a triggered reassessment;
   wherein the artificial intelligence based video processing system component of the biometric monitoring cloud computing platform is configured to model such correspondences to generate updated movement models.

6. The biometric computer network system as in claim 1 wherein a resampling of biomarkers from the biometric devices causes a new instance of the encapsulated quantified assessment to be quantified.

7. The biometric computer network system as in claim 6 wherein the resampling is triggered in response to a scheduled push or pull nonfiction to secure new biomarkers from one or more of the biometric devices.

8. The biometric computer network system as in claim 7 wherein the resampling is triggered in response to a trigger detected by the biometric monitoring cloud computing platform.

9. The biometric computer network system as in claim 8 wherein the trigger detected by the biometric monitoring cloud computing platform is caused by one or more of the following: automatic reassessments at scheduled intervals; push or pull notifications based on volume of progress and frequency of data collection of biomarkers; detected injury of the user; detected movement pattern progression of the user can trigger an automatic reassessment of biomarkers; a recovery score in the biomarkers being consistently low relative to baseline over a period of time; consistently low sleep scores in the biomarkers over time; variations or irregular respiration rate readings in the biomarkers; repeated heart-rate recovery (HRV) readings in the biomarkers; variations or irregular resting heartrate readings in the biomarkers; body temperature readings consistently two degrees above normal rate in the biomarkers; recovery scores dropping 10% or more on certain ones of the biomarkers.

10. The biometric computer network system as in claim 9 wherein the certain ones of the biomarkers are readiness score, sleep score, and respiration.

11. The biometric computer network system as claim 8 wherein the trigger causes a new data sets of biomarkers to be obtained from the biometric devices for dynamic computation of dynamic movement patterns to create modeled movements for the movement library.

12. The biometric computer network system as in claim 1 wherein a motion signal from at least one of the biometric devices is used by one or more of the plurality of biometric monitoring network nodes to model correspondences to generate the movement models for the software movement library; and the biometric monitoring cloud computing platform is configured to reduce computational processing latency in the biometric computer network system by creating predicted movement models for the software movement library based on the generated movement models.

13. The biometric computer network system as in claim 12 wherein the predicted movement models include machine learning models generated based on recommendations from a machine learning system in the biometric monitoring cloud computing platform;

the machine learning system configured to recognize patterns in signal output in the biometric devices quantify predictions d based on modeled trends in the movement models.

14. The biometric computer network system as in claim 12 wherein the at least one of the biometric devices is configured as a physiological signal processing system that includes an inertial sensor and a photoplethysmograph (PPG) sensor;

physiological signal processing system processing physiological waveform output from the photoplethysmograph (PPG) sensor and the inertial sensor to generate the movement models;

a physiological metric sampler is configured to extract and encode a physiological metric from the physiological waveform that is generated by the photoplethysmograph (PPG) sensor; and the physiological metric sampler including a resampler that resamples subsequent instances the motion signal and normalizes the resampled signal to create at least a portion of the movement models based on the physiological waveform output.

15. The biometric computer network system as in claim 12 wherein the biometric monitoring cloud computing platform computes the encapsulated quantified assessment based in part on the predicted movement models.

16. The biometric computer network system as in claim 1 wherein the movement models are generated based on signal output from (1) the biometric devices including blood glucose, blood oxygen, blood pressure signal output; and (2) metrics related to body fat, body mass index, and genetic information.

17. The biometric computer network system as claim 1 wherein the biometric monitoring cloud computing platform the plurality of biometric monitoring network nodes as a biometric monitoring network operating in an open feedback loop, the biometric computer network providing secure access to an application programming interface to the biometric monitoring network via a security component.

18. A computer implemented method for implementing a biometric computer network comprising:

providing a biometric monitoring cloud computing platform having a plurality of biometric monitoring network nodes configured to process biomarkers from a plurality of biometric devices associated with a user device, where each of the plurality of biometric devices being configured with one or more sensors, one or more processors, and memory;

causing the one or more processors to transmit the biomarkers to the biometric monitoring cloud computing platform;

directing an instance of a virtual machine at a provider computer server to deploy an encapsulated quantified assessment derived in part from quantifying the biomarkers from the biometric devices;

the biometric monitoring cloud computing platform computing the encapsulated quantified assessment based on movement models derived at least in part from quantifying the biomarkers;

modeling predicted movement models based on the quantified assessment derived from the biomarkers and the biomarkers;

providing a software movement library dynamically adapted to movement profiles associated with the user device;

integrating the predicted movement models in the software movement library at the biometric monitoring cloud computing platform; and transmitting an encoded version of the movement profiles to a service provider node in secure computer network communication with the biometric monitoring cloud computing platform.

* * * * *